United States Patent
Holop et al.

(10) Patent No.: US 11,020,190 B2
(45) Date of Patent: Jun. 1, 2021

(54) AUTOMATED INSTRUMENT PRELOAD ENGAGE/DISENGAGE MECHANISM

(71) Applicant: INTUITIVE SURGICAL OPERATIONS, INC., Sunnyvale, CA (US)

(72) Inventors: Robert E. Holop, Santa Clara, CA (US); Todd R. Solomon, San Jose, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 108 days.

(21) Appl. No.: 16/317,484

(22) PCT Filed: Jun. 21, 2017

(86) PCT No.: PCT/US2017/038455
§ 371 (c)(1),
(2) Date: Jan. 11, 2019

(87) PCT Pub. No.: WO2018/013303
PCT Pub. Date: Jan. 8, 2018

(65) Prior Publication Data
US 2019/0298461 A1    Oct. 3, 2019

Related U.S. Application Data

(60) Provisional application No. 62/362,176, filed on Jul. 14, 2016.

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/70* (2016.02); *G16H 40/63* (2018.01);
(Continued)

(58) Field of Classification Search
CPC .......... A61B 34/30; A61B 2017/00477; A61B 2034/302; B25J 9/1641; F16H 25/2015; F16H 2025/2075; G05B 2219/41032
See application file for complete search history.

(56) References Cited

U.S. PATENT DOCUMENTS 7,048,745 B2    5/2006   Tierney et al.
7,699,855 B2    4/2010   Anderson
(Continued)

FOREIGN PATENT DOCUMENTS

WO   WO-2005039835 A1    5/2005
WO   WO-2015023834 A1    2/2015
(Continued)

OTHER PUBLICATIONS

International Search Report and Written Opinion for Application No. PCT/US2017/038455, dated Oct. 19, 2017, 12 pages.
(Continued)

*Primary Examiner* — George J Ulsh
(74) *Attorney, Agent, or Firm* — Artegis Law Group, LLP

(57) ABSTRACT

A surgical system includes a preload assembly in a surgical instrument surgical instrument manipulator that is under the control of a controller. The controller can automatically cause the preload assembly to engage and disengage a preload. A surgical apparatus includes a surgical instrument manipulator assembly and a sterile adapter assembly. The sterile adapter assembly is mounted in the distal face of the surgical instrument manipulator assembly. When the preload assembly configures the surgical instrument manipulator assembly to apply a preload force on the sterile adapter
(Continued)

assembly, the sterile adapter assembly is removable from the distal face of the surgical instrument manipulator. The sterile adapter assembly includes a mechanical sterile adapter assembly removal lockout and a mechanical surgical instrument removal lockout.

15 Claims, 26 Drawing Sheets

(51) Int. Cl.
  *G16H 40/63* (2018.01)
  *A61B 90/00* (2016.01)
(52) U.S. Cl.
  CPC ... *A61B 2034/302* (2016.02); *A61B 2034/305* (2016.02); *A61B 2090/031* (2016.02)

(56) References Cited

U.S. PATENT DOCUMENTS

| | | |
|---|---|---|
| 7,942,868 B2 | 5/2011 | Cooper et al. |
| 2002/0111635 A1 | 8/2002 | Jensen et al. |
| 2003/0036748 A1 | 2/2003 | Cooper et al. |
| 2009/0024142 A1 | 1/2009 | Ruiz |
| 2012/0245596 A1 | 9/2012 | Meenink et al. |
| 2016/0184035 A1 | 6/2016 | Cooper et al. |
| 2016/0184036 A1 | 6/2016 | Solomon et al. |
| 2016/0184037 A1 | 6/2016 | Cooper et al. |

FOREIGN PATENT DOCUMENTS

| | | |
|---|---|---|
| WO | WO-2015023840 A1 | 2/2015 |
| WO | WO-2015023853 A1 | 2/2015 |
| WO | WO-2018013214 A1 | 1/2018 |
| WO | WO-2018013236 A1 | 1/2018 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

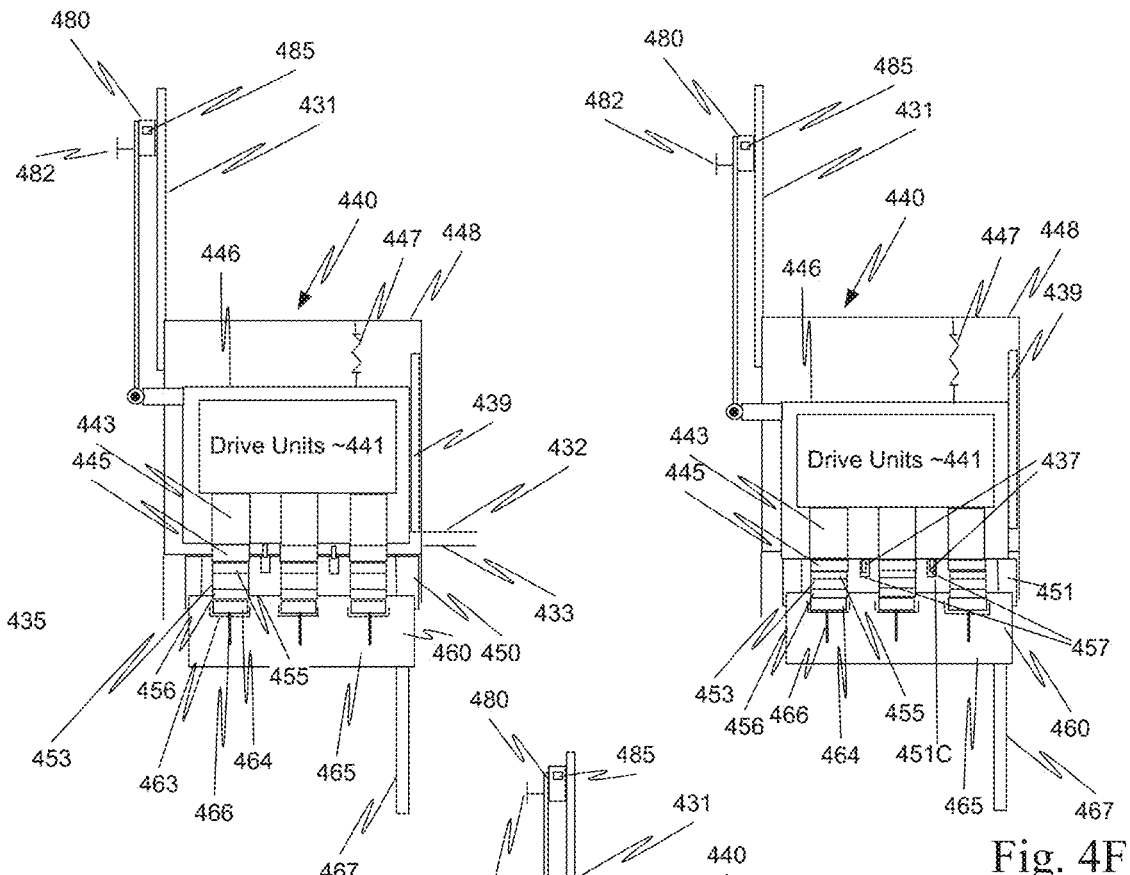
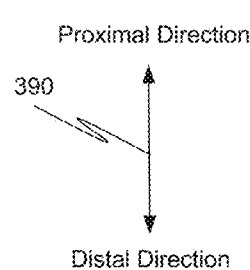
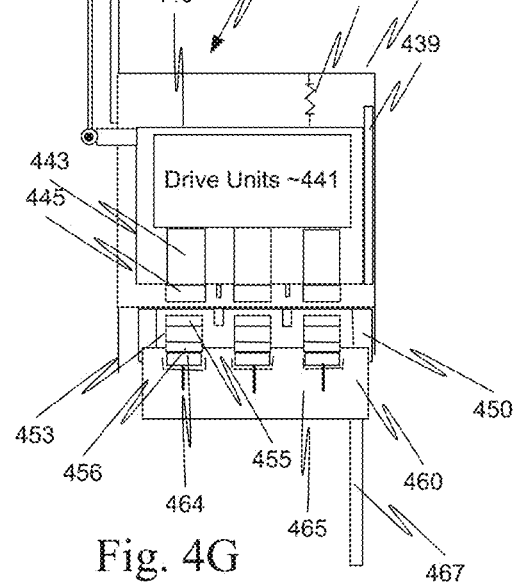
Fig. 4E
Fig. 4F
Fig. 4G

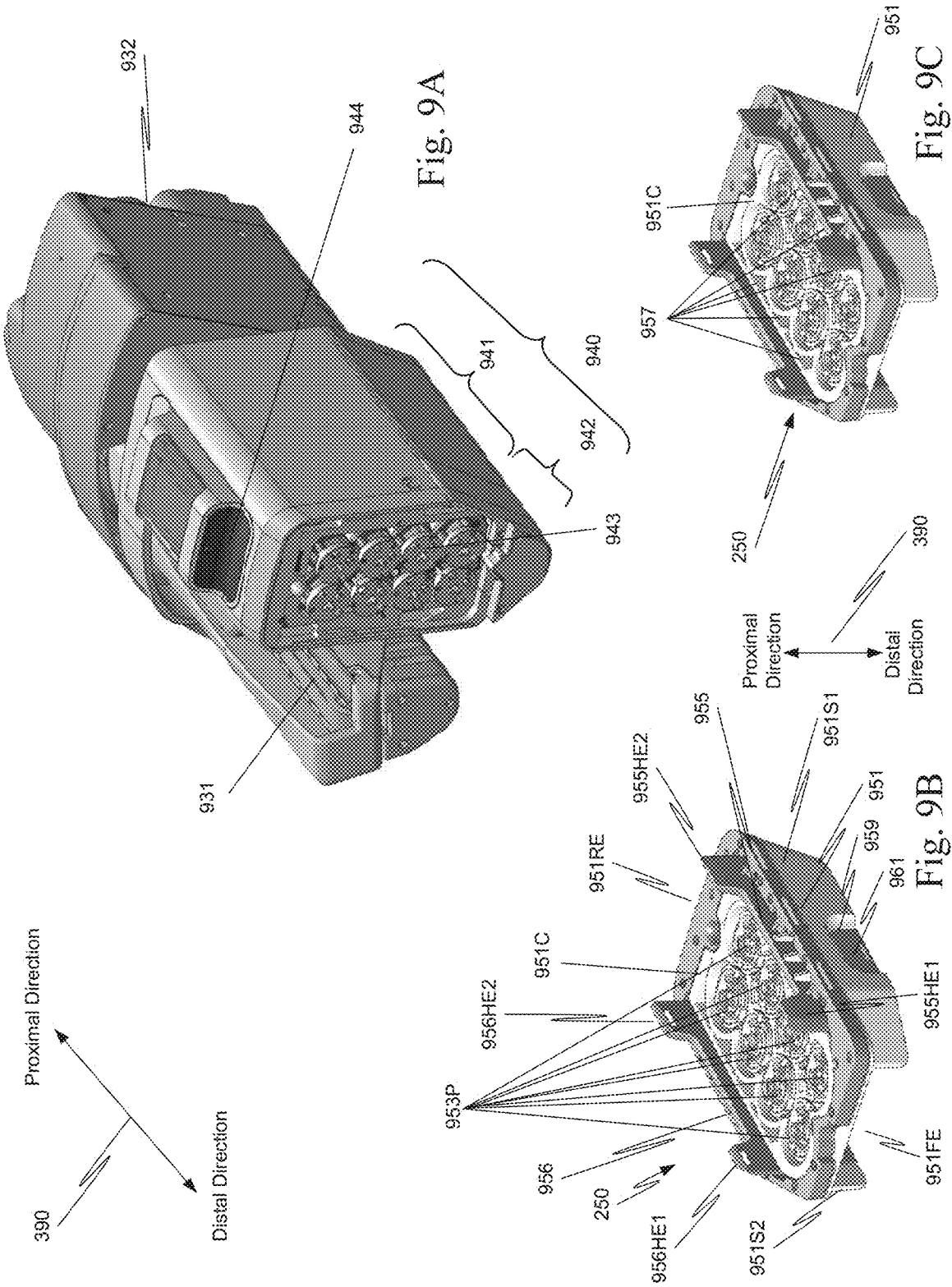

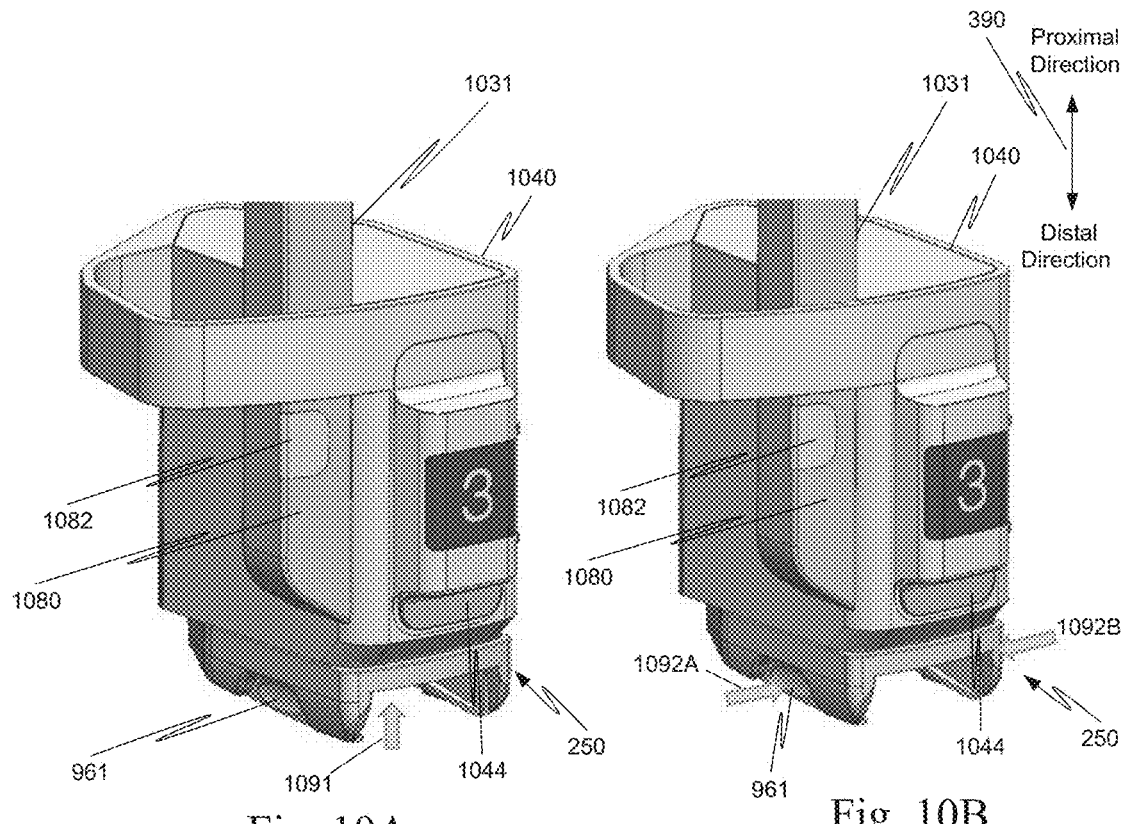
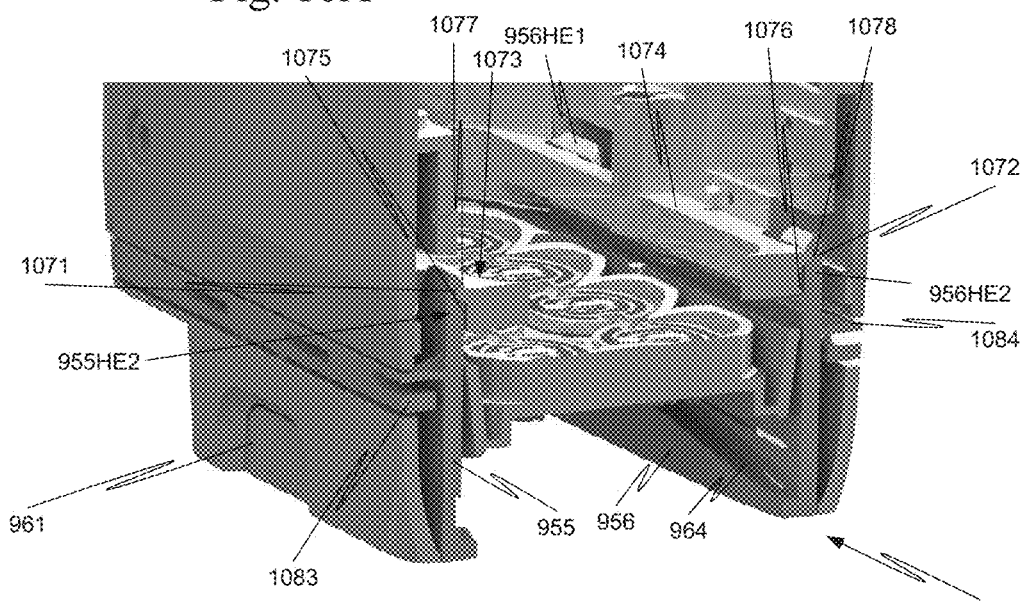

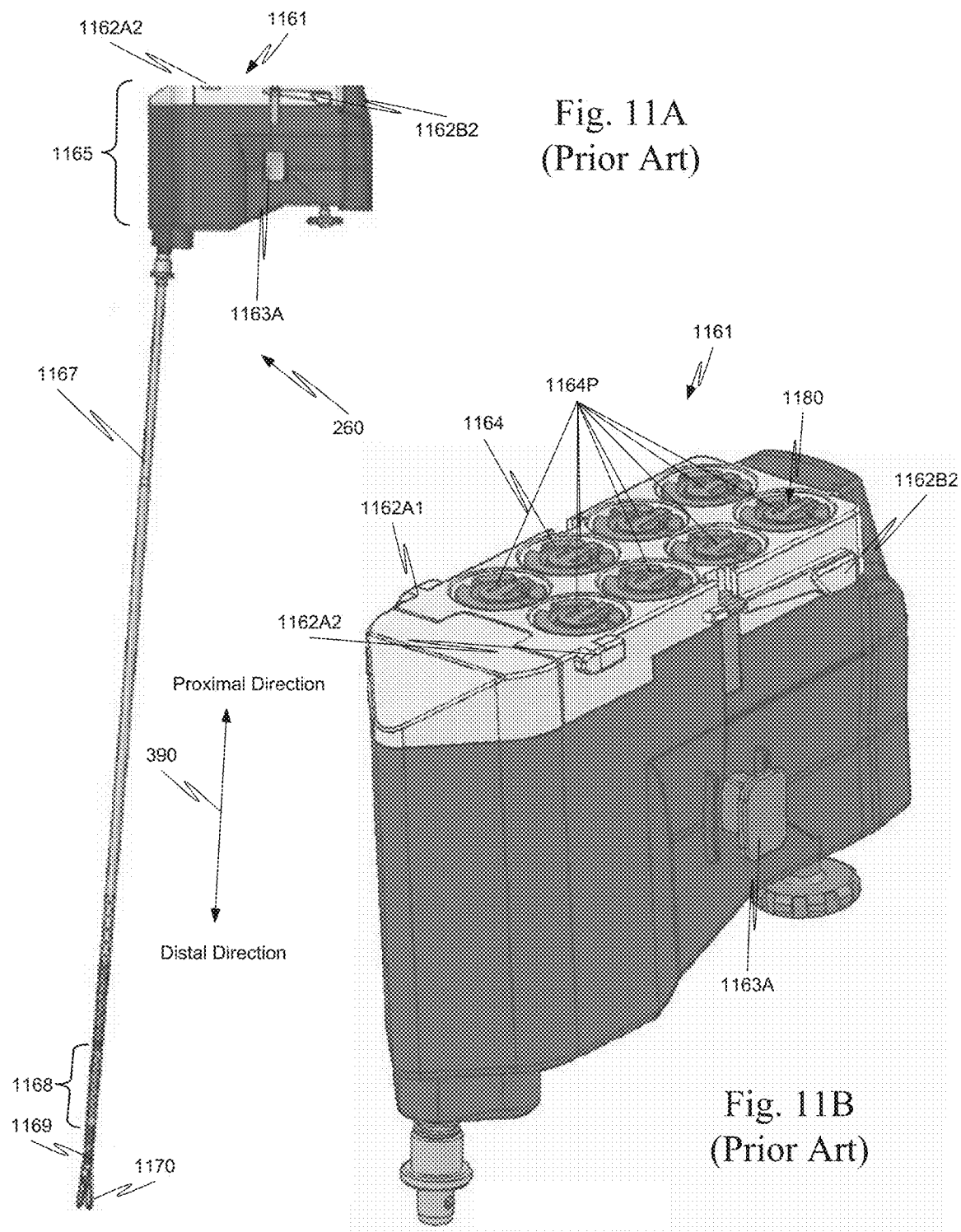

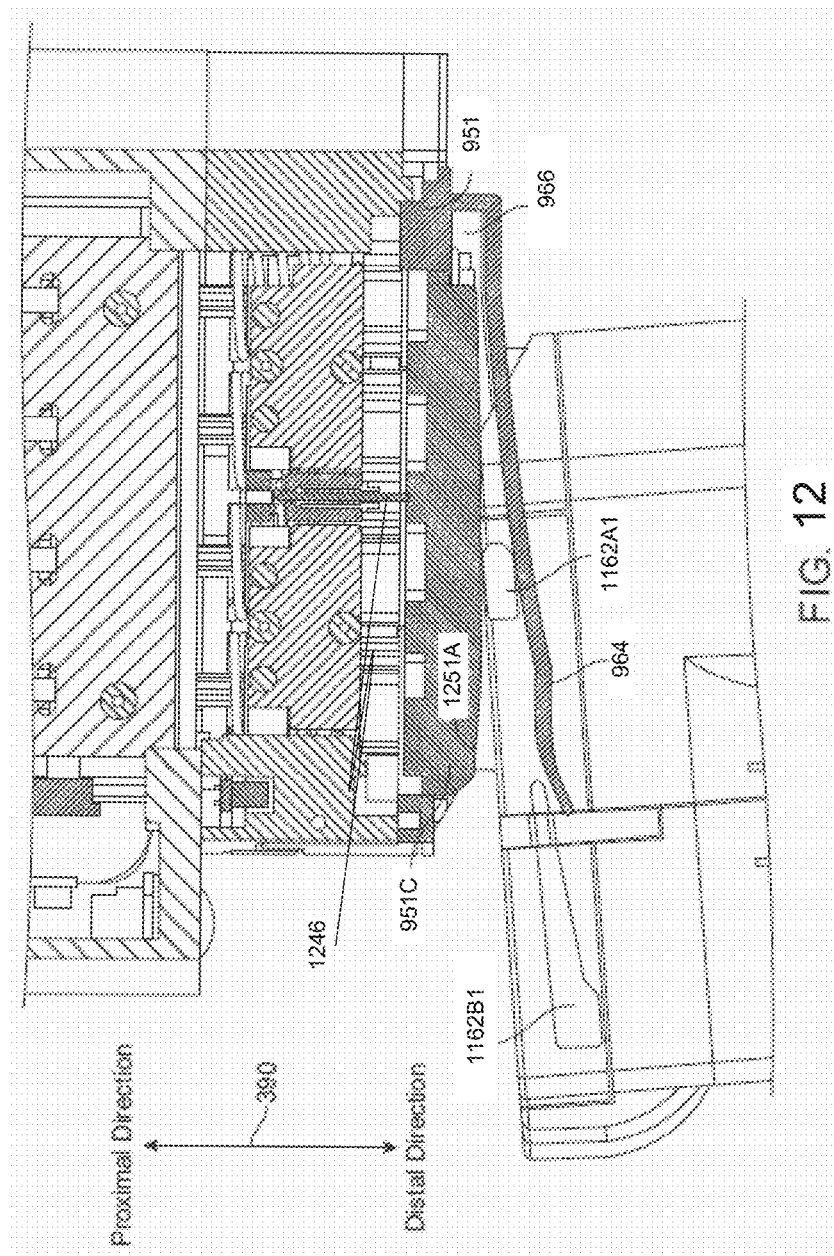

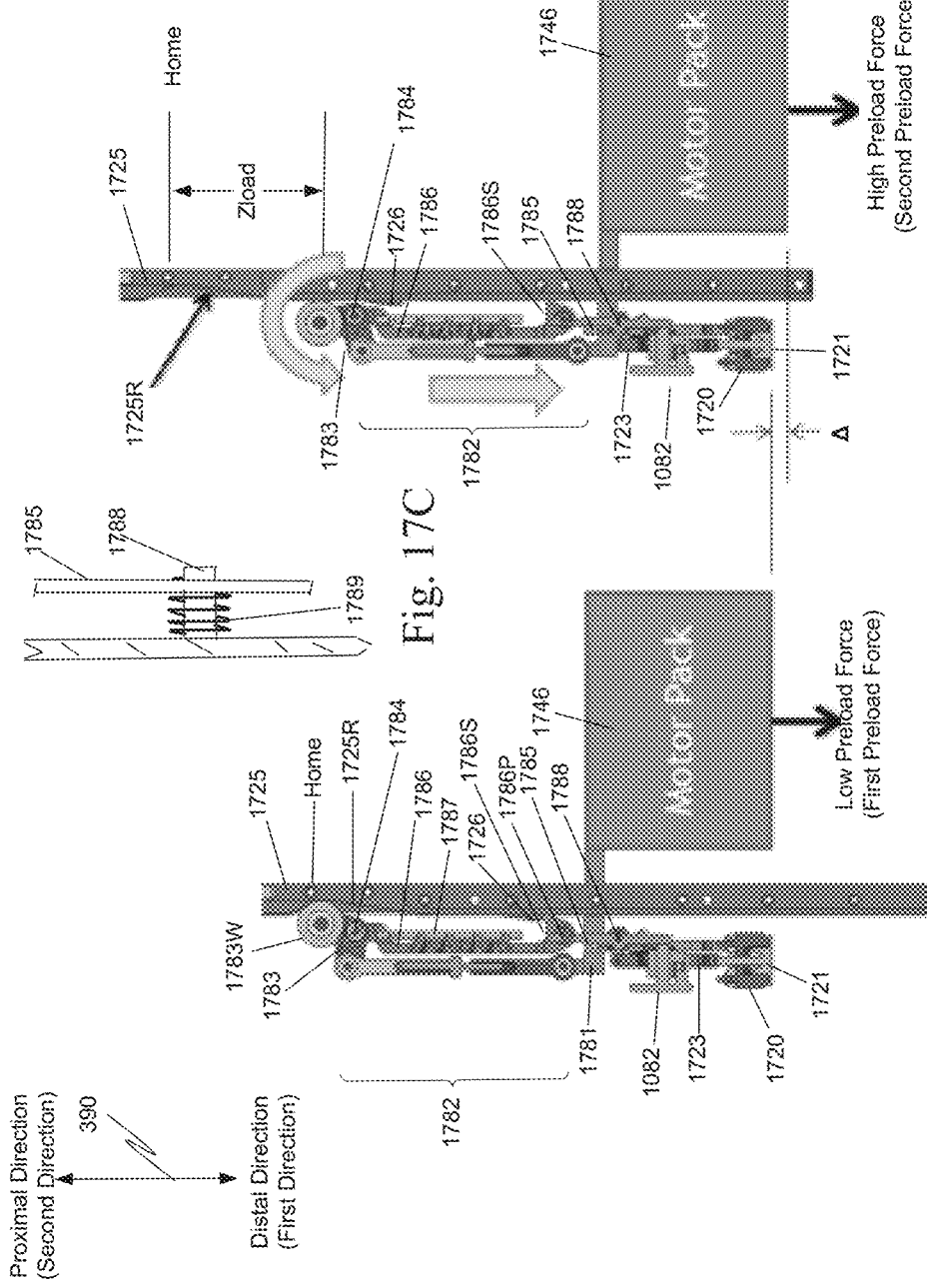

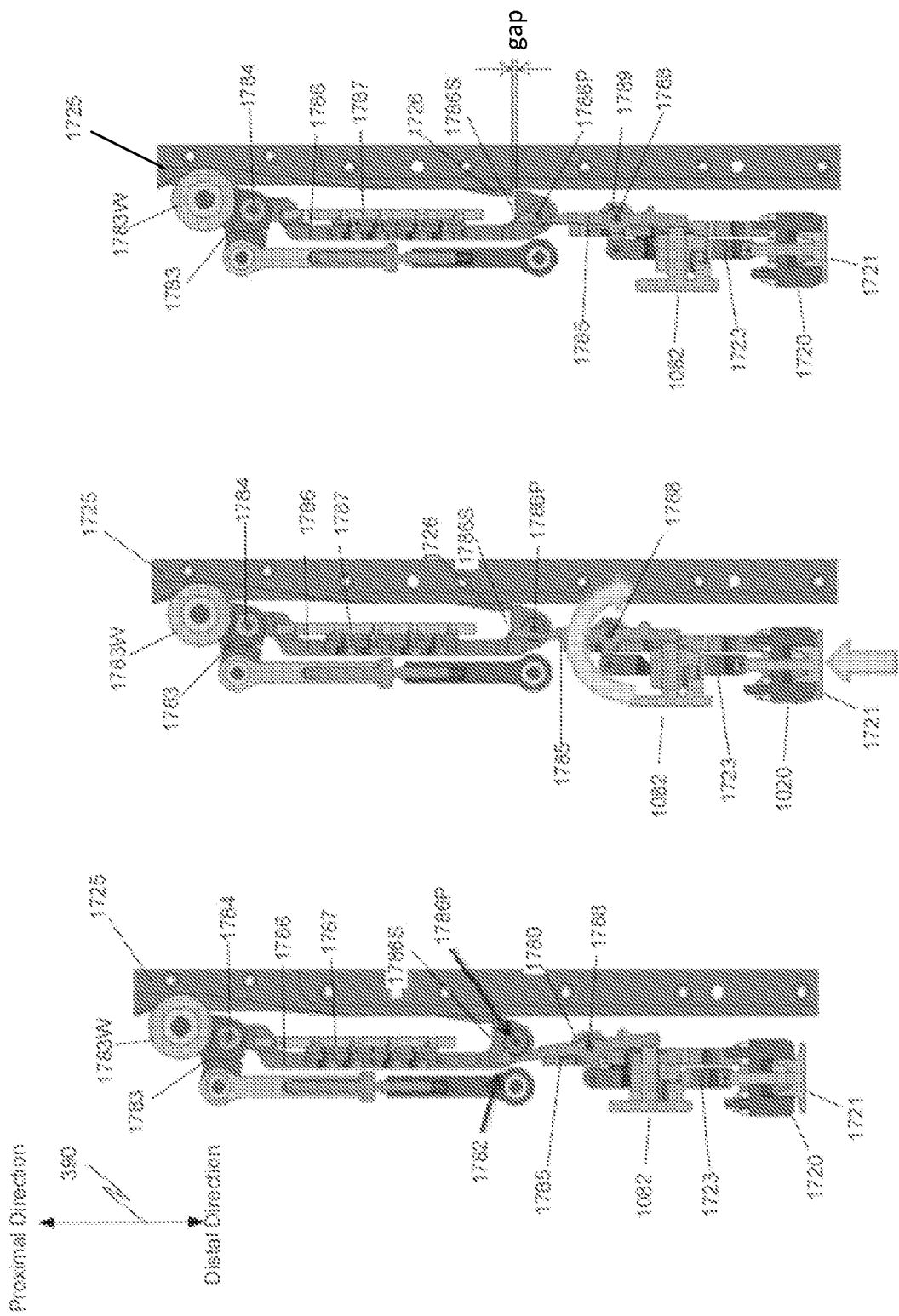

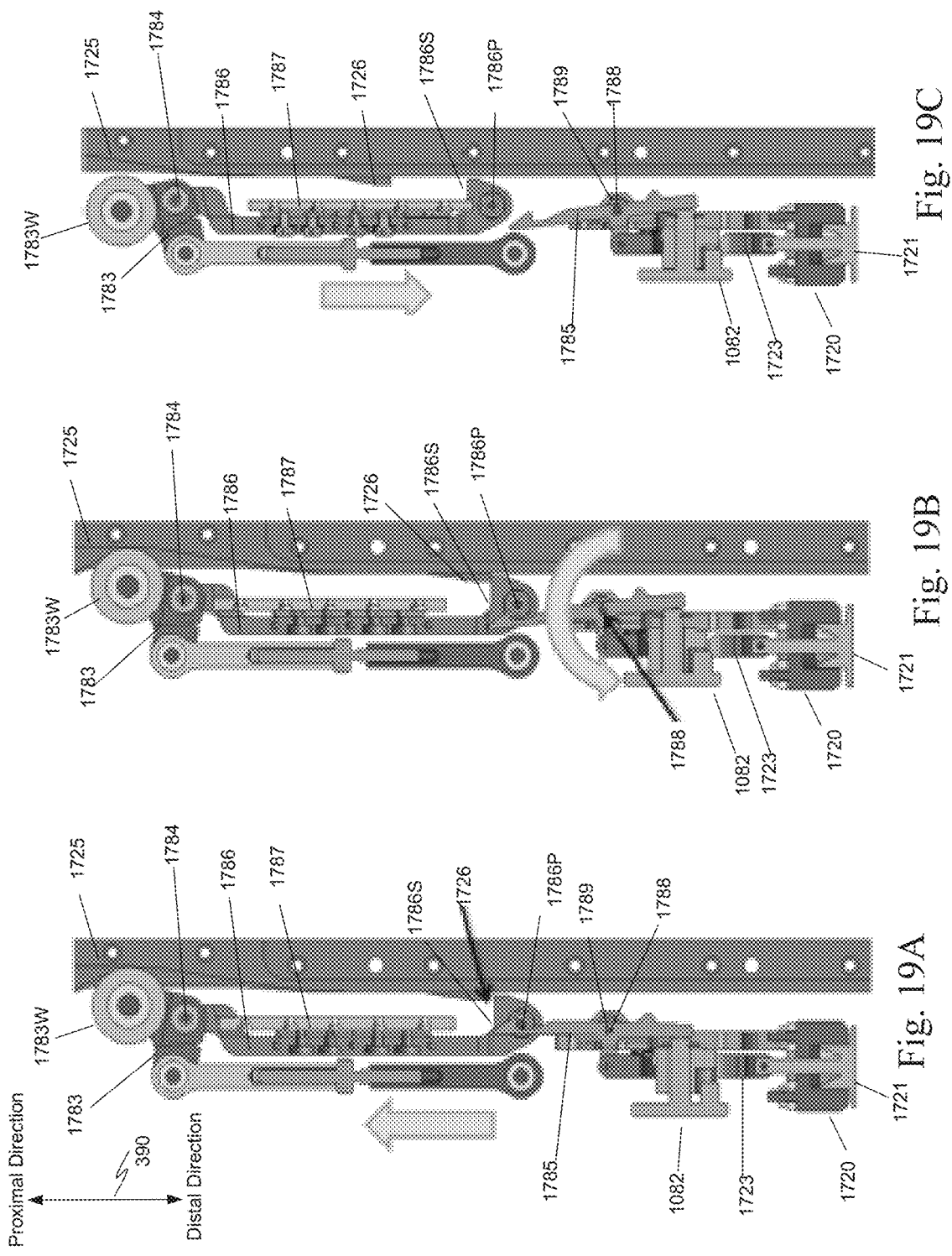

AUTOMATED INSTRUMENT PRELOAD ENGAGE/DISENGAGE MECHANISM

RELATED APPLICATIONS

This patent application is a U.S. National Stage patent application of International Patent Application No. PCT/US2017/038455, filed on Jun. 21, 2017, the benefit of which is claimed, and claims priority to and the benefit of the filing date of U.S. Provisional Patent Application 62/362,176, entitled "AUTOMATED INSTRUMENT PRELOAD ENGAGE/DISENGAGE MECHANISM" filed Jul. 14, 2016, each of which is incorporated by reference herein in its entirety.

BACKGROUND

Field of the Invention

The present invention relates generally to teleoperated instruments and systems, and more particularly to teleoperated instruments and systems that utilize preload forces.

Description of Related Art

Robotically controlled systems such as employed for minimally invasive medical procedures can include large and complex equipment to precisely control and drive relatively small tools or instruments. (As used herein, the terms "robot" or "robotically" and the like include teleoperation or telerobotic aspects.) FIG. 1A illustrates an example of a known robotically controlled system 100. System 100, which may, for example, be part of a da Vinci® Surgical System commercialized by Intuitive Surgical, Inc., includes a patient-side system 110 having multiple arms 130. Each arm 130 has a docking port with a drive system 140 that generally includes a drive system with a mechanical interface for mounting and providing mechanical power for operation of an instrument 150. Arms 130 can be used during a medical procedure to move and position respective instruments 150 for the procedure.

FIG. 1B shows a bottom view of a known instrument 150. Instrument 150 generally includes a transmission or backend mechanism 152, a main tube 154 extending from the backend mechanism 152, and a functional tip 156 at the distal end of the main tube 154. Tip 156 generally includes a medical tool such as a scalpel, scissors, forceps, or a cauterizing instrument that can be used during a medical procedure. Drive cables or tendons 155 are connected to tip 156 and extend through main tube 154 to backend mechanism 152. Backend mechanism 152 typically provides a mechanical coupling between drive tendons 155 of the instrument 150 and motorized axes of the mechanical interface of a drive system 140. In particular, gears or disks 153 have features such as projections or holes that are positioned, sized, and shaped to engage complementary features on the mechanical interface of a drive system 140. In a typical instrument, rotation of disks 153 pulls on respective drive tendons 155 and actuates corresponding mechanical links in tip 156. System 100 can thus control movement and tension in drive tendons 155 as needed to position, orient, and operate tip 156. Further details of known surgical systems are described, for example, in U.S. Pat. No. 7,048,745 (filed Aug. 13, 2001) to Tierney et al., entitled "Surgical Robotic Tools, Data Architecture, and Use," which is hereby incorporated by reference in its entirety.

Instruments 150 of system 100 can be interchanged by removing one instrument 150 from a drive system 140 and then installing another instrument 150 in place of the instrument removed. The installation process in general requires that the features on disks 153 properly engage complementary features of drive system 140. However, before installation, the orientations of disks 153 on instrument 150 are generally unknown to patient-side system 110.

Further, equipment such as patient-side system 110 is often covered for a medical procedure by a sterile barrier (e.g., a plastic sheet drape) because of the difficulty in cleaning and sterilizing complex equipment between medical procedures. This sterile barrier can include a sterile adaptor that is interposed between the docking port associated with drive system 140 and instrument's backend mechanism 152. See for example, U.S. Pat. Nos. 7,048,745 and 7,699,855 (filed Mar. 31, 2006) to Anderson et al., entitled "Sterile Surgical Adaptor", each of which is incorporated herein by reference in its entirety, and which describe some exemplary sterile barrier and adaptor systems.

A typical installation process for an instrument 150 involves mounting backend mechanism 152 without regard for the orientations of disks 153 on a drive system 140, possibly with an intervening sterile adaptor. The drive motors in drive system 140 may be then be rotated back and forth multiple times during the installation procedure to ensure that the complementary features mesh with and securely engage each other for operation of the newly installed instrument 150. At some point during the installation process, the drive motors become securely engaged to rotate respective disks 153. However, the instrument 150 being installed may move in an unpredictable manner at times during the installation procedure because the drive motors positively engage respective disks 153 of instrument 150 at different and unpredictable times. For certain applications, such unpredictable motion is unacceptable. In general, clear or confined space is required around an instrument 150 to accommodate random movements of the instrument tip during an installation procedure.

SUMMARY

A computer-assisted surgical apparatus includes a preload assembly and a controller. The controller is coupled to the preload assembly. The preload assembly includes a preload engage/disengage mechanism. The controller is configured to move the preload assembly until the preload assembly is fully withdrawn; to activate the preload engage/disengage mechanism if the preload assembly is fully withdrawn; and to move the preload assembly to a home position after activating the preload engage/disengage mechanism.

The apparatus also includes a surgical instrument manipulator assembly that includes the preload assembly, a housing, and a motor pack movably mounted in the housing. The preload assembly includes a cam following assembly that includes a wheel and a body. The wheel is configured to ride on a preload track. The body of the cam following assembly is rotatably coupled to a first pivot pin. The body includes a first and a second end. The second end of the body is coupled to the motor pack. The first end of the body is coupled to the wheel.

In one aspect, the preload engage/disengage mechanism also includes a preload engagement arm that has a first end and a second. The first end of the preload engagement arm is coupled to the first pivot pin. A rolling pin is mounted in the second end of the preload engagement arm.

In this aspect, the preload engage/disengage mechanism further includes a second pivot pin and a preload engage/disengage arm rotatably coupled to the second pivot pin. The preload engage/disengage arm is couplable to and decouplable from the rolling pin. A torsional spring is mounted on the second pivot pin and coupled to the preload engage/disengage arm. The torsional spring is configured to provide a torque on the preload engage/disengage arm to hold the preload engage/disengage arm in a disengaged position from the rolling pin.

The preload engage/disengage mechanism still further includes an electronic actuator coupled to the preload engage/disengage arm and to the controller. If an engage command from the controller is received by the electronic actuator, the electronic actuator provides a torque on the preload engage/disengage arm to hold the preload engage/disengage arm in an engaged position with respect to the rolling pin, this is referred to as the preload being engaged. The preload engage/disengage mechanism also includes an emergency instrument release button coupled to the preload engage/disengage arm.

In another aspect, an apparatus includes a surgical instrument manipulator assembly, an insertion assembly, and a controller. The surgical instrument manipulator assembly includes a housing, a motor pack and a preload assembly. The motor pack is movably mounted in the housing. The preload assembly includes a preload engage/disengage mechanism. The insertion assembly is coupled to the surgical instrument manipulator assembly. The insertion assembly includes a preload track. The controller is coupled to the surgical instrument manipulator assembly, the insertion assembly, and the preload assembly. The controller is configured to command the insertion assembly to move the preload assembly until the preload assembly is fully withdrawn; to command the preload engage/disengage mechanism to engage a preload, if the preload assembly is fully withdrawn; and to command the insertion assembly to move the preload assembly to a home position after engaging the preload. In this apparatus, the preload engage/disengage mechanism is the same as that described above.

A method includes releasing a preload force on a motor pack of a surgical instrument manipulator assembly by moving the surgical instrument manipulator assembly to a fully withdrawn position.

Another method includes moving, by a controller, a surgical instrument manipulator assembly to a fully withdrawn position. The method also includes issuing, by a controller, a command to a preload assembly of the surgical instrument manipulator assembly to engage a preload. The method further includes moving, by the controller, the surgical instrument manipulator assembly to a home position after the preload is engaged. This method can also include moving, by the controller, the surgical instrument manipulator assembly to a fully withdrawn position to automatically release the preload.

A surgical apparatus includes a surgical instrument manipulator assembly and a sterile adapter assembly. The sterile adapter assembly is mounted in the distal face of the surgical instrument manipulator assembly. When the preload assembly configures the surgical instrument manipulator assembly to apply a preload force on the sterile adapter assembly, the sterile adapter assembly is removable from the distal face of the surgical instrument manipulator.

In one aspect, the sterile adapter assembly includes a mechanical sterile adapter assembly removal lockout and a mechanical surgical instrument removal lockout. The surgical apparatus, in one aspect, also includes a surgical instrument is mounted in the sterile adapter assembly. Mounting the surgical instrument in the sterile adapter assembly activates the mechanical sterile adapter assembly removal lockout.

In another aspect, the surgical apparatus also includes an insertion assembly connected to the surgical instrument manipulator assembly. If the surgical instrument manipulator assembly is moved in a distal direction a predetermined distance, the surgical instrument manipulator assembly activates the sterile adapter removal lockout.

In this aspect, the surgical instrument manipulator assembly also includes a clutch button. The clutch button and the emergency release button are the only user operated interfaces of the surgical instrument manipulator assembly.

In one aspect, the sterile adapter assembly includes a frame In this aspect, the mechanical surgical instrument removal lockout includes a movable body moveably mounted in the frame of the sterile adapter assembly. In a first position of the movable body, the surgical instrument can be removed from the sterile adapter assembly, while in a second position of the moveable body, the surgical instrument is locked in place in the sterile adapter assembly.

In yet another aspect, the sterile adapter assembly further includes a beam having a first end and a second end, where the first end is opposite the second end. The beam is pivotally connected to a frame of the sterile adapter assembly. A plurality of hook extensions extends from the second end of the beam. Each of the plurality of hook extension includes a hook configured to engage a hook receiver in a surgical instrument manipulator assembly. A sterile adapter assembly release button is coupled to the first end of the beam. Depressing the sterile adapter assembly release button in a first direction causes the plurality of hook elements to move in a second direction to disengage each hook from the hook receiver. The mechanical sterile adapter assembly removal lockout comprises the first end of the beam where if the surgical instrument is mounted in the sterile adapter assembly, the surgical instrument prevents movement of the sterile adapter assembly button in the first direction and so disables removal of the sterile adapter assembly from the surgical instrument manipulator assembly.

In one aspect, a surgical instrument manipulator assembly includes a housing, a clutch button mounted in the housing, and a preload assembly including an emergency instrument release button. The clutch button and the emergency instrument release button are the only user operated buttons of the surgical instrument manipulator assembly.

A method includes moving a combination of a surgical instrument manipulator assembly and a sterile adapter assembly from a second position where the surgical instrument manipulator assembly exerts a second preload force on the sterile adapter assembly to a first position where the surgical instrument manipulator assembly exerts a first preload force on the sterile adapter assembly, where the second preload force is larger than the first preload force. The method also includes removing the sterile adapter assembly from the surgical instrument manipulator assembly with the first preload force being exerted on the sterile adapter assembly.

In a further aspect, a computer-assisted surgical system includes a surgical instrument manipulator assembly and a controller. The surgical instrument manipulator assembly includes a preload assembly. The controller is coupled to the preload assembly. The controller directly controls the preload provided by the preload mechanism through commands to the preload assembly.

In this aspect the surgical instrument manipulator assembly includes a housing and a motor pack movably mounted in the housing. The preload assembly is connected to the housing. The preload assembly is configured to move the motor pack relative to the housing under control of the controller.

The preload assembly includes a motor and a nut. The motor is coupled to the controller. The nut is coupled to the motor so that the motor moves the nut in a first direction and in a second direction. The preload assembly also includes an arm coupled to the motor pack and a preload release lever pivotally mounted on the arm. The preload release lever is couplable to and decouplable from the nut. If the preload release lever is coupled to the nut, movement of the nut is transferred to the arm. The preload assembly also includes an emergency instrument release button coupled to the preload release lever.

In a still further aspect, a computer-assisted surgical system includes a surgical instrument manipulator assembly, an insertion assembly, and a controller. The surgical instrument manipulator assembly includes a housing, a motor pack, and a preload assembly. The motor pack is movably mounted in the housing. The insertion assembly is coupled to the surgical instrument manipulator assembly to move the surgical instrument manipulator assembly. The controller is coupled to the surgical instrument manipulator assembly, to the insertion assembly, and to the preload assembly. The controller is configured to command the preload assembly to change a position of the motor pack with respect to housing of the motor pack independent of the position of the insertion assembly relative to the preload assembly and independent of whether the insertion assembly is moving or stationary.

Another method includes controlling a preload force on a motor pack of a surgical instrument manipulator assembly by a controller issuing a command directly to a preload assembly.

Yet another method includes moving, by a controller, a motor pack of a surgical instrument manipulator assembly relative to a housing of the surgical instrument manipulator assembly from a no preload position to a low preload position while the surgical instrument manipulator assembly remains at a fixed position, such as the home position. This method further includes moving, by the controller, the motor pack of a surgical instrument manipulator assembly relative to a housing of the surgical instrument manipulator assembly from a high preload position to a low preload position irrespective of control of an insertion assembly on which the surgical instrument manipulator is mounted.

BRIEF DESCRIPTION OF THE DRAWINGS

FIGS. 4A to 4G are block diagrams that illustrate the mounting of a sterile adapter assembly and an instrument on an instrument manipulator assembly, operation of a preload mechanism, instrument removal lockout, sterile adapter removal lockout, automatic preload release, and automatic preload reset.

FIG. 9A illustrates the instrument manipulator assembly of FIG. 2 affixed to an insertion assembly that in turn is attached to an insertion axis base assembly.

FIGS. 9B to 9F are illustrations of a sterile adapter assembly that includes mechanical lockouts.

FIGS. 10A and 10B illustrate installing the sterile adapter assembly of FIGS. 9B to 9F on another instrument manipulator assembly.

FIG. 10C is a partial cutaway drawing that illustrates features of the sterile adapter assembly and the instrument manipulator assembly.

FIGS. 11A and 11B are more detailed illustrations of an example of one of the instruments of FIG. 2.

FIGS. 12 to 14 illustrate stages in the mounting of the instrument in the sterile adapter assembly.

FIGS. 17A and 17B illustrate a preload assembly in greater detail.

FIG. 17C is a side view of a torsional spring in the preload assembly of FIGS. 17A and 17B.

FIGS. 18A to 18E illustrate the automatic engagement of the preload by a controller.

FIGS. 19A to 19C illustrate the automatic disengagement of the preload by the controller.

Figure 1A:
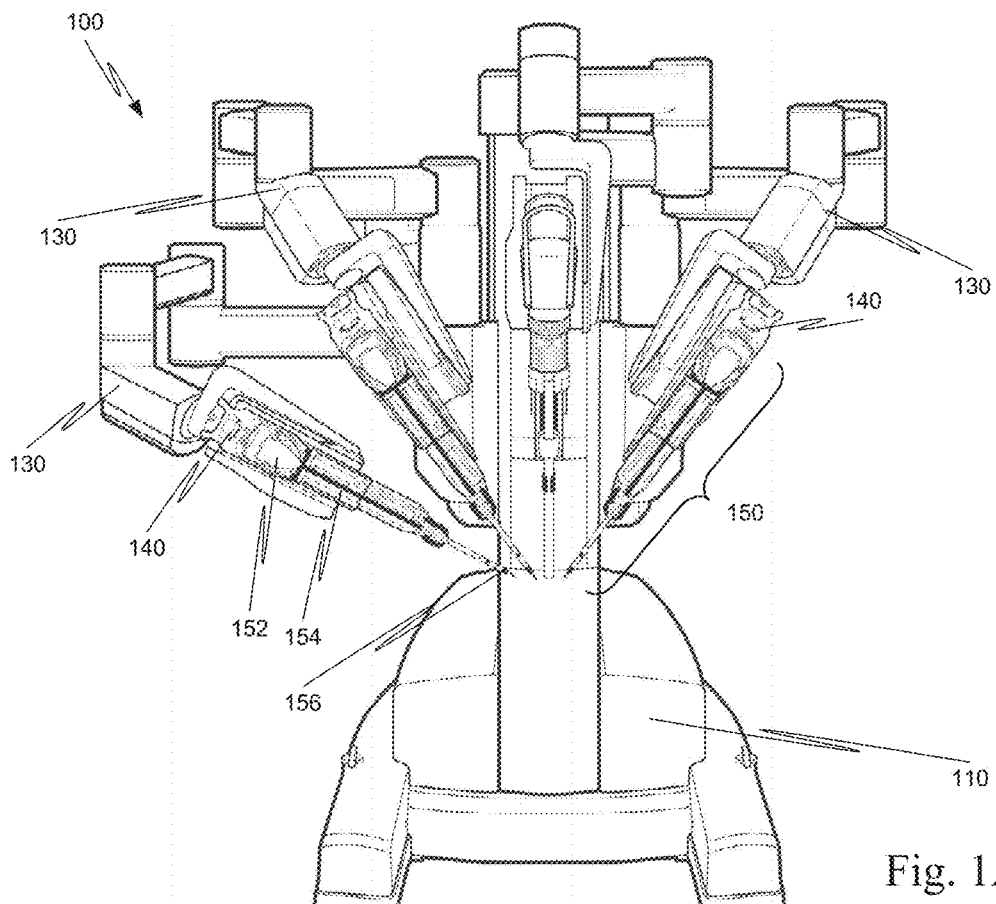
FIG. 1A is an illustration of a prior art teleoperated minimally invasive surgical system.
Figure 1B:
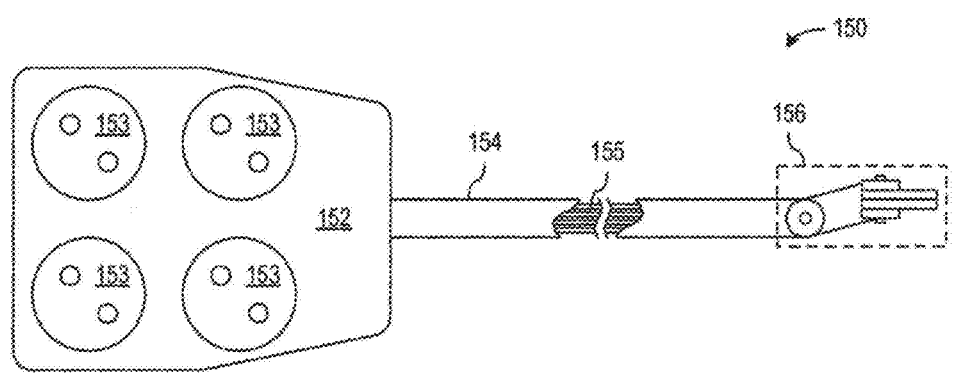
FIG. 1B is an illustration of a prior art surgical device assembly.

In the drawings, for single digit figure numbers, the first digit in the reference numeral of an element is the number of the figure in which that element first appears. For double-digit figure numbers, the first two digits in the reference numeral of an element is the number of the figure in which that element first appears.

DETAILED DESCRIPTION

In one aspect, a computer-assisted teleoperated system 200, sometimes referred to as system 200, (FIG. 2), e.g., a minimally invasive computer-assisted teleoperated system, includes a patient-side support system 210 having an arm 220. At an end of arm 220 is an entry guide manipulator assembly 230 (also called entry guide manipulator 230). Mounted on entry guide manipulator 230 is a master instrument manipulator 280 that in turn supports multiple surgical device assemblies. In one aspect, a surgical device assembly includes an instrument manipulator assembly 240, an instrument sterile adapter assembly 250, and an instrument 260. In one aspect, instrument sterile adapter assembly 250 is attached to a sterile drape that is used to drape entry guide manipulator 230 and each instrument manipulator assembly 240.

Instrument manipulator assembly 240 is sometimes referred to as instrument manipulator assembly 240. Instrument sterile adapter assembly 250 is sometimes referred to as sterile adapter assembly 250.

Entry guide manipulator 230 changes the pitch and yaw of the surgical device assemblies as group. A main tube of each instrument 260 extends through a different channel in a single port entry guide 270. Single port entry guide 270 is mounted in a cannula, in this aspect. Single port refers to a single access location (e.g., a single incision, a single natural orifice, and the like) to a surgical site inside the patient.

As used herein, a cannula is a tube that passes through the patient's body wall, and that comes in direct contact with the patient. The cannula generally does not slide in and out relative to the patient, but the cannula can pitch and yaw around a point on its axis called the remote center of motion.

As used herein, singe port entry guide 270 is a tube through which all surgical instruments and a camera instrument must pass to reach a location inside the patient. Entry guide 270 has separate lumens for each instrument. Entry guide 270 passes through the cannula, and may twist relative to the cannula.

A controller 290 is coupled to a surgeon's control console (not shown) and to patient-side support system 210. Controller 290 represents the various controllers in system 200. Controller 290 sends second control commands to instrument 260 in response to first control commands. The first control commands are based on movements of masters in a surgeon's control console by a surgeon. A display control module in system controller 290 also updates a stereoscopic view of the surgical site generated by a display device in the surgeon's control console as slave instrument 260 moves in response to the second control commands.

Although described as controller 290, it is to be appreciated that controller 290 may be implemented in practice by any combination of hardware, software that is executed on a processor, and firmware. Also, its functions, as described herein, may be performed by one unit or divided up among different components, each of which may be implemented in turn by any combination of hardware, software that is executed on a processor, and firmware. When divided up among different components, the components may be centralized in one location or distributed across system 200 for distributed processing purposes. A processor should be understood to include at least a logic unit and a memory associated with the logic unit.

As explained more completely below, in one aspect, controller 290 releases a preload force on a motor pack of instrument manipulator assembly 240 by moving the instrument manipulator assembly 240 to a fully withdrawn position, which is proximal to the home position.

To engage the preload, controller 290 moves instrument manipulator assembly 240 to a fully withdrawn position, and then controller 290 issues a command to a preload assembly of instrument manipulator assembly 240 to engage the preload. After the preload is engaged, controller 290 moves instrument manipulator assembly 240 to a home position. Here, when it is stated that controller 290 preforms an act, it means that controller issues a command or signal to a component that performs the act.

In another aspect, controller 290 can change the preload independent of the position of instrument manipulator assembly 240 and independent of whether instrument manipulator assembly 240 is moving or stationary. Controller 290 controls a motor within the preload assembly that in turn determines the preload applied by the preload assembly. Commands from controller 290 to the insertion assembly to move instrument manipulator assembly 240 do not affect the preload in this aspect. The preload is under the direct control of controller 290, and can be changed by controller 290 as necessary.

As described more completely below, computer-assisted teleoperated system 200 includes some features of a previous system, which are presented in:

U.S. Patent Application Publication No. US 2016/0184037 A1 (disclosing "PRELOADED SURGICAL INSTRUMENT INTERFACE");

U.S. Patent Application Publication No. US 2016/0184036 A1 (disclosing "VARIABLE INSTRUMENT PRELOAD MECHANISM CONTROLLER");

U.S. Patent Application Publication No. US 2016/0184035 A1 (disclosing "ACTUATOR INTERFACE TO INSTRUMENT STERILE ADAPTER");

PCT International Publication No. WO 2015/023834 A1 (disclosing "INSTRUMENT STERILE ADAPTER DRIVE FEATURES");

PCT International Publication No. WO 2015/023840 A1 (disclosing "INSTRUMENT STERILE ADAPTER DRIVE INTERFACE"); and PCT International Publication No. WO 2015/023853 A1 (disclosing "ROBOTIC INSTRUMENT DRIVEN ELEMENT"), each of which is incorporated herein by reference in its entirety.

The features common to both the prior system and system 200 are not described in detail herein to avoid detracting from the inventive aspects described herein.

In one aspect of the system described in the above cited publications, each instrument manipulator assembly included a sterile adapter release latch, a clutch button, and a preload release button. As explained more completely, the instrument manipulator assemblies in system 200 do not include a sterile adapter release latch or a pre-load based sterile adapter release lock-out.

Instrument manipulator assembly 240 includes a clutch button mounted in the housing of instrument manipulator assembly 240 and an emergency instrument release button. The clutch button and the emergency release button are the only user operated buttons of instrument manipulator assembly 240. Thus, the clutch button and the emergency release button are the only user operated interfaces of the instrument manipulator assembly 240. The reduction in the number of buttons on instrument manipulator assembly 240 improves the user experience by minimizing the likelihood that a user mistakenly presses the wrong button or delays at a critical time due to confusion about the function of the various buttons on instrument manipulator assembly 240.

In one aspect of the system described in the above cited publications, the preload release button had a dual function. The preload release button was pushed to defeat a sterile adapter removal lockout feature so that the sterile adapter could be removed. The preload release button also was used to release the preload in an emergency situation. In contrast, as explained more completely below, the emergency instrument release button on each of the plurality of instrument manipulators of system 200 is used only to release a preload force on a disk stack. In addition, to facilitate the draping of system 200, the release of the preload and activation of the preload is under the control of controller 290 so that the preload can be released to facilitate the draping process and can be activated after draping is completed.

Figures 3A, 3B:
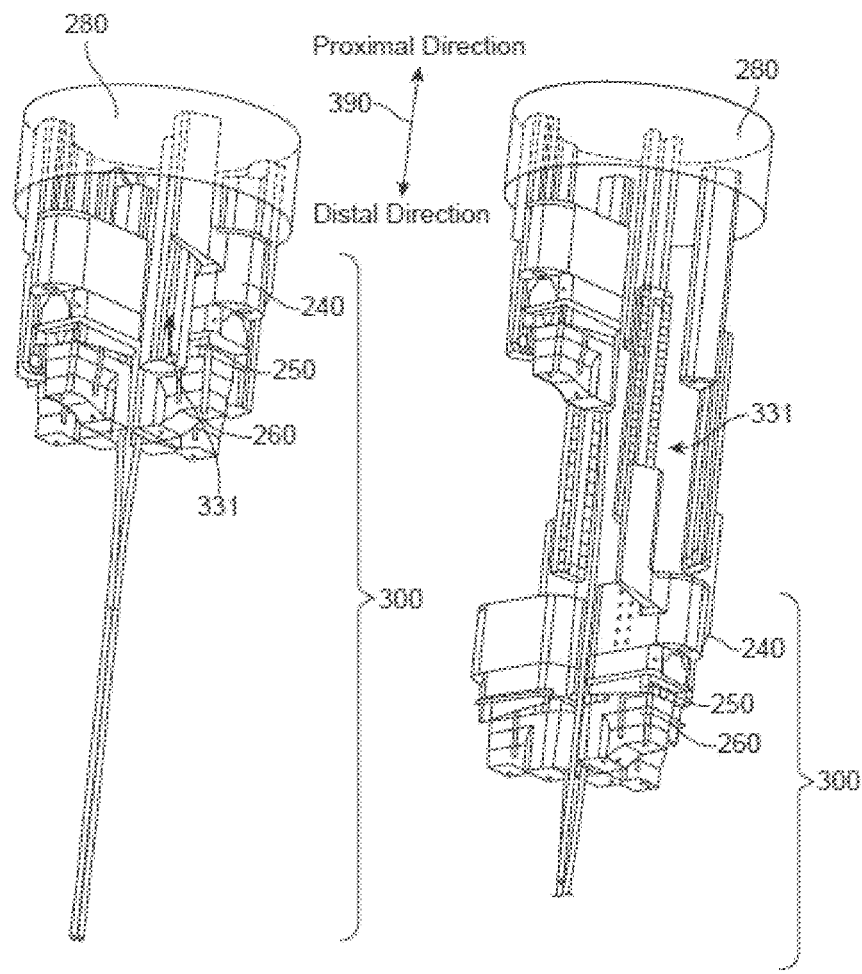
FIG. 3A is a more detailed illustration of the configuration of the surgical device assemblies in FIG. 2, with all the assemblies at a home position.
FIG. 3B is a more detailed illustration of the configuration of the surgical device assemblies in FIG. 2, with some of the assemblies at an extended position.

FIGS. 3A and 3B are illustrations of four surgical device assemblies 300 mounted on entry guide manipulator 230. In FIG. 3A, surgical device assemblies 300 are positioned at an initial position, e.g., a first location, sometimes referred to as the "home position." The mechanical interface includes a disk stack between a motor in instrument manipulator assembly 240 and a shaft in the transmission unit of instrument 260. In the configuration of FIG. 3A, following draping, a first preload force is applied on the disk stack, e.g., a first predetermined force is applied on the disk stack.

With this first preload force, the mechanical interface may have some backlash because the first preload force is not sufficient to clamp the disks in the disk stack tightly enough together to prevent relative motion between the disks in the mechanical interface. However, the design of disks in the disk stack in the mechanical interface in combination with the first preload force ensures that the disks in the disk stack remain engaged, e.g., partially coupled, until the backlash is minimized.

With the first preload force, which is a low preload force, the disks in the mechanical interface have zero backlash up to a first torque level, e.g., 1.17 in-lb assuming a friction coefficient of 0.1. Above the first torque level, there may be a known small backlash, for example 1.13 degrees. Since, as described more completely below, a force sufficient to spin the disks to overcome friction and dynamically mate the disks quickly is used, this force typically provides more than the first torque level. In this instance, the disks in the mechanical interface have non-zero backlash. Thus, the mechanical interface is said to have non-zero backlash in this instance.

In FIG. 3B, three of the four surgical device assemblies have been moved distally. Arrow 390 defines the distal and proximal directions. Here, the distal direction is towards patient 201 and away from master instrument manipulator 280. The proximal direction is away from patient 201 and towards master instrument manipulator 280. The distal direction is an example of a first direction and the proximal direction is an example of a second direction that is opposite to the first direction.

As surgical device assembly 300 moves distally on insertion assembly 331, the preload force on the disk stack is automatically increased from the first preload force to a second preload force. The second preload force is an example of a second predetermined force. The second preload force reduces the backlash of the mechanical interface, i.e., the backlash between the disks in the disk stack, to zero for torque levels used in surgical procedures.

In one aspect, the second preload force is a high preload force, e.g., 2.3 lb. As just described, the disks in the mechanical interface, and hence the mechanical interface, have zero backlash at torque levels used in surgical procedures. In one example if the coefficient of friction is assumed to be 0.1, the mechanical interface has zero backlash for torque levels up to 4.9 in-lb. For instrument 260 to apply surgically useful forces at the end effector, a certain torque must be applied to the disks in the mechanical interface. This is deemed a surgically useful torque. In one example, a surgically useful torque may be 4.425 in-lb, and so the mechanical interface has zero backlash for torque levels used in surgical procedures in this aspect.

FIGS. 4A to 4G are block diagrams that illustrate the mounting of a sterile adapter assembly and an instrument on an instrument manipulator assembly. Other aspects illustrated in FIGS. 4A to 4G include operation of a preload engage/disengage mechanism to reduce backlash, instrument removal lockout, sterile adapter assembly removal lockout, preload release, and automatic preload reset. These mechanical lockout features are used to assure that system 200 cannot have illegal transitions between the different states of system 200.

Figure 4A:
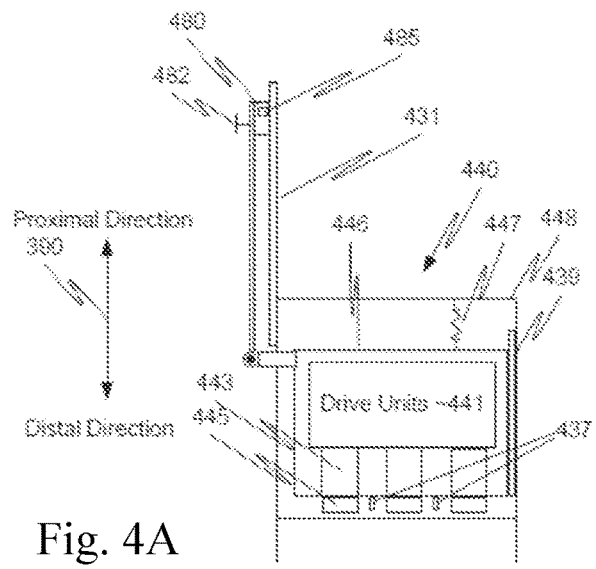

FIGS. 4A to 4G are not to scale. Arrow 390 in FIGS. 4A and 4G shows the proximal and distal directions in each of FIGS. 4A to 4G.

FIG. 4A shows an instrument manipulator assembly 440 affixed to insertion assembly 431. Instrument manipulator assembly 440 is one example of instrument manipulator assembly 240. Insertion assembly 431 is an example of insertion assembly 331.

Instrument manipulator assembly housing 448, sometimes referred to as housing 448, is fixedly attached to a distal end of insertion assembly 431, and so instrument manipulator assembly housing 448 moves with movement of insertion assembly 431. However, a motor pack 446 within instrument manipulator assembly housing 448 can move on rail 439. Motor pack 446 can move in the distal and proximal directions relative to instrument manipulator assembly housing 448. Motor pack 446 is coupled to instrument manipulator assembly housing 448 by a motor pack return spring 447, sometimes referred to as return spring 447.

Motor pack 446 is movably coupled to insertion assembly 431 by preload assembly 480. Preload assembly 480 rides on a preload track in insertion assembly 431, in one aspect. As explained more completely below, as preload assembly 480 moves in the distal direction, preload assembly 480 provides a longitudinal force in the distal direction on motor pack 446. Preload assembly 480 includes an emergency instrument release button 482.

Motor pack 446 includes a plurality of drive units 441. Plurality of drive units 441 includes a plurality of drive motors and a plurality of drive output assemblies. Each drive motor in the plurality of drive motors is coupled to a corresponding drive output assembly 443 in the plurality of drive output assemblies.

Drive output assembly 443 includes a preload spring assembly and a drive output disk 445. Drive output assembly 443 also includes a low backlash coupler positioned between the preload spring assembly and drive output disk 445. Drive output disk 445 is coupled to the low backlash coupler by a set of input pins.

Drive output disk 445 is a cylindrical disk that includes a distal end surface. The distal end of each drive output disk 445 has a drive interface. The drive interface includes drive dogs and alignment elements. The drive dogs extend in a distal direction from the distal end surface. An example of a motor pack and a plurality of drive units suitable for use as motor pack 446 including a plurality of drive units 441 are described in U.S. Patent Application Publication No. US 2016/0184037 A1 (disclosing "PRELOADED SURGICAL INSTRUMENT INTERFACE"), which was previously incorporated by reference;

Motor pack 446 includes a plurality of hard-stops 437. Each of the plurality of hard-stops 437 is configured to extend from a distal face of motor pack 446 when there is a high preload on motor pack 446.

FIG. 4A shows instrument manipulator assembly 440 with motor pack 446 at a no preload position 432, i.e., with the preload mechanism released. In this configuration, if the preload mechanism is not engaged, e.g., the preload is not engaged, there is no preload on motor pack 446 so that the plurality of drive output disks including drive output disk 445 do not extend from a distal face of instrument manipulator assembly housing 448 irrespective of the position of instrument manipulator assembly 440 with respect to the home position. The distal face of motor pack 446 is at no preload position 432. Conversely, if the preload mechanism is engaged and instrument manipulator assembly 440 is at a home position, there is a first preload force on motor pack 446 so that the plurality of drive output disks including drive output disk 445 extend from a distal face of instrument manipulator assembly housing 448. The occurs when motor pack is at a low preload position 433 relative to instrument manipulator assembly housing 448.

Typically, prior to use, at least a portion of patient side support system 210 is draped with a sterile surgical drape prior to using system 200. Prior to considering the mechanical lockout safety features of system 200, as presented in FIGS. 4B to 4G, it is helpful to consider aspects of patient side support system 210 and a sterile surgical drape, because some of the control states of instrument manipulator assembly 440 are dependent upon signals provided during the draping process.

Figure 5:
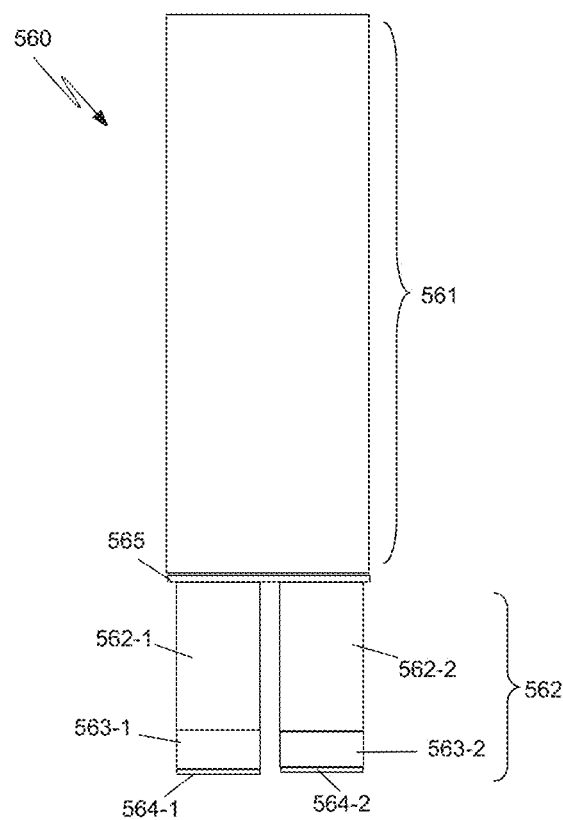
FIG. 5 illustrates a sterile surgical drape.

In one aspect, a sterile surgical drape 560 (FIG. 5), sometimes referred to as surgical drape 560, is use to drape a portion of patient side support system 210. In one aspect, sterile surgical drape 560 includes a first portion 561 and a second portion 562.

First portion 561 of sterile surgical drape 560 is connected to a stationary part of a rotatable seal 565 and second portion 562 is connected to a movable part of rotatable seal 565. In one aspect, rotatable seal 565 is labyrinth seal, where the stationary part is a roll cover portion of the labyrinth seal, and the movable part is a base comb portion of the labyrinth seal.

Second portion 562 of sterile surgical drape 560, in one aspect, includes a plurality of drape sleeves 562-1, 562-2, a plurality of boots 563-1, 563-2, and a plurality of mechanical interface elements 564-1, 564-2. Typically, sterile surgical drape 560 includes one drape sleeve, one boot, and one mechanical interface element for each instrument manipulator assembly 240 in system 200.

Each of plurality of mechanical interface elements 564-1, 564-2 is coupled to a corresponding boot in plurality of boots 563-1, 563-2. Each of plurality of boots 563-1, 563-2 is coupled to a corresponding drape sleeve in plurality of drape sleeves 562-1, 562-2. An opening of each drape sleeve in plurality of drape sleeves 562-1, 562-2 is connected to the movable portion of rotatable seal 565, which, in one aspect, is a disc with ribs that form a plurality of wedge-shaped "frames" with apertures, each of the frames is sized to circumscribe an instrument manipulator assembly. The open end of each of plurality of drape sleeves 562-1, 562-2 is coupled to a different one of the plurality of wedge-shaped frames. Each of plurality of boots 563-1, 563-2 fits around an instrument manipulator assembly that is coupled by an insertion assembly to an entry guide manipulator assembly.

Figure 2:
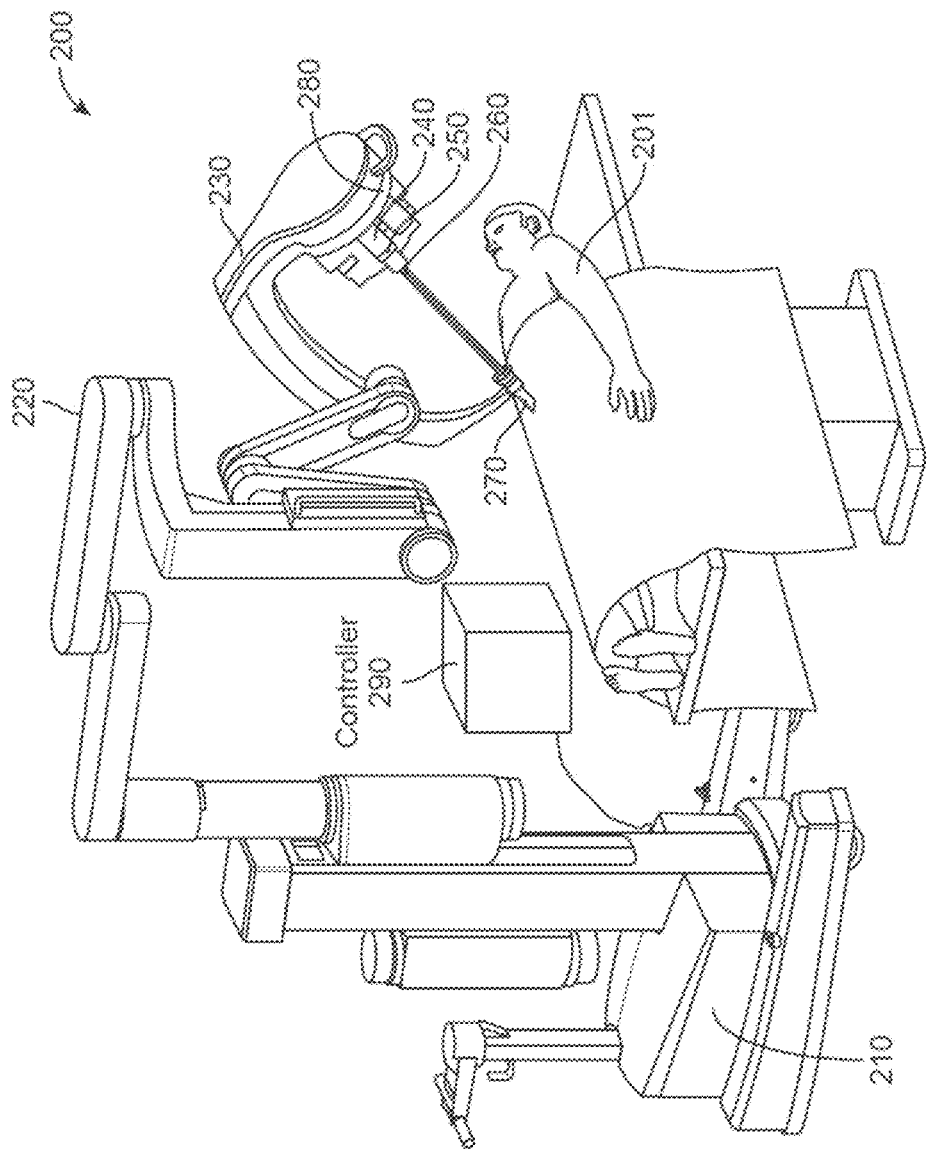
FIG. 2 is an illustration of a teleoperated system that includes an instrument manipulator assembly with a preload assembly that includes automated preload engagement/disengagement and only an emergency instrument release button and a clutch button.
Figure 6A:
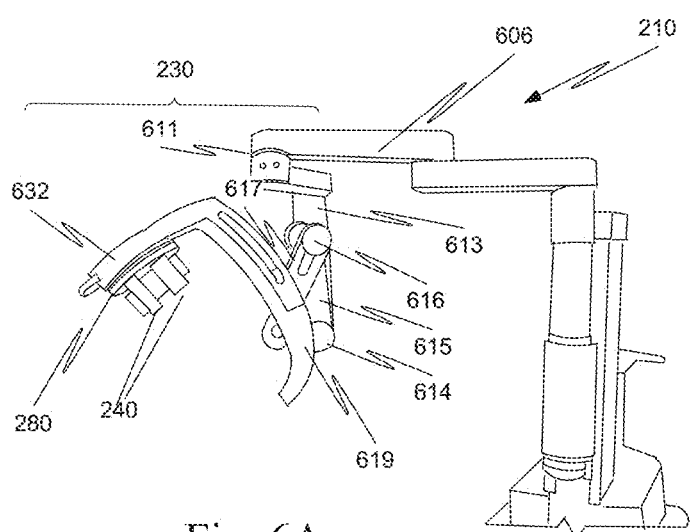
FIG. 6A is an illustration of the patient side support system of FIG. 2A in a configuration for draping.

FIG. 6A is an illustration of one aspect of a patient side support system 210 in a configuration to initiate draping. As illustrated in FIGS. 2 and 6A, entry guide manipulator assembly 230, sometimes referred to as entry guide manipulator 230, includes four links 613, 615, 617, and 619 coupled by joints. As shown in FIG. 6A, a manipulator assembly yaw joint 611 is coupled between an end of setup link 606 and a second end, e.g., a proximal end, of a first manipulator link 613. Yaw joint 611 allows first manipulator link 613 to move with reference to link 606 in a motion that may be arbitrarily defined as "yaw" around a manipulator assembly yaw axis.

In one embodiment, setup link 606 is rotatable in a horizontal or x, y plane and yaw joint 611 is configured to allow first manipulator link 613 in entry guide manipulator 230 to rotate about a yaw axis. Setup link 606, yaw joint 611, and first manipulator link 613 provide a constantly vertical yaw axis for entry guide manipulator 230.

A first end of first manipulator link 613 is coupled to a second end of a second manipulator link 615 by a first actively controlled rotational joint 614. A first end of second manipulator link 615 is coupled to a second end of a third manipulator link 617 by a second actively controlled rotational joint 616. A first end of third manipulator link 617 is coupled to a distal portion of a fourth manipulator link 619 by a third actively controlled rotational joint.

In one embodiment, links 615, 617, and 619 are coupled together to act as a coupled motion mechanism. Coupled motion mechanisms are well known (e.g., such mechanisms are known as parallel motion linkages when input and output link motions are kept parallel to each other). For example, if rotational joint 614 is actively rotated, joints 616 and 618 are also actively rotated so that link 619 moves with a constant relationship to link 615. Therefore, it can be seen that the rotational axes of joints 614, 616, and 618 are parallel. When these axes are perpendicular to the rotational axis of joint 611, links 615, 617, and 619 move with reference to link 613 in a motion that may be arbitrarily defined as "pitch" around a manipulator assembly pitch axis. Since links 615, 617, and 619 move as a single assembly, first manipulator link 613 may be considered an active proximal manipulator link, and second through fourth manipulator links 615, 617, and 619 may be considered collectively an active distal manipulator link.

Figure 6B:
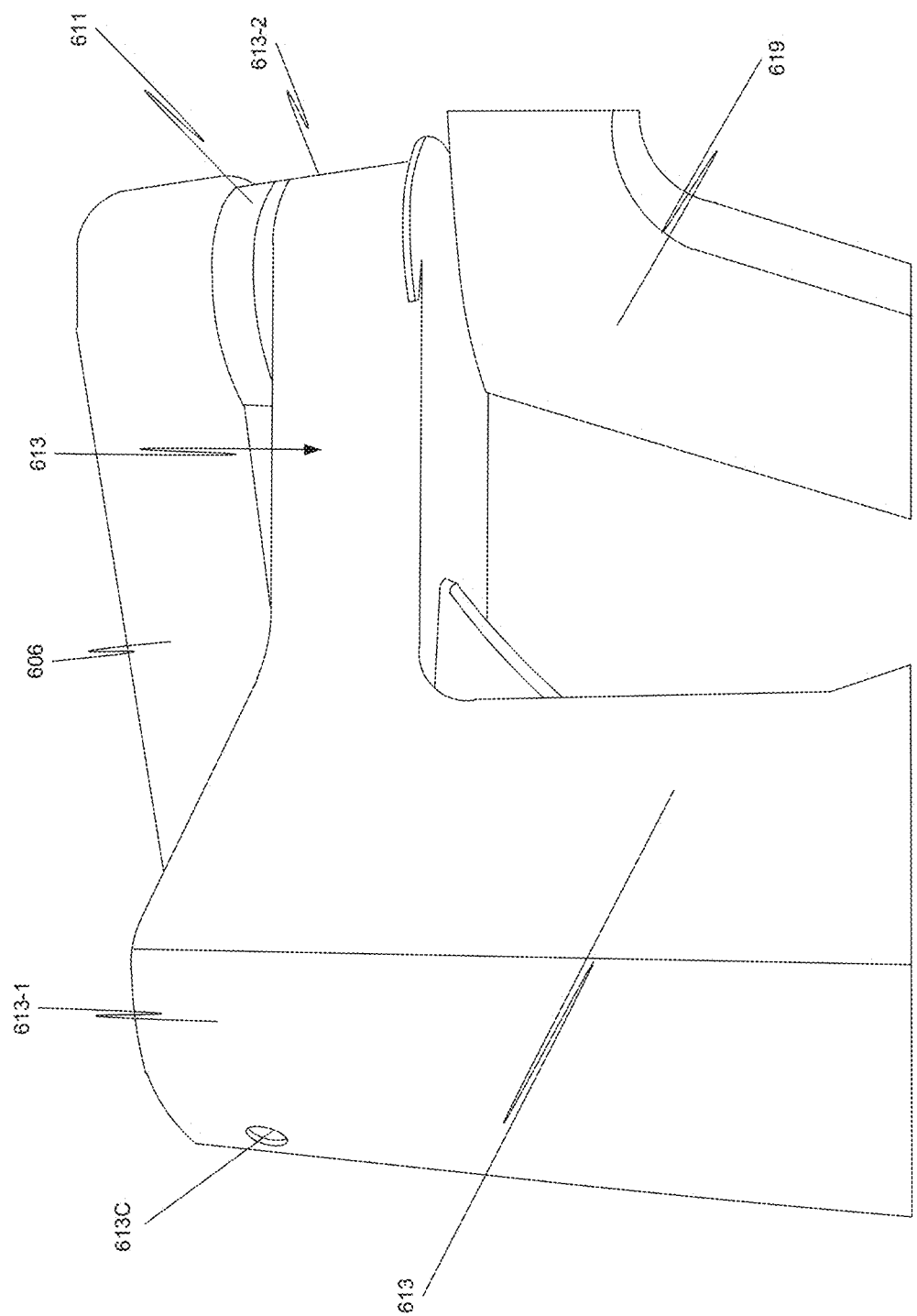
FIGS. 6B and 6C illustrate drape alignment and mounting receptacles on a link of the patient side support system.
Figure 6C:
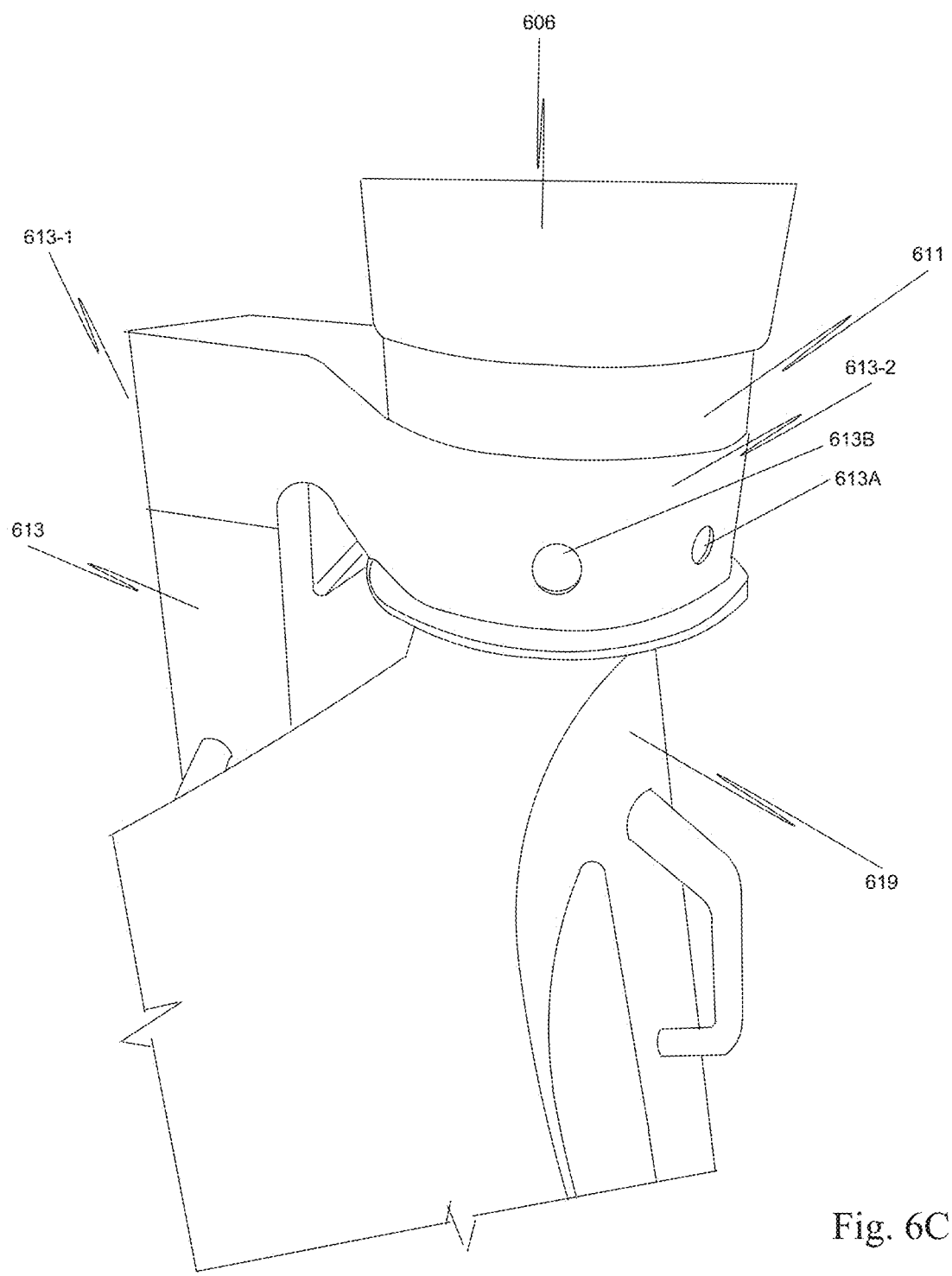

In one aspect, a first manipulator link 613 includes a first end 613-1 (FIG. 6B) that includes an alignment receptacle 613C and a second end 613-2 (FIG. 6C) that includes two alignment receptacles 613A, 613B. Attachment devices—one for each of the alignment receptacles—are affixed to surgical drape 560. In one aspect, each of alignment receptacles 613A, 613B, 613C includes a magnet and the attachment devices affixed to surgical drape 560 are shaped to fit in alignment receptacles 613A, 613B, 613C, and are made of a metal that is attracted to and couples with the magnet.

In one aspect, each of alignment receptacles 613A, 613B, 613C includes an attachment senor or has an attachment sensor associated with the alignment receptacle. When the attachment sensors detect that surgical drape 560 has been attached to patient side support system 210, a drape attached signal is sent to controller 290 indicating the attachment of surgical drape 560. Specifically, when an attachment device attached to surgical drape 560 is engaged with the corresponding alignment receptacle to attach surgical drape 560 to a portion of patient side support system 210, the attachment sensor detects the presence of the attachment device.

A sensor configured to detect the presence of a drape attachment device may be, for example, an inductive sensor. An inductive sensor emits a magnetic field that is sensed by the sensor, such as via an induction loop. When a metallic member, i.e., the attachment device, is proximate the sensor, the metallic member changes the inductance, which is detected by the sensor to indicate the presence of the attachment device. The use of an inductive sensor is illustrative only and is not intended to be limiting.

A sensor to detect the attachment of surgical drape 560 may be, for example, an optical sensor. An optical sensor may use, for example, light reflected off the drape attachment device or light reflected off drape 560 itself to detect when surgical drape 560 has been attached. In another example, an optical sensor may be a sensor that emits a light beam and receives the light beam, but senses the presence of surgical drape 560 when the surgical drape 560 or the attachment device breaks the beam. A sensor may also be a capacitive sensor that senses a change in capacitance that occurs when surgical drape 560 has been attached. In another example, a sensor may be a switch that is mechanically depressed or otherwise switched by the drape attachment device or surgical drape 560 when surgical drape 560 is attached to link 613 of patient side support system 210.

Figure 7A:
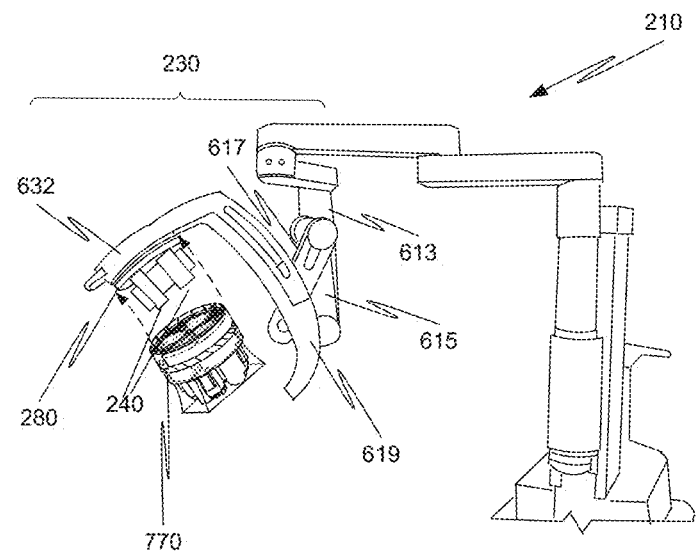
FIG. 7A illustrates a surgical drape installation package being moved into position for mounting on a platform on one end of a link of the patient side support system.

FIG. 7A illustrates a surgical drape installation package 770 being moved into position for mounting on platform 632 on one end of link 619. Surgical drape installation package 770 includes a surgical drape installation aid on which sterile surgical drape 560 is mounted.

Figure 7B:
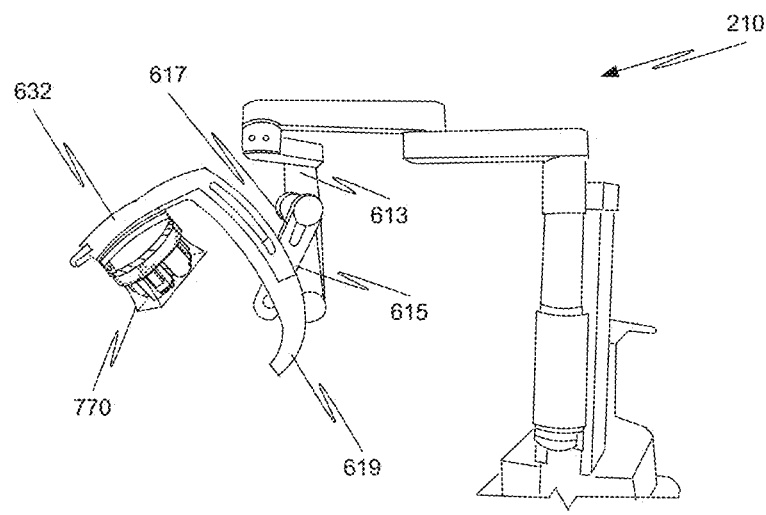
FIG. 7B shows the surgical drape installation package mounted on the platform of FIG. 7A.

FIG. 7B shows surgical drape installation package 770 mounted on platform 632. In particular, each of a plurality of latches of rotatable seal 565 has been engaged in a corresponding latch receptacle in platform 632. An example of a surgical drape installation package is presented in commonly assigned and commonly filed U.S. Patent Application No. 62/362,190 (disclosing "Surgical Drape Installation Aid," filed Jul. 14, 2016), which is incorporated herein by reference in its entirety.

When surgical drape installation package 770 is mounted on platform 632, a drape mount sensor sends a drape mounted signal to controller 290 indicating the mounting of surgical drape installation package 770. In one aspect, the drape mount sensor includes a mechanical switch, e.g., a plunger, which is activated by mounting of the stationary part of a rotatable seal 565. Alternatively, instead of a mechanical sensor, the drape mount sensor could be an inductive sensor, a capacitive sensor, or an optical sensor similar to those described above.

Figure 8:
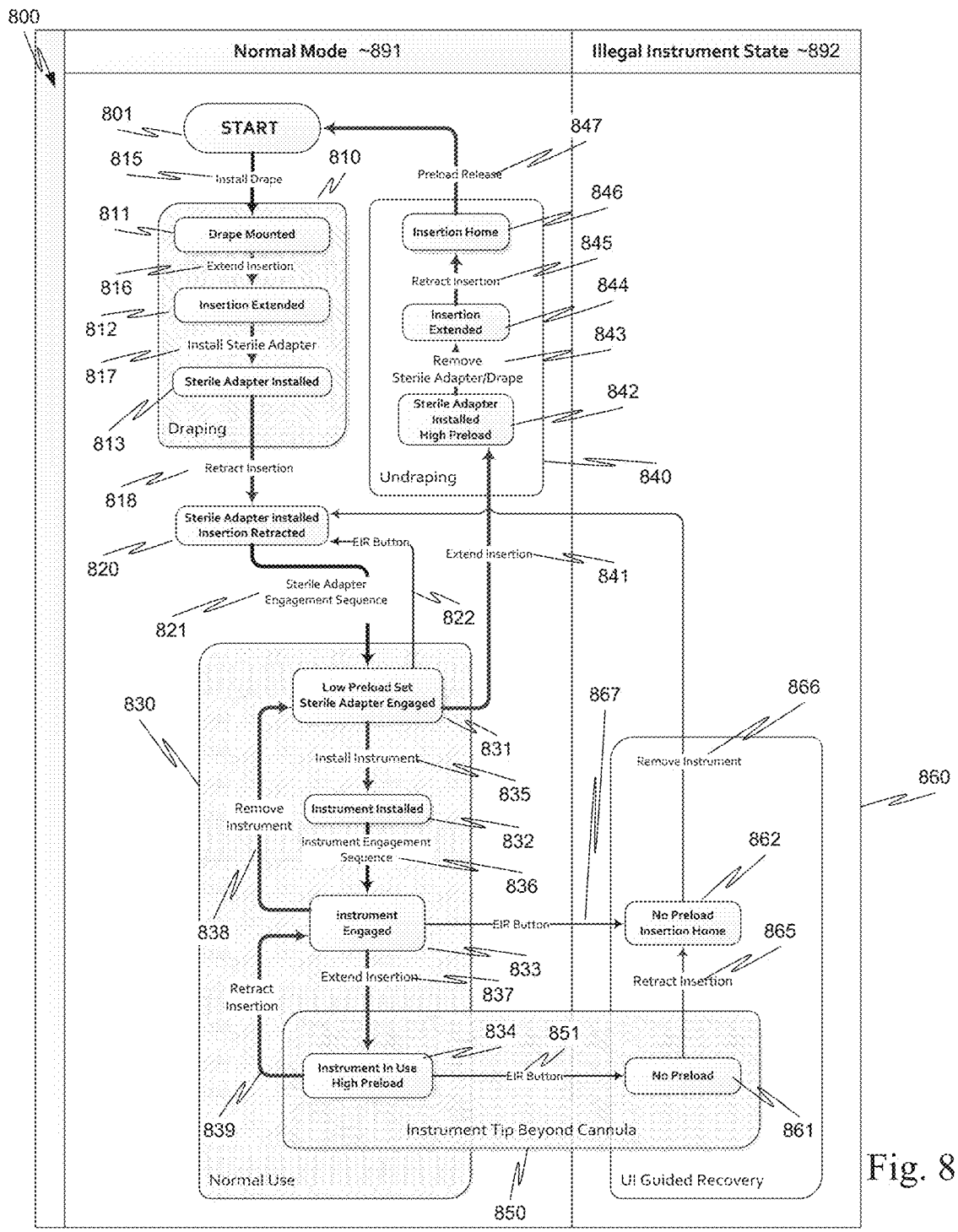
FIG. 8 is a state diagram for an instrument manipulator assembly.

Returning to the consideration of FIGS. 4B to 4G, these figures are described in combination with state workflow diagram 800 (FIG. 8) of instrument manipulator assembly 240 and instrument manipulator assembly 440. In FIG. 8, the different states in workflow diagram 800 are divided into a NORMAL MODE 891 and an ILLEGAL STATE MODE 892. The normal path between states is indicated by the heavy solid line in FIG. 8.

In START state 801 for instrument manipulator assembly 440 of computer-assisted teleoperated system 200, the preload engage/disengage mechanism of preload assembly 480 is disengaged. Thus, there are no preload forces on the drive disks of motor pack 446, e.g., motor pack 446 is at no preload position 432 relative to instrument manipulator housing 448. Also, in START state 801, instrument manipulator assembly 440 (FIG. 4A) is moved so that instrument manipulator assembly 440 is at a home position, if instrument manipulator assembly 440 is not already at that position. Hence, in START state 801 the preload engage/disengage mechanism is not activated, and so as instrument manipulator assembly 440 is moved by insertion assembly 431, no pre-load forces are created.

In response to a command from a user interface to deploy for draping, INSTALL DRAPE act 815 is initiated. In INSTALL DRAPE act 815, entry guide manipulator 230 is moved by controller 290 to the position shown in FIG. 6A, and master instrument manipulator 280 moves the plurality of instrument manipulator assemblies as far apart as possible to facilitate draping. Next, surgical drape installation package 770 is mounted on entry guide manipulator assembly platform 632, and in response to the mounting of package 770, a drape mounted signal is sent to controller 290.

First portion 561 of sterile surgical drape 560 is extended over links 619, 617, and 615 of entry guide manipulator 230. Finally, first portion 561 is attached to alignment receptacles 613A, 613B, and 613C of link 613. As explained above, the attachment of sterile drape 560 to link 613 causes a drape attached signal to be sent to controller 290. Upon completion of draping the links of entry guide manipulator 230, the user typically moves entry guide manipulator 230 from the tilted position shown in FIGS. 7A and 7B back to the vertical position.

When controller 290 receives the drape attached signal after receiving the drape mounted signal, the state of instrument manipulator assembly 440 transitions from START state 801 to DRAPE MOUNTED state 811, sometime referred to as state 811, in DRAPING process 810. When state 811 is entered, instrument manipulator assembly 440 is configured so that if a user pushes on instrument manipulator assembly 440, instrument manipulator assembly 440 automatically moves in the direction of the force applied by the user. This helps the user to position a sleeve of sterile drape 560 around insertion assembly 431 and instrument manipulator assembly 440.

Thus, in EXTEND INSERTION act 816, a user pushes instrument manipulator assembly 440 in the distal direction. In response to the force supplied by the user, controller 290 causes insertion assembly 430 to move instrument manipulator assembly 440 in the distal direction. One example of a controller that moves an instrument manipulator in response to a user tap is described in commonly assigned and commonly filed U.S. Patent Application No. 62/362,192 (disclosing "Automatic Manipulator Assembly Deployment for Draping," filed Jul. 14, 2016), which is incorporated herein by reference in its entirety. After insertion assembly 431 is extended, DRAPE MOUNTED state 811 transfers to INSERTION EXTENDED state 812. Even though insertion assembly 431 is extended, there are no preload actions, because the preload engage/disengage mechanism of preload assembly 480 is disengaged.

Figure 4B:
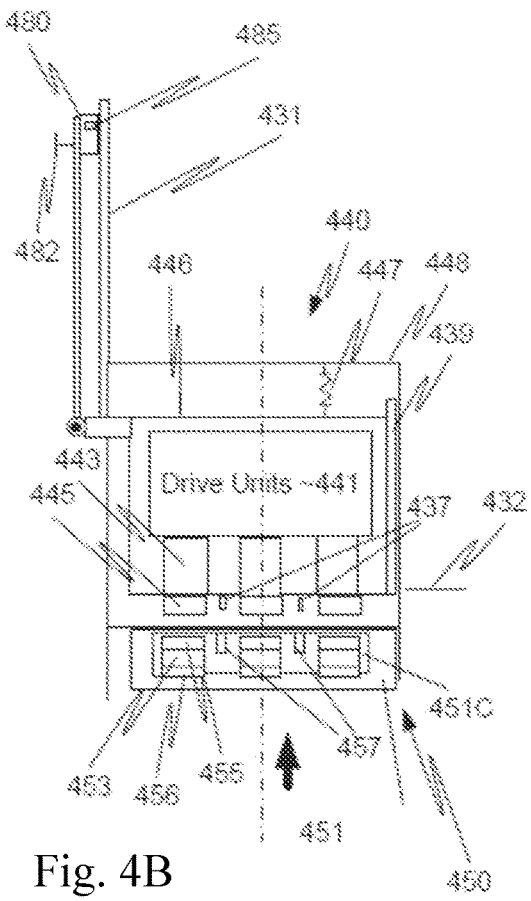

With instrument manipulator assembly 440 in INSERTION EXTENDED state 812, in INSTALL STERILE ADAPTER act 817, a surgical device interface element 450, e.g., a sterile adapter assembly, is mounted on instrument manipulator assembly 440 to obtain the configuration shown in FIG. 4B. Surgical device interface element 450 is an example of sterile adapter assembly 250. Since the preload engage/disengage mechanism is not engaged, motor pack 446 is not displaced distally with respect to housing 448, and so mounting surgical device interface element 450 in this configuration does not requires compressing the plurality of preload spring assemblies including the preload spring assembly in drive output assembly 443 during the mounting of surgical device interface element 450.

With no preload force on motor pack 446, surgical device interface element 450 is mounted by moving surgical device interface element 450 proximally until hooks on surgical device interface element 450 engage hook receivers in instrument manipulator assembly 440. Unlike the prior art surgical device interface element that required placing one end of the surgical device interface element in the instrument manipulator assembly and pivoting the opposite end of the surgical device interface element until it was latched, surgical device interface element 450 is moved in a direction perpendicular to a distal face of instrument manipulator assembly 440. The mounting of surgical device interface element 450 causes a sensor to send a sterile adapter mounted signal to controller 290, which results in the transition to STERILE ADAPTER INSTALLED state 813. In one aspect, the sensor is a mechanical switch that changes state when surgical device interface element 450 is mounted. Alternatively, the sensor can be an optical sensor, an inductive sensor, or a capacitive sensor, as described above.

Thus, when the user performs INSTALL STERILE ADAPTER act 817, the state of instrument manipulator assembly 440 goes from INSERTION EXTENDED state 812 to STERILE ADAPTER INSTALLED state 813, which is represented in FIG. 4B. In STERILE ADAPTER INSTALLED state 813, insertion assembly 431 is extended and the preload engage/disengage mechanism is not engaged.

When a surgical device interface element 450 is mounted on each of the instrument manipulator assemblies, DRAPING process 810 is complete. Following completion of DRAPING process 810, the user uses the clutch button on instrument manipulator assembly 440 to move instrument manipulator assembly 440 manually to the home position.

In RETRACT INSERTION act 818, each of the instrument manipulator assemblies is retracted and returned to the home position. Upon completion of RETRACT INSERTION act 818, each of the instrument manipulator assemblies is in STERILE ADAPTER INSTALLED, INSERTION RETRACTED state 820, sometimes referred to as state 820. In state 820, there is no preload force on surgical device interface element 450 because the preload engage/disengage mechanism is still disengaged.

Prior to considering further operation of instrument manipulator assembly 440, the structure of surgical device interface element 450 is first described. In this aspect, surgical device interface element 450 includes a frame 451 and a movable manipulator-instrument interface plate 451C. Moveable manipulator-instrument interface plate 451C, sometimes referred to as movable body 451C, is mounted in frame 451 so that moveable body 451C can move in the proximal and distal directions within frame 451. A plurality of intermediate disks is mounted in manipulator-instrument interface plate 451C so that each of the plurality of intermediate disks can rotate relative to frame 451.

In this aspect, each intermediate disk in the plurality of disks is the same, and so intermediate disk 453 is representative of each of the plurality of intermediate disks. Each intermediate disk 453 of the plurality of intermediate disks includes an intermediate driven interface 455, sometimes referred to as a first intermediate disk interface, and an intermediate drive interface 456, sometime referred to as a second intermediate disk interface. Intermediate driven interface 455 is opposite and removed from intermediate drive interface 456. In one aspect, intermediate driven interface 455 includes a first alignment receptacle and drive dog receptacles. Intermediate drive interface 456 includes drive dogs and an engagement structure. An example of a moveable manipulator-instrument interface plate and a plurality of intermediate disks suitable for use as moveable manipulator-instrument interface plate 451C and the plurality of intermediate disks in FIGS. 4A to 4G are presented in U.S. Patent Application Publication No. US 2016/0184035 A1, PCT International Publication No. WO 2015/023834 A1, and PCT International Publication No. WO 2015/023840 A1, each of which was previously incorporated by reference.

Movable body 451C also includes a plurality of hard stop receptacles 457. Plurality of hard stop receptacles 457 extends from a proximal face of movable body 451C in a distal direction into movable body 451C.

When instrument manipulator assembly 440 is retracted to the home position so that the instrument manipulator assembly 440 is in state 820, controller 290 initiates STERILE ADAPTER ENGAGEMENT SEQUENCE act 821. In STERILE ADAPTER ENGAGEMENT SEQUENCE act 821, controller 290, in one aspect, commands insertion assembly 431 to move instrument manipulator assembly 440 to a first predetermined location, a fully withdrawn position, which is proximal to the home position.

Figure 4C:
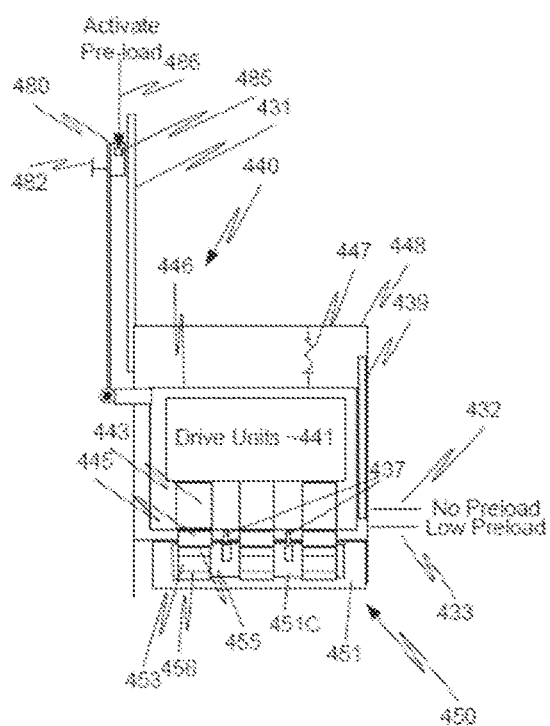

When instrument manipulator assembly 440 is at the fully withdrawn position, in one aspect, controller 290 sends an ACTIVATE PRELOAD signal 486 to preload engage/disengage mechanism 485 in preload assembly 480. In response to ACTIVATE PRELOAD signal 486, preload engage/disengage mechanism 485 engages the preload, and then controller 290 causes insertion assembly 431 to return to the home position (FIG. 4C). As insertion assembly 431 moves instrument manipulator assembly 440 from the fully withdrawn position to the home position, motor pack 446 is displaced distally relative to housing 448 of instrument manipulator assembly 440 from no preload position 432 to low preload position 433. This displacement stretches motor pack return spring 447. The engagement of the preload engage/disengage mechanism holds motor pack 446 in the distally displaced position relative to housing 448 so that there is a preload force on motor pack 446 in the distal direction.

Thus, when instrument manipulator assembly 440 is moved to home position, the displacement of motor pack 446 from no preload position 432 to low preload position 433 relative to housing 448 causes a drive interface of each drive output disk 445 of the plurality of drive output disks to contact a corresponding intermediate driven interface 455 of the plurality of intermediate driven interfaces of the plurality of intermediate disks. Thus, the motion of instrument manipulator assembly 440 causes each intermediate disk 453 to contact movable body 451C and to move movable body 451C in the distal direction. When movable body 451C moves distally as far as possible within frame 451, further motion of drive output disk 445 in the distal direction is inhibited.

Consequently, as instrument manipulator assembly 440 continues to move to the home position, the preload spring assembly in each drive output assembly 443 of the plurality of drive output assemblies is compressed so that a preload force is exerted on each drive output disk 445 in the plurality of drive output disks. This preload force is sometime referred to as a first preload force or a low preload force. The preload force pushes against drive output disk 445 and against a corresponding intermediate driven interface 455 so that the preload force is transferred to each intermediate disk 453 of the plurality of intermediate disks in surgical device interface element 450. This configuration is illustrated in FIG. 4C.

When surgical device interface element 450, sometimes referred to as a surgical device interface, is first mounted on instrument manipulator assembly 440, the elements of intermediate driven interface 455 may not be aligned with corresponding elements of the drive interface on drive output disk 445. If the elements of disks 453 and 445 are not aligned, the two disks are partially coupled together by features in the drive and intermediate driven interfaces, but the two disks are not coupled, e.g., mated, to each other.

Next, in STERILE ADAPTER ENGAGEMENT SEQUENCE act 821, controller 290 sends a signal to instrument manipulator assembly 440 to rotate drive output disk 445. Rotation of intermediate disk 453 is inhibited and drive output disk 445 is rotated until the drive interface of drive output disk 445 mates with intermediate driven interface 455 of intermediate disk 453. The partial coupling of the elements of the drive interface on drive output disk 445 with the corresponding elements of intermediate driven interface 455 on intermediate disk 453 assures that the two disks remain partially coupled under the preload force as the two disks rotate. In one aspect, when the two disks are coupled, another sensor detects a change in a height of the disk stack and sends a signal to controller 290 to stop the rotation of drive output disk 445. When the two disks are mated, the first preload force is on the disks. The mating of drive output disk 445 and intermediate disk 453 is the same as the mating of corresponding disks as described in U.S. Patent Application Publication No. US 2016/0184035 A1.

Upon mating of each drive output disk of instrument manipulator assembly 440 with the corresponding intermediate disk of surgical device interface element 450 STERILE ADAPTER ENGAGEMENT act 821 is complete. Instrument manipulator assembly 440 is in LOW PRELOAD SET, DISKS ENGAGED state 831 of NORMAL USE process 830.

Several acts are possible when instrument manipulator assembly 440 is in in LOW PRELOAD SET, DISKS ENGAGED state 831. For example, a user may install an instrument and continue with a surgical procedure. Upon completion of the surgical procedure, as described more completely below, NORMAL USE process 830 returns to LOW PRELOAD SET, DISKS ENGAGED state 831, and then the user undrapes patient side support system 210. Alternatively, a user can press the emergency instrument release button. Thus, each of these acts is considered in turn.

When instrument manipulator assembly 440 is in LOW PRELOAD SET, DISKS ENGAGED state 831, a user may depress emergency instrument release button 482 in EMERGENCY INSTRUMENT RELEASE (EIR) BUTTON act 822. Activating emergency instrument release button 482, e.g., depressing button 482, causes preload engage/disengage mechanism 485 to disengage the preload engage/disengage mechanism of preload assembly 480, and so the low preload force on the disk stack is released. This returns instrument manipulator assembly 440 to STERILE ADAPTER INSTALLED, INSERTION RETRACTED state 820.

Alternatively, when instrument manipulator assembly 440 is in in LOW PRELOAD SET, DISKS ENGAGED state 831, the user can install an instrument in surgical device interface element 450. Thus, in INSTALL INSTRUMENT act 835, a first end of instrument 460 is slid along a ramp in frame 451 of surgical device interface element 450 until instrument 460 is held in the proper position, as illustrated in FIG. 4E. For this state of instrument manipulator assembly 440 with a low preload, movable manipulator-instrument interface plate 451C is not locked in placed and can be moved proximally. Thus, as instrument 460 is slid along the ramp, movable manipulator-instrument interface plate 451C is displaced proximally, which further compresses the first preload spring assemblies, and so the preload force on the disk stack comprised of disks 445, 453, and 463 is said to be about the first preload.

Upon completion of INSTALL INSTRUMENT act 835, instrument manipulator assembly 440 is in INSTRUMENT INSTALLED state 832, sometimes referred to as state 832.

In state 832, the preload on the disk stack comprised of disks 445, 453, and 463 is about the first preload and the driven interface of driven disk 464 probably is not mated with intermediate drive interface 456 of intermediate disk 453.

Prior to considering INSTRUMENT ENGAGEMENT SEQUENCE act 836, which changes the state of instrument manipulator assembly 440 from INSTRUMENT INSTALLED state 832 to INSTRUMENT ENGAGED state 833, the features of instrument 460 are briefly considered. Instrument 460, in one aspect, is the same as the surgical instrument described in U.S. Patent Application Publication No. US 2016/0184037 A1.

In this aspect, instrument 460 (FIG. 4E) includes a body 465 and a main tube 467. Main tube 467 extends distally from body 465. Body 465 includes a driven disk receptacle 463, a shaft 466, and a driven disk 464. Shaft 466 and driven disk 464 are part of a transmission unit that transmits received torque through the instrument to one or more components of the instrument.

A proximal end of shaft 466 extends into driven disk receptacle 463, and driven disk 464 is mounted on the proximal end of shaft 466 so that driven disk 464 is positioned in driven disk receptacle 463. Driven disk 464 includes a driven interface that interfaces with intermediate drive interface 456 of intermediate disk 453.

The driven interface of driven disk 464 includes an engagement receptacle, drive dog receptacles, and a rotation disable element. The rotation disable element includes a rotation locking mechanism. Upon engagement of the rotation disable element, the rotation locking mechanism engages driven disk receptacle 464 and prevents rotation of driven disk 464.

When instrument 460 is coupled to instrument manipulator assembly 440, each driven disk 464 pushes a corresponding intermediate disk 453 in surgical device interface element 450 proximally so that intermediate disk 453 can rotate freely. This increases the preload force on the disk stack. However, when instrument 460 is first mounted on surgical device interface element 450, the elements of intermediate drive interface 456 may not be aligned with corresponding elements of the driven interface on driven disk 464. If the elements of the two disks 453 and 464 are not aligned, the two disks are partially coupled together by features in intermediate drive interface 456 and in the driven interface, but the two disks are not mated to each other.

When intermediate drive interface 456 of an intermediate disk 453 is not aligned with the corresponding driven interface of driven disk 464, an engagement structure on intermediate drive interface 456 of intermediate disk 453 engages a rotation disable element on driven disk 464 of instrument 460. The rotation disable element includes a rotation locking mechanism. Upon engagement of the rotation disable element, the rotation locking mechanism engages driven disk receptacle 464 and prevents rotation of driven disk 464.

When instrument 460 is coupled to instrument manipulator assembly 440, instrument manipulator assembly 440 detects the presence of instrument 460, and sends a signal to controller 290. In response to the signal, controller 290 sends a signal to instrument manipulator assembly 440 to perform INSTRUMENT ENGAGEMENT SEQUENCE act 836, sometimes referred to as act 836.

In response to the signal from controller 290, instrument manipulator assembly 440 rotates drive output disk 445, which in turn rotates intermediate disk 453. As the intermediate drive interface 456 of intermediate disk 453 rotates with driven disk 464 fixed in place, each element on intermediate drive interface 456 rotates into alignment with the corresponding element of the driven interface of driven disk 464 and mates with the corresponding element. The coupling of intermediate drive interface 456 and the driven interface on driven disk 464 releases the rotation lock on driven disk 464. Thus, the stack of disks, disks 445, 453, and 464, rotates as a unit. When disks 453 and 464 are coupled, the sensor again detects a change in a height of the disk stack and sends a signal to controller 290 to stop the rotation of drive output disk 445. When the stack of disks is mated, the preload force applied to the disk stack is referred to as the first longitudinal force, i.e., the first preload force.

Upon the mating of the intermediate disks of surgical device interface element 450 with the disks of instrument 460, instrument manipulator assembly 440 is in INSTRUMENT ENGAGED state 833, sometimes referred to as state 833, of NORMAL USE process 830. In state 833, instrument 460 is installed, the preload is the low preload, and instrument 460 can be removed from surgical device interface element 450. Instrument 460 can be removed, because with the low preload, movable manipulator-instrument interface plate 451C is not locked in placed, and so can be displaced in the proximal direction.

In the configuration of FIG. 4E, surgical device interface element 450 cannot be removed without removing instrument 460. The installation of instrument 460 prevents use of the release buttons on the sides of surgical device interface element 450. Thus, surgical device interface element 450 includes a mechanical sterile adapter assembly removal lockout so that when instrument 460 is mounted in surgical device interface element 450, instrument 460 activates the mechanical sterile adapter assembly removal lockout.

Unlike the prior system, which inhibited operation of a mechanical release button for the surgical device interface element whenever a preload force was present, there is no interlock on surgical device interface element 450 based on the preload state. The only interlock on surgical device interface element 450 is a mechanical interlock based on whether instrument 460 is mounted in surgical device interface element 450.

However, in the configuration of FIG. 4E, instrument 460 can still be removed. As explained more completely in U.S. Patent Application Publication No. US 2016/0184036 A1, in one aspect, there are release buttons on each side of instrument 460. Engaging the release buttons causes a mechanism in instrument 460 to push movable body 451C in surgical device interface element 450 proximally so that intermediate disk 453 and driven disk 464 are disengaged and instrument 460 can be removed.

Thus, in REMOVE INSTRUMENT act 838, a user manipulates the release buttons on each side of instrument 460, which disengages intermediate disk 453 and driven disk 464, and then the user slides instrument 460 out of surgical device interface element 450. The removal of instrument 460 changes the state of instrument manipulator assembly 440 from INSTRUMENT ENGAGED state 833 back to LOW PRELOAD SET, DISKS ENGAGED state 831 of NORMAL USE process 830.

EXTEND INSERTION act 837 changes the state of instrument manipulator assembly 440 from INSTRUMENT ENGAGED state 833 to INSTRUMENT IN USE HIGH PRELOAD state 834, sometimes referred as state 834. State 834 is in both NORMAL USE process 830 and INSTRUMENT TIP BEYOND CANNULA state 850.

In EXTEND INSERTION act 837, a distal end of instrument 460 is moved into and through a cannula by insertion assembly 431 moving instrument manipulator assembly 440 in the distal direction. As the distal end instrument 460 is inserted into the cannula by insertion assembly 431 moving instrument manipulator assembly 440, a second preload force is applied on the disk stack of disks 445, 453, and 464 by preload assembly 480 before an end component coupled to main tube 467 protrudes from a distal end of the cannula.

Specifically, as instrument 460 moves distally, preload assembly 480 moves distally along the preload track. In one aspect, when instrument manipulator assembly 440 moves distally a predetermined distance Zload, preload assembly 480 causes motor pack 446 to move predetermined distance Zload plus an additional distance Δ. In another aspect, a motor controller moves motor pack 446 distance Δ with respect to housing 448 irrespective of or in coordination with movement of instrument manipulator assembly 440 by insertion assembly 431.

In both of these aspects, the movement of motor pack 446 the additional distance Δ with respect to the housing 448 compresses the preload spring assembly in each drive output assembly 443 of the plurality of drive output assemblies so that a second preload force is exerted on each drive output disk 545 in the plurality of drive output disks. The second preload force reduces any backlash between rotation of the motor shaft in drive units 441 and rotation of shaft 466 in instrument 460 to less than 0.7 degrees before the distal end of instrument 260 exits the cannula.

The movement of motor pack 446 the additional distance Δ also further stretches return spring 447, and in addition inserts each of plurality of hard stops 437 into a corresponding hard stop receptacle in plurality of hard stop receptacles 457. Plurality of hard stops 437 prevents any proximal movement of moveable body 451C in surgical device interface element 450. The combination of plurality of hard stops 437 and plurality of hard stop receptacles 457 forms an instrument removal interlock and prevents removal of instrument 460. If a person tries to engage the release buttons on instrument 460, the mechanism in instrument 460 cannot push movable body 451C in surgical device interface element 450 proximally, because plurality of hard stops 437 prevents any proximal movement of moveable body 451C, and so intermediate disk 453 and driven disk 464 cannot be disengaged.

The use of plurality of hard stop receptacles 457 is illustrative only and is not intended to be limiting. In another aspect, plurality of hard stop receptacles 457 is not used. Instead, plurality of hard stops 437 contacts a proximal surface of moveable body 451C and prevents movement of moveable body 451C in the proximal direction. Upon completion of EXTEND INSERTION act 837, instrument manipulator assembly 440 is in INSTRUMENT IN USE HIGH PRELOAD state 834. In state 834, all the disks in the disk stack of disks 445, 453, and 464 are engaged and there is a second preload force on the disk stack. Neither surgical device interface element 450 nor instrument 460 can be removed in state 834.

RETRACT INSERTION act 839 changes the state of instrument manipulator assembly 440 from INSTRUMENT IN USE HIGH PRELOAD state 834 to INSTRUMENT ENGAGED state 833. In RETRACT INSERTION act 839, instrument manipulator assembly 440 is moved along insertion assembly 431 by the user to the home position. As instrument manipulator assembly 440 is moved to home position, the distal end of instrument 460 no longer extends through the cannula, and the second preload force is changed to the first preload force by the preload engage/disengage mechanism 485 of preload assembly 480, i.e., as instrument manipulator assembly 440 is withdrawn, motor pack 446 moves from high preload position 434 to low preload position 433 relative to housing 448.

If for some reason it is necessary to remove instrument 460 while the distal tip of instrument 460 extends beyond the distal end of the cannula in state 834, a person pushes emergency instrument release button 482 to implement EMERGENCY INSTRUMENT RELEASE BUTTON act 851. EMERGENCY INSTRUMENT RELEASE (EIR) BUTTON act 851 changes the state of instrument manipulator assembly 440 from INSTRUMENT IN USE, HIGH PRELOAD state 834 to NO PRELOAD state 861 of USER INTERFACE (UI) GUIDED RECOVERY process 860. The states of USER INTERFACE GUIDED RECOVERY process 860 are illegal instrument states.

In EMERGENCY INSTRUMENT RELEASE BUTTON act 851, activating emergency instrument release button 482 causes the longitudinal force on motor pack 446 to be released. Consequently, return spring 447 pulls motor pack 446 back to a fully withdrawn position within housing 448.

With motor pack 446 fully withdrawn, plurality of hard stops 437 is retracted from plurality of hard stop receptacles 457 in movable body 451C of surgical device interface element 450 and disks 453 and 464 are no longer subject to any preload forces. Thus, the release buttons on instrument 460 can be used to remove instrument 460 from surgical device interface element 450 at any position of insertion assembly 431.

However, to remove instrument 460 from the cannula, RETRACT INSERTION act 865 is performed. RETRACT INSERTION act 865 changes the state of instrument manipulator assembly 440 from NO PRELOAD state 861 to NO PRELOAD, INSERTION HOME state 862 of USER INTERFACE GUIDED RECOVERY process 860. In RETRACT INSERTION act 865, the user engages the clutch button of instrument manipulator assembly 440 and moves instrument manipulator assembly 440 along insertion assembly 431 to the home position.

If instrument manipulator assembly 440 is in INSTRUMENT ENGAGED state 833, with instrument 460 is installed and the low preload, EMERGENCY INSTRUMENT RELEASE BUTTON act 867 can be performed. In EMERGENCY INSTRUMENT RELEASE BUTTON act 867, activating emergency instrument release button 482 causes the longitudinal force on motor pack 446 to be released. Consequently, return spring 447 pulls motor pack 446 back to a fully withdrawn position within housing 448 so that there is no preload. Performance of EMERGENCY INSTRUMENT RELEASE BUTTON act 867, changes the state of instrument manipulator assembly 440 from INSTRUMENT ENGAGED state 833 to NO PRELOAD, INSERTION HOME state 862.

In NO PRELOAD, INSERTION HOME state 862, instrument 460 is withdrawn from the cannula, and there is no preload force on the disk stack. Thus, it is safe and possible to remove instrument 460 from surgical device interface element 450.

In REMOVE INSTRUMENT act 866, a user manipulates the release buttons on each side of instrument 460, which disengages intermediate disk 453 and driven disk 464, and then the user slides instrument 460 out of surgical device interface element 450. Completion of REMOVE INSTRUMENT act 866 changes the state of instrument manipulator assembly 440 from NO PRELOAD, INSERTION HOME state 862 to STERILE ADAPTER INSTALLED, INSERTION RETRACTED state 820.

During a normal surgical procedure, RETRACT INSTRUMENT act 839 is performed to change the state of instrument manipulator assembly 440 from INSTRUMENT IN USE HIGH PRELOAD state 834 to INSTRUMENT ENGAGED state 833. Then, REMOVE INSTRUMENT act 838 is performed to change the state of instrument manipulator assembly 440 from INSTRUMENT ENGAGED state 833 to LOW PRELOAD SET, DISKS ENGAGED state 831.

Since the surgical procedure is complete, the drape needs to be removed from patient side support system 210. To facilitate UNDRAPING process 840, in EXTEND INSERTION act 841, the user uses the clutch button on instrument manipulator assembly 440 to move instrument manipulator assembly 440 distally, As instrument manipulator assembly 440 moves distally, preload assembly 480 moves distally along the preload track. In one aspect, when instrument manipulator assembly 440 moves distally a predetermined distance Zload, preload assembly 480 causes motor pack 446 to move predetermined distance Zload plus an additional distance Δ to a high preload position 434 with respect to housing 448. The movement of motor pack 446 the additional distance Δ compresses the preload spring assembly in each drive output assembly 443 of the plurality of drive output assemblies so that a second preload force is exerted on each drive output disk 545 in the plurality of drive output disks. This second preload force is sometimes referred to a high preload force relative to the low preload force, described above.

Figure 4D:
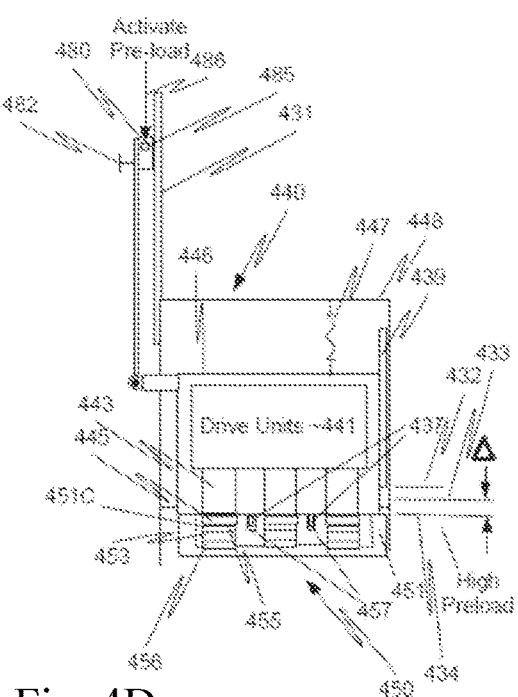

The movement of motor pack 446 the additional distance Δ also further stretches return spring 447, and in addition inserts each of plurality of hard stops 437 into a corresponding hard stop receptacle in plurality of hard stop receptacles 457. Plurality of hard stops 437 prevents any proximal movement of moveable body 451C in surgical device interface element 450. This configuration is illustrated in FIG. 4D. Thus, EXTEND INSERTION act 841 changes the state of instrument manipulator assembly 440 from LOW PRELOAD SET STERILE ADAPTER ENGAGED state in NORMAL USE process 830 to STERILE ADAPTER INSTALLED, HIGH PRELOAD state 842 in UNDRAPING process 840. In STERILE ADAPTER INSTALLED, HIGH PRELOAD state 842, the second preload being is applied to the engaged disks (drive output disk 445 and intermediate disk 453) with surgical device interface element 450 mounted on instrument manipulator assembly 440.

In the prior system for either the first preload condition or the second preload condition, removal of the sterile adapter required first depressing a preload release button on the instrument manipulator assembly to release the preload condition and also to disable a lock on a sterile adapter release button on the instrument manipulator assembly. The sterile adapter release button on the instrument manipulator assembly was then used to remove the sterile adapter. See U.S. Patent Application Publication No. US 2016/0184037 A1 for more details of the prior system.

In contrast, in REMOVE STERILE ADAPTER/DRAPE act 843, the user squeezes the release buttons on the sides of surgical device interface element 450 and moves surgical device interface element 450 in the distal direction away from the distal face of instrument manipulator assembly 440, irrespective of the second preload condition being active. There is no requirement to manipulate any button on instrument manipulator assembly 440 to remove surgical device interface element 450 under the second preload condition. This makes the removal of surgical device interface element 450 more intuitive because only features of surgical device interface element 450 are used to remove surgical device interface element 450. Also, it reduces confusion because emergency instrument release button 482 is not used or needed for removal of surgical device interface element 450 under any preload condition. After removal of removal of surgical device interface element 450, the user removes the surgical drape from patient side support system 210.

Upon completion of REMOVE STERILE ADAPTER act 843, instrument manipulator assembly 440 is in INSERTION EXTENDED state 844. The user performs RETRACT INSERTION act 845 to change the state of instrument manipulator assembly 440 from INSERTION EXTENDED state 844 to INSERTION HOME state 846.

In RETRACT INSERTION act 845, each of the instrument manipulator assemblies is retracted and returned to the home position by the user using the clutch button on an instrument manipulator assembly 440 to move that instrument manipulator assembly 440 to the home position.

With instrument manipulator assembly 440 in the home position, controller 290 performs PRELOAD RELEASE act 847 to change the state of instrument manipulator assembly 440 to START state 801. In one aspect, controller commands insertion assembly 431 to move instrument manipulator assembly 440 proximal to the home position, which as described more completely below, automatically release the preload. In another aspect, controller 290 commands a motor to move motor pack 446 to the no preload position.

Figure 9D:
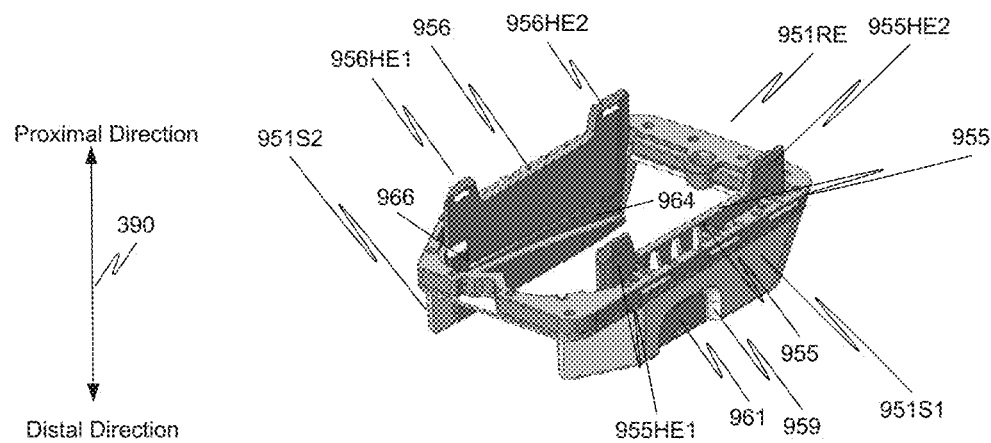
Figure 9E:
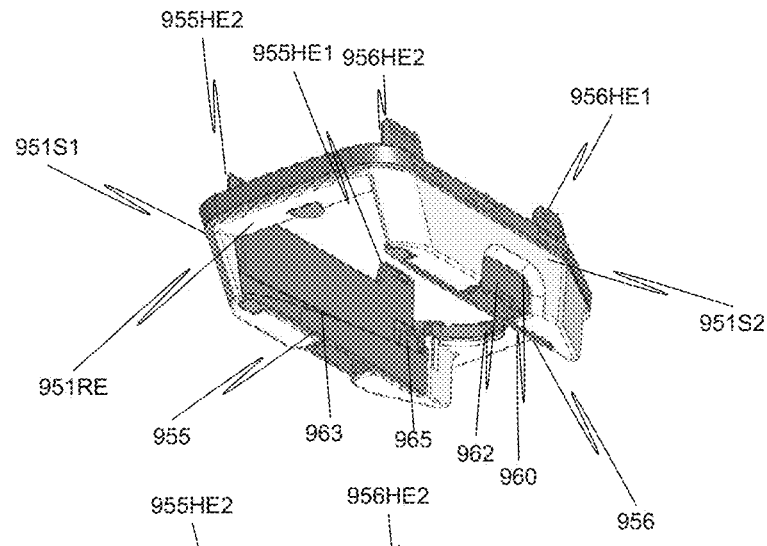
Figure 9F:
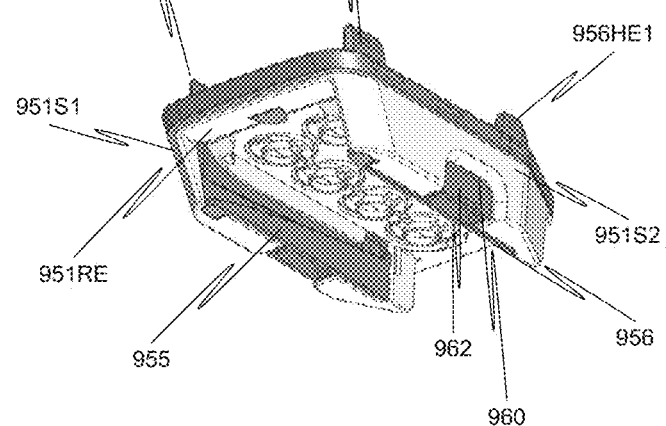

FIG. 9A shows one example of instrument manipulator assembly 940 affixed to insertion assembly 931 that in turn is attached to an insertion axis base assembly 932. Insertion axis base assembly 932 includes a motor and power electronics to move insertion assembly 931. Instrument manipulator assembly 940 is an example of instrument manipulator assembly 240 and instrument manipulator assembly 440. Insertion assembly 931 is an example of insertion assembly 331 and of insertion assembly 431.

Instrument manipulator assembly 940 includes two buttons—a clutch button 944 and an emergency instrument release button, which is not visible. The emergency instrument release button is an example of emergency instrument release button 482. If a user depresses, i.e., activates, clutch button 944, the user can manually move instrument manipulator assembly 940 along insertion assembly 931 in both the proximal and distal directions. The emergency instrument release button is used to release the preload, as described with respect to FIG. 8.

Instrument manipulator assembly 940 also includes a drive unit assembly 941 and a drive output unit 942. In this aspect, drive output unit 942 includes a plurality of drive output assemblies, e.g., eight drive output assemblies. Herein, drive output assembly 943 refers to any one of the eight drive output assemblies. In one aspect, only six of the eight drive output assemblies are used. Drive output assembly 943 includes a low backlash coupler and a drive output disk. Drive unit assembly, drive output unit 942 and drive output assembly 943 are equivalent to those described in U.S. Patent Application Publication No. US 2016/0184035 A1.

Sterile adapter assembly 250 (FIGS. 9B to 9G) includes a sterile adapter frame 951 and a sterile drape (not shown). The sterile drape is fixedly attached to sterile adapter frame 951. Sterile adapter assembly 250 is an example of a surgical device interface element. Sterile adapter frame 951 is an example of a surgical device interface element body. In more general terms, a surgical device interface element is a structure that includes a mechanical interface between a drive interface of a drive system and a driven interface of an instrument, such as a surgical instrument or a camera instrument.

Frame 951 of sterile adapter assembly 250 has a front end 951FE, i.e., a first end, a rear end 951RE, i.e., a second end, a first side 951S1 and a second side 951S2. Second end 951RE is sometimes referred to as an open end of sterile adapter assembly 250 and of sterile adapter frame 951, because second end 951RE is the end in which an instrument is inserted, and so is open to receive the instrument.

A first beam 955, sometimes referred to as beam 955, is movably attached to an inside of first side 951S1 of sterile adapter frame 951 so that when a distal end (a first end) of beam 955 moves in a first direction (inward), a proximal end (a second end) of beam 955 moves in a second direction (outward) opposite to the first direction. A second beam 956, sometimes referred to as beam 956, is movably attached to an inside of second side 951S2 of sterile adapter frame 951 so that when a distal end (a first end) of beam 956 moves in a first direction (inward), a proximal end (a second end) of beam 956 moves in a second direction (outward) opposite to the first direction. The construction of beams 955 and 956 is the same, and each beam has the same features.

In one aspect, beam 955 is attached to the inside of first side 951S1 by a first flexure so that when the distal end of beam 955 is moved inward, the proximal end of beam 955 moves outward. Beam 956 is attached to the inside of second side 951S2 by a second flexure so that when the first end of beam 956 is moved inward, the proximal end of beam 956 moves outward.

In another aspect, beam 955 is pivotally attached to the inside of first side 951S1 and includes a spring that maintains a proximal end of beam 955 in an engaged position. When a force is applied to the distal end of beam 955, the proximal end of beam 955 pivots to a disengaged position. Similarly, beam 956 is pivotally attached to the inside of second side 951S3 and includes a spring that maintains a proximal end of beam 956 in an engaged position. When a force is applied to the distal end of beam 956, the proximal end of beam 955 pivots to a disengaged position.

A first hook extension 955HE1 extends in the proximal direction from beam 955. First hook extension 955HE1 is adjacent a third end of beam 955. A second hook extension 955HE2 extends in the proximal direction from beam 955. Second hook extension 955HE2 is adjacent a fourth end of beam 955, where the third end of beam 955 is removed from and does not intersect the fourth end of beam 955.

A first hook extension 956HE1 extends in the proximal direction from beam 956. First hook extension 956HE1 is adjacent a third end of beam 956. A second hook extension 956HE2 extends in the proximal direction from beam 956. Second hook extension 956HE2 is adjacent a fourth end of beam 956, where the third end of beam 956 is removed from and does not intersect the fourth end of beam 956.

Side 951S1 includes a thru-opening 959 (FIGS. 9B, 9C, and 9D) extending from a proximal edge of side 951S1. A sterile adapter release button 961, sometimes referred to as release button 961, is positioned in thru-opening 959. Sterile adapter release button 961 is affixed to an outer side surface of beam 955.

Second side 951S2 includes a thru-opening 960 (FIGS. 9E and 9F) extending from a proximal edge of second side 951S2. A sterile adapter release button 962, sometimes referred to as release button 962, is positioned in thru-opening 960. Sterile adapter release button 962 is affixed to an outer side surface of beam 956.

The inner side of each of beams 955 and 956 includes an instrument insertion skid plate 963 and 964, respectively, that terminates in a parking slot. Instrument insertion skid plate 963 is formed on the inner side of beam 955. Instrument insertion skid plate 963 extends from the fourth end of beam 955 to a parking slot 965, which is adjacent to the third end of beam 955. Instrument insertion skid plate 964 is formed on the inner side of beam 956. Instrument insertion skid plate 964 extends from the fourth end of beam 956 to a parking slot 966, which is adjacent to the third end of beam 956.

Sterile adapter frame 951 includes a movable manipulator-instrument interface plate 951C, sometimes referred to as movable body 951C. Movable manipulator-instrument interface plate 951C can move in the distal and proximal directions, e.g., in first and second directions, within sterile adapter frame 951.

Movable manipulator-instrument interface plate 951C includes a receptacle for each intermediate disk in plurality of intermediate disks 953P. Moveable body 951C also includes a plurality of hard stop receptacles 957 (FIG. 9C), which is optional.

Each intermediate disk has a cylindrical body. Each of plurality of intermediate disks 953P is mounted in a corresponding intermediate disk receptacle of a plurality of intermediate disk receptacles of movable body 951C so that each intermediate disk can rotate relative to sterile adapter frame 951 and relative to movable body 951C. Thus, plurality of intermediate disks 953P is rotatably mounted in sterile adapter frame 951. Also, each intermediate disk can move distally and proximally in the intermediate disk receptacle.

Each intermediate disk includes an intermediate driven interface on a first side of the intermediate disk and an intermediate drive interface on a second side of the intermediate disk. The intermediate driven interface is configured to mate with a drive interface on a drive output disk in drive output unit 942. Movable body 951C and plurality of intermediate disks 953P are equivalent to the movable body and plurality of intermediate disks of the sterile adapter described in PCT International Publication No. WO 2015/023840 A1, which was previously incorporated by reference.

FIGS. 10A and 10B illustrate the motions and forces required to attach sterile adapter assembly 250 to instrument manipulator assembly 1040, which is connected to insertion assembly 1031 (FIG. 10A), and to disconnect sterile adapter assembly 250 from instrument manipulator assembly 1040 (FIG. 10B). Instrument manipulator assembly 1040 also includes a drive unit assembly and a drive output unit. In this aspect, the drive output unit includes a plurality of drive output assemblies, e.g., eight drive output assemblies. Each drive output assembly includes a low backlash coupler and a drive output disk. The drive unit assembly, the drive output unit and the drive output assembly are equivalent to those described in U.S. Patent Application Publication No. US 2016/0184035 A1.

Instrument manipulator assembly 1040 is another example of instrument manipulator assembly 240 and instrument manipulator assembly 440. Insertion assembly 1031 is another example of insertion assembly 331 and of insertion assembly 431. Instrument manipulator assembly 1040 includes two buttons—a clutch button 1044 and an emergency instrument release button 1082. Emergency instrument release button 1082 is an example of emergency release button 482.

Clutch button 1044 is mounted in the housing of instrument manipulator assembly 1040. If a user depresses, i.e., activates, clutch button 1044, the user can manually move instrument manipulator assembly 1040 along insertion assembly 1031 in both the proximal and distal directions.

Emergency instrument release button 1082 is mounted in preload assembly 1080 of instrument manipulator assembly 1040. Emergency instrument release button is used to release the preload as described with respect to FIG. 8.

To mount sterile adapter assembly 250 on instrument manipulator assembly 1040, a user moves sterile adapter assembly 250 in direction 1091, the proximal direction, and presses sterile adapter assembly 250 into the distal face of instrument manipulator assembly 1040. The hook extensions of sterile adapter assembly 250 are movable and allow a hook in each of the hook extensions to snap into the distal face of instrument manipulator assembly 1040 to securely attach sterile adapter assembly 250 to instrument manipulator assembly 1040.

When sterile adapter assembly 250 is attached to instrument manipulator assembly 1040, as illustrated in FIG. 10A, a plunger of instrument manipulator assembly 1040 is depressed and breaks a light beam, which in turn generates a signal that indicates to controller 290 the presence of sterile adapter assembly 250. Alternatively, one of the other sensors described above could be used to detect the presence or absence of sterile adapter assembly 250.

To remove sterile adapter assembly 250, the user squeezes sterile adapter release buttons 961 and 962 in inward directions using forces 1092A and 1092B (inward), respectively, irrespective of whether there may be a preload force on sterile adapter assembly 250. The inward force on buttons 961 and 962 causes the beams to pivot which releases the hooks, including hooks 1071 and 1072 (FIG. 10C), holding sterile adapter assembly 250 to instrument manipulator assembly 1040, and so allows easy removal of sterile adapter assembly 250. When sterile adapter assembly 250 is removed from instrument manipulator assembly 1040, the plunger of instrument manipulator assembly 240 is no longer depressed, which in turn generates a signal that indicates to controller 290 the absence of sterile adapter assembly 250.

FIG. 10C is an illustration of sterile adapter assembly 250 mounted in instrument manipulator assembly 1040 with parts of sterile adapter assembly 250 and instrument manipulator assembly 1040 removed to show the hook and hook receiver latching mechanism used to mount and hold sterile adapter assembly 250 in the distal face of instrument manipulator assembly 1040. In the following description of sterile adapter assembly 250 and instrument manipulator assembly 1040, with respect to FIG. 10C, the configurations of the left and right hand sides of sterile adapter assembly 250 and instrument manipulator assembly 1040 are the same. Thus, the left hand side of FIG. 10C is described and each reference numeral is followed by a reference numeral for the corresponding feature of the right hand side feature of FIG. 10C to avoid replicating the description with different reference numerals for the left and right sides of sterile adapter assembly 250 and instrument manipulator assembly 1040

Instrument manipulator assembly 1040 includes a first side member 1073 and a second side member 1074. Side member 1073 (1074) includes a ramp side surface 1075 (1076), which forms part of a hook receiver 1077 (1078) of side member 1073 (1074). Hook receiver 1077 (1078) is shaped to engage a hook 1071 (1072) formed in hook extension 955HE2 (956HE2) of beam 955 (956), e.g. the hook receiver fits in the hook of the hook extension.

In sterile adapter assembly 250, beam 955 (956) is moveably connected to a side wall of sterile adapter assembly 250 by a flexure 1083 (1084). In this aspect, beam 955 (956) and flexure 1083 (1084) are formed as a single part. In more general terms, a first end of flexure 1083 (1084) is connected to beam 955 at a location between the distal and proximal ends of beam 955 (956). The location is selected to allow flexure to engage and to disengage hook 1071 (1072) formed in hook extension 955HE2 (956HE2) of beam 955 (956) from hook receiver 1077 (1078) of side beam 1073 (1074). A second end of flexure 1083 (1084) is connected to the side wall of sterile adapter assembly 250. In still more general terms, beam 955 (956) is pivotally connected to the sidewall at a location between the distal and proximal ends of beam 955 (956)

To remove sterile adapter assembly 250 from instrument manipulator assembly 1040, a user depresses each of release button 961, 962 towards the interior of sterile adapter assembly, i.e., provides a force 1092A on button release button 961 and a force 1092B on release button 962. Forces 1092A and 1092B on release buttons 961 and 962 are applied to the distal ends of beams 955 and 956.

The forces on the distal ends of beams 955 and 956 causes flexures 1083 and 1084 to bend such that the hooks in hook extensions 955HE1 and 956HE2 rotate outward away from the plane that bisects instrument manipulator assembly 1040 and that includes a lengthwise axis of instrument manipulator assembly 1040. The outward rotation of the hooks disengages the hooks from the hook receivers, which in turn allows sterile adapter assembly 250 to move in the distal direction out of instrument manipulator assembly 1040.

FIG. 11A is a more detailed illustration of a prior art surgical instrument that can be mounted in sterile adapter assembly 250. Instrument 260, in this aspect, includes a driven interface assembly 1161, a transmission unit 1165, a main tube 1167, a parallel motion mechanism 1168, a wrist joint 1169, and an end effector 1170. Wrist joint 1169 is described, for example, in U.S. Patent Application Publication No. US 2003/0036748 A1 (disclosing "Surgical Tool Having Positively Positionable Tendon-Activated Multi-Disk Wrist Joint"), which is incorporated herein by reference. Parallel motion mechanism 1168 is described, for example, in U.S. Pat. No. 7,942,868 B2 (filed Jun. 13, 2007, disclosing "Surgical Instrument With Parallel Motion Mechanism").

As shown in FIG. 11B, driven interface assembly 1161 includes a plurality of driven disks 1164P. Plurality of driven disks 1164P is an example of driven interface elements. Driven disk 1164 is representative of each driven disk of plurality of driven disks 1164P. Driven disk 1164 is mounted on a shaft of transmission unit 1165. Also, each driven disk 1164 is mounted in a receptacle in a body of driven interface assembly 1161.

Mechanical components (e.g., gears, levers, gimbals, cables etc.) in transmission unit 1165 transfer torques from plurality of driven disks 1164P to cables, wires, and/or cable, wire, and hypotube combinations that run through main tube 1167 to control movement of parallel motion mechanism 1168, wrist joint 1169, and end effector 1170. Main tube 1167, although substantially rigid, can be bent slightly between transmission unit 1165 and entry guide 270. This bending allows the instrument body tube bores in entry guide 270 to be spaced closer together than the size of the transmission units would otherwise allow. The bending is resilient so that main tube 1167 assumes its straight shape when instrument 260 is withdrawn from entry guide of 270 (the main tube may be formed with a permanent bend, which would prevent instrument body roll).

Driven interface assembly 1161 has on each side a pair of mounting wings (1162A1, 1162B1) and (1162A2, 1162B2). Also, on each side of transmission unit 1165 is a release button 1163A, 1163B. Mounting wing 1162B2 and release button 1163B are shown in FIG. 10.

Figure 13:
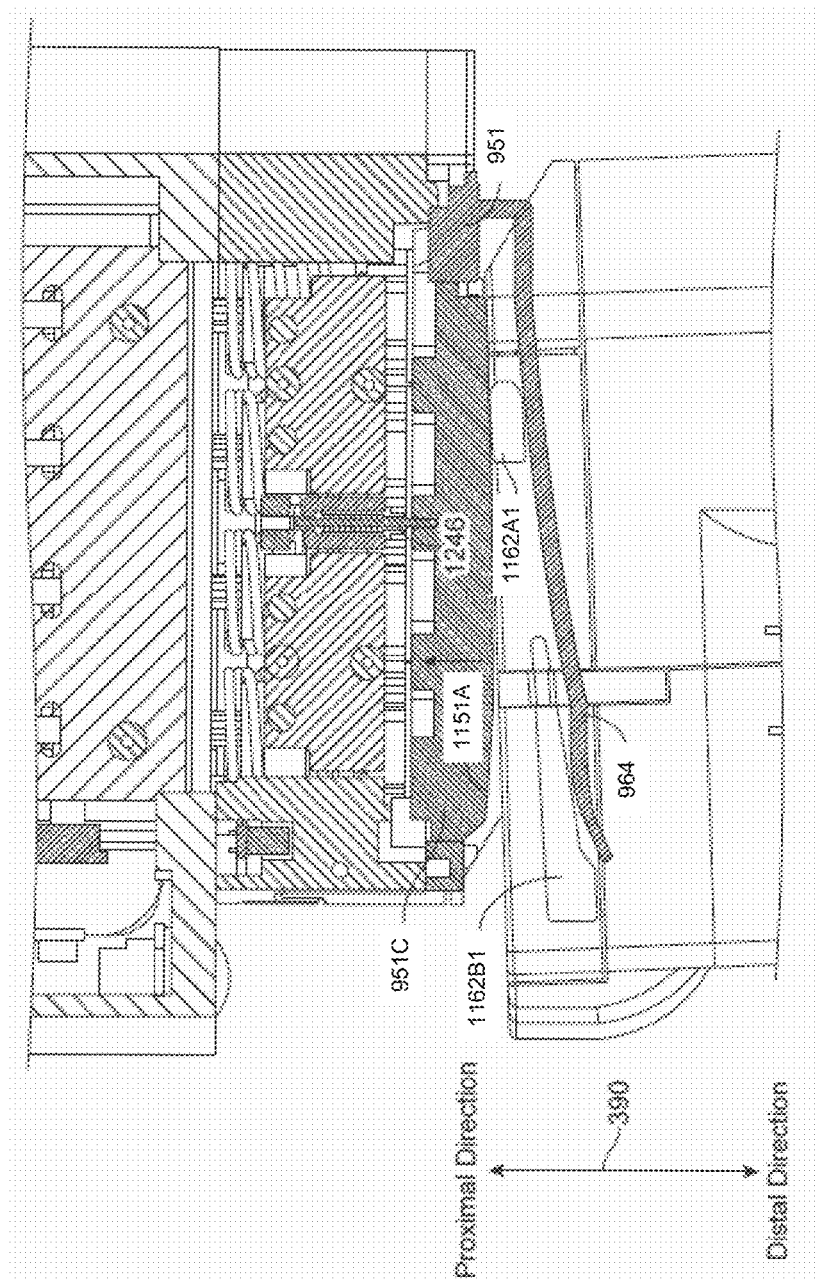
Figure 14:
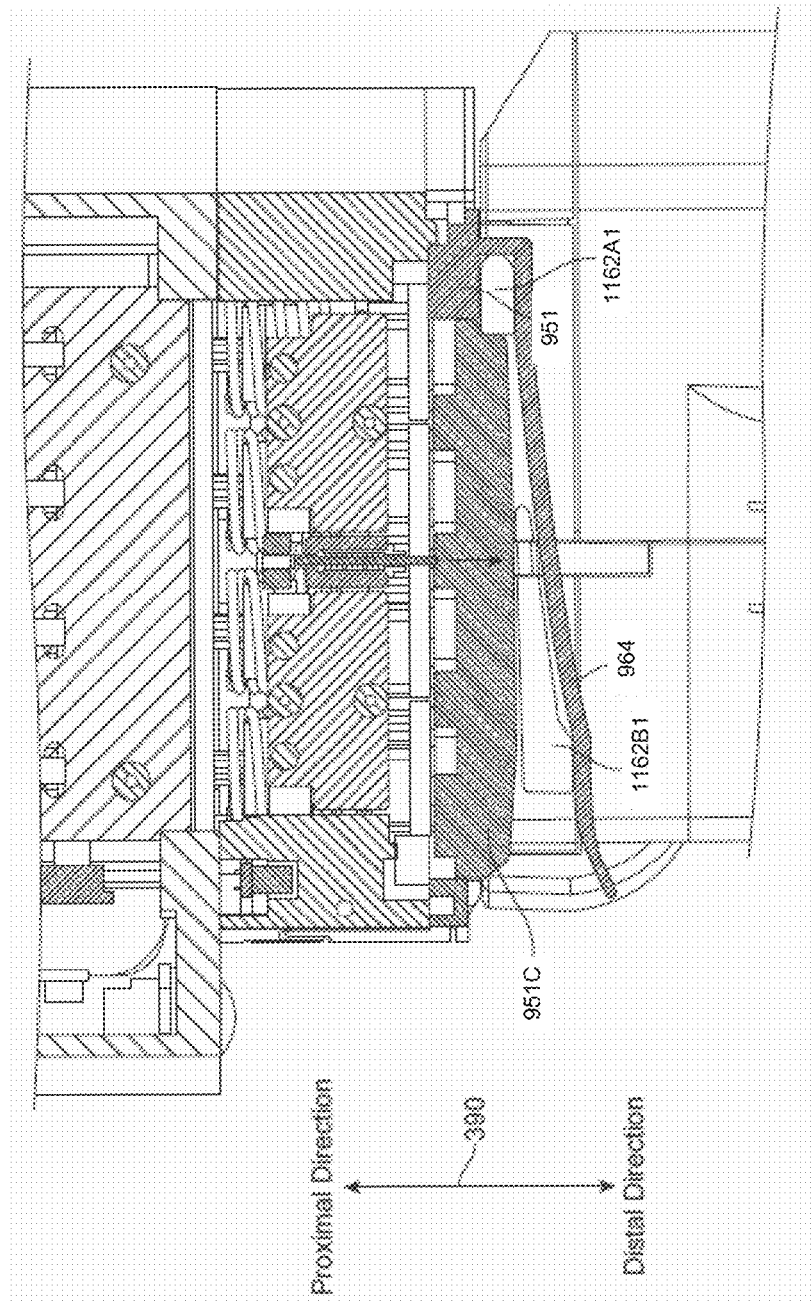

To mount instrument 260 in sterile adapter frame 951, first, mounting wings 1162A1, 1162A2 are placed on skid plates 963, 964 (FIGS. 9E, 9F, and 12 to 14) at open end 951RE of sterile adapter frame 951. FIGS. 12 to 14 are cutaway views with the outer side surface of sterile adapter frame 951 and beam 956 removed.

Mounting wing 1162A1 is resting on skid plate 964 that extends from an inner sidewall of beam 956. As instrument 260 is slid on skid plate 964 towards parking slot 966, which is at the opposite end of skid plate 964, (FIG. 12). A top surface of first mounting wings 1162A1, 1162A2 contacts the bottom edge of lip 1251A of movable body 951C, which moves movable body 951C in the proximal direction (FIGS. 12 and 13). The proximal motion of movable body 951C depresses plunger 1246 of instrument manipulator assembly 1040 in the proximal direction, which in turn generates a signal to controller 290 that instrument 260 is being loaded unto sterile adapter assembly 250.

When mounting wing 1162A1 reaches parking slot 966 (FIG. 14), the top surface of first mounting wings 1162A1, 1162A2 no longer contacts the bottom edge of lip 1251A of movable body 951C. Consequently, the preload force on movable body 951C moves body 951C in the distal direction (FIG. 13) and locks first mounting wing 1162A1 in place. When first mounting wing 1162A1 reaches the end of sterile adapter frame 951, second mounting wing 1162B1 rests on a flat portion of skid plate 964 near the open end of sterile adapter frame 951 (FIG. 14).

Each intermediate disk 953 in sterile adapter frame 951 is being pushed axially in the distal direction by the preload force on the plurality of drive output disks of the instrument manipulator assembly. Thus, as instrument 260 is mounted in sterile adapter frame 951, plurality of intermediate disks 953P transfers the first preload force to movable body 951C so that the preload force is applied to mounting wing 1162A1. This preload force is selected so that instrument 260 can be easily slid into sterile adapter frame 951, and so that a small preload force is maintained on all the disks.

When instrument 260 is mounted in sterile adapter assembly 250, instrument manipulator assembly 1040 detects the presence of instrument 260 and sends a signal to controller 290 that indicates the presence of instrument 260. In response to the signal, controller 290 in system 200 sends the signal to instrument manipulator assembly 1040 to rotate each drive output disk of the plurality of drive output disks of the instrument manipulator assembly.

As explained more completely in U.S. Patent Application Publication No. US 2016/0184037 A1, each drive output assembly 943 in drive output unit 942 is spring-loaded and is automatically positioned so that a preload force is exerted on each drive output disk after sterile adapter assembly 250 is mounted on instrument manipulator assembly 1040. The preload force pushes against the drive output disk and against a corresponding intermediate driven interface of intermediate disk 953 in sterile adapter frame 951.

However, when instrument 260 is first mounted on sterile adapter assembly 250, the elements of the intermediate drive interface of intermediate disk 953 may not be aligned with corresponding elements of driven interface 1180 on driven disk 1164. If the elements of the two disks 953 and 1164 are not aligned, the two disks are partially coupled, but the two disks are not mated to each other. Thus, a disk stack including the drive disk, the intermediate disk, and the driven disk are partially coupled. To mate the disks, INSTRUMENT ENGAGEMENT SEQUENCE act 836 is performed.

In one aspect, each of sterile adapter frame 951, movable body 951C, and the plurality of intermediate disks 653P are made by injection molding. Suitable materials for sterile adapter frame 951, movable body 951C, and plurality of intermediate disks 953P include polycarbonate, polyphenylsulfone (PPSU), polyethylenimine (PEI), etc.

Beams 955 and 956 of sterile adapter assembly 250 are included in a mechanical instrument removal lockout, which is activated by mounting instrument 260 in sterile adapter assembly 250. Specifically, if the proximal ends of beams 955 and 956 cannot move inward by pressing release buttons 961 and 962, the hooks of sterile adapter assembly 250 cannot be disengaged from the hook receivers of instrument manipulator assembly 1040. When instrument 260 is mounted in sterile adapter assembly 250, the body of instrument prevents inward movement of beams 955 and 956, and so instrument 260 is said to activate the mechanical instrument lock out, which are beams 955 and 956.

Figure 15:
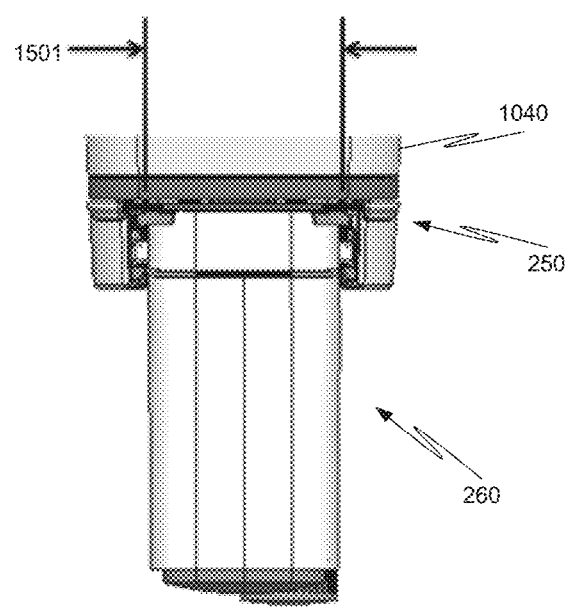
FIG. 15 is an illustration of the surgical instrument of FIGS. 11A and 11B mounted in the sterile adapter assembly of FIGS. 9B to 9F to activate the sterile adapter assembly lockout mechanism.

More specifically, as shown in FIG. 15, distance 1501 between beams 955 and 956 is selected based on the size of the body of instrument 260. Distance 1501 is selected so that when instrument 260 is mounted in sterile adapter assembly 250, any movement of the proximal ends of beams 955 and 956 is not sufficient to disengage the hooks of sterile adapter assembly 250 from the hook receivers of instrument manipulator assembly 1040. Thus, to prevent accidental release of sterile adapter assembly 250, the body of instrument 260 physically blocks movement of beams 955 and 946, thereby preventing sterile adapter assembly 250 removal when instrument 260 is present. This lock-out is independent of any preload force that may be present.

Figure 16:
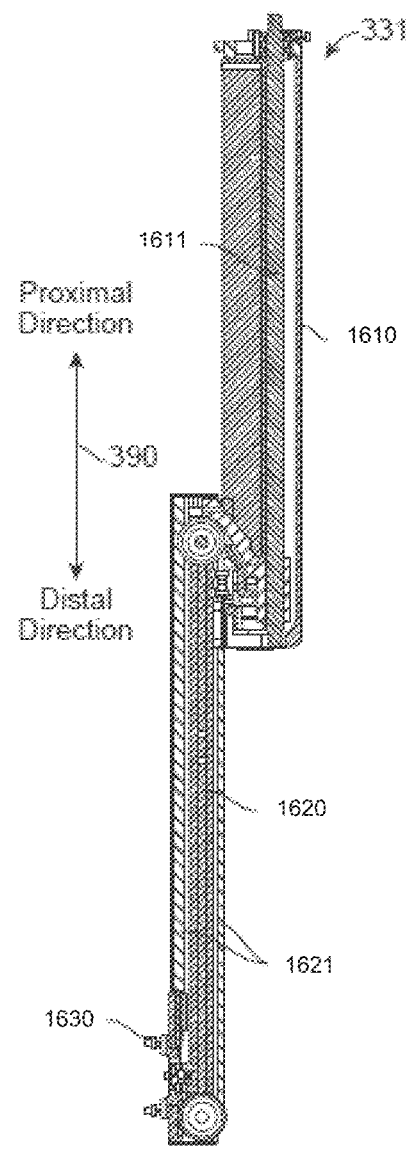
FIG. 16 is a more detailed illustration of a prior art insertion assembly.

FIG. 16 is a more detailed illustration of one aspect of insertion assembly 331. Insertion assembly 331 includes a frame 1610, a mid-carriage 1620, and a distal carriage 1630. Mid-carriage 1620 rides on a ball screw 1611 in frame 1610. In one aspect, ball screw 1611 has a 6 mm pitch, and so mid-carriage 1620 is back drivable. Mid-carriage 1620 includes metal belts 1621 that drive distal carriage 1630. Distal carriage 1630 is attached to an instrument manipulator assembly housing of instrument manipulator assembly 240. Distal carriage 1630 moves twice as far as mid-carriage 1620, in one aspect.

FIGS. 17A and 17B illustrate preload assembly 1080 and operation of preload assembly 1080. The construction and operation of preload assemblies 480 and 980 are the same as illustrated in FIGS. 17A and 17B, in one aspect. For ease of illustration, instrument 260, sterile adapter assembly 250, the housing of instrument manipulator assembly 1040, and insertion assembly 331 are not shown in FIGS. 17A and 17B. When preload assembly 1080 is in the configuration shown in FIG. 17A, the distal end of instrument 260 is, for example, positioned at an entry to a channel in entry guide 270. Similarly, in FIGS. 18A to 18E and 19A to 19C, only the elements necessary to understand the preload assembly are illustrated. The actual configuration associated with FIGS. 17A, 17B, 18A to 18E and 19A to 18C includes all the elements shown and described with respect to FIGS. 9A to 9E, 10A to 10C, 11A, and 11B.

Prior to considering the operation of preload assembly 1080, the elements in preload assembly 1080 are described. Unlike the preload assembly described in U.S. Patent Application Publication No. US 2016/0184036 A1, the preload supplied by preload assembly 980 can be released automatically by controller 290 and can be released manually by a user. The preload supplied by the preload assembly described in U.S. Patent Application Publication No. US 2016/0184036 A1 could only be released manually by the user.

In FIGS. 17A, 17B, 18A to 18E, and 19A to 19C, a preload track 1725 is mounted on mid-carriage 1620. A valley is located at a proximal end of preload track 1725. A ramp 1725R in preload track 1725 connects the valley to a flat portion of preload track 1725. A preload engagement ridge 1726 extends from preload track 1725 distal to ramp 1725R. A description of a preload track suitable for use as preload track 1725 is presented in U.S. Patent Application Publication No. US 2016/0184036 A1, which is incorporated herein by reference in its entirety.

A wheel 1783W is rotatably attached to a first end of a cam follower assembly 1783. Wheel 1783W rides on preload track 1725. (In some of FIGS. 17A, 17B, 18A to 18E, and 19A to 19C, wheel 1783W appears to be displaced from preload track 1725. This is for ease of illustration only. In all instances shown in FIGS. 17A, 17B, 18A to 18E and 19A to 19C, wheel 1783W is in contact with and rides on preload track 1725.)

Cam follower assembly 1783 pivots about pivot pin 1784, a first pivot pin. Cam follower assembly 1783 is rotatably connected to a first end of an arm 1782 in preload assembly 1080. A first end, e.g., a distal end, of arm 1782 is connected to a motor pack bracket 1781. A description of a cam follower assembly suitable for use as cam follower assembly 1783 is presented in U.S. Patent Application Publication No. US 2016/0184036 A1.

Motor pack bracket 1781 is affixed to a motor pack 1746. Thus, arm 1782 is coupled to motor pack 1746. As indicated above, the instrument manipulator assembly housing is affixed to distal carriage 1630. One example of motor pack 1746 is presented in U.S. Patent Application Publication No. US 2016/0184036 A1.

A second end, a proximal end, of preload engagement arm 1786 is rotatably coupled to a pivot pin 1784. Pivot pin 1784 is slideably coupled to the housing of instrument manipulator assembly 1040

A rolling pin 1786P is mounted in a first end, a distal end, of preload engagement arm 1786. Proximal to rolling pin 1786P in the first end of preload engagement arm 1786 is a preload engagement surface 1786S, sometimes referred to as surface 1786S. In this aspect, preload engagement surface 1786S is perpendicular to the flat portion of preload track 1725. Preload engagement arm 1786 is coupled to a linear rail 1787. A description of a preload engagement arm and linear rail suitable for use as preload engagement arm 1786 and linear rail 1787 is presented in U.S. Patent Application Publication No. US 2016/0184036 A1.

In this aspect, preload engage/disengage arm 1785, sometimes referred to as arm 1785, is a T-shaped structure having a cross-bar and a leg. The T-shaped structure is rotated ninety degrees clockwise with respect to the vertical so that the leg of the T-shaped structure is horizontal, or in more general terms is perpendicular to the cross-bar. The use of a T-shape structure is optional. Any shape of preload engage/disengage arm 1785 that can perform the acts described below can be used.

The cross-bar of preload engage/disengage arm 1785 functions as a lever, and so is sometimes referred to as a lever or a lever portion of preload engage/disengage arm 1785. A hook on a second end, a proximal end, of the cross-bar of preload engage/disengage arm 1785 is engaged with rolling pin 1786P in the second end of arm 1785 when a preload is enabled, and is disengaged with rolling pin

1786P when the preload is disabled. Emergency instrument release button 1082 is coupled to, e.g., is in contact with, a first end, a distal end, of the cross-bar of preload engage/ disengage arm 1785. Emergency instrument release button 1082 is an example of emergency instrument release button 482 and emergency instrument release button 982.

Between the first and second ends of the cross-bar of preload engage/disengage arm 1785, preload engage/disengage arm 1785 is rotatably mounted on another pivot pin 1788, a second pivot pin, which functions as a fulcrum for the lever action of preload engage/disengage arm 1785. The leg of the T-shaped structure extends from the lever portion of arm 1785 so that pivot pin 1788 is centered with respect to the leg of the T-shaped structure. Thus, the leg of preload engage/disengage arm 1785 has a first end and a second end, with the first end connected to the cross-bar of preload engage/disengage arm 1785.

A torsional spring 1789 (FIG. 17C) concentric with pivot pin 1788 exerts a counter-clockwise torque on preload engage/disengage arm 1785 (counter-clockwise relative to FIGS. 17A, 17B, 18A to 18E, and 19A to 19C). Torsional spring 1789 provides a force on preload engage/disengage arm 1785, which moves the hook of preload engage/disengage arm 1785 away from an axis extending through pivot pin 1784 and pivot pin 1788. The axis extending through pivot pin 1784 and pivot pin 1788 is perpendicular to a lengthwise axis of pivot pin 1784 and a lengthwise axis of pivot pin 1788. Torsional spring 1789 rotates preload engage/disengage arm 1785 in a preload disengage direction, which is necessary to keep preload engage/disengage arm 1785 in the released position that is shown in FIGS. 18A 18B, 18C, 19B, and 19C.

In one aspect, with respect to emergency instrument release button 1082, the lever portion of preload engage/ disengage arm 1785 is a Class 1 lever because the fulcrum is between the effort (the forces supplied by emergency instrument release button 1082) and the load (the coupling between the hook and rolling pin 1786P). While in this example, preload engage/disengage arm 1785 is implemented as a Class 1 lever, this is illustrative only and is not intended to be limiting. In other aspects, a Class 2 lever or a Class 3 lever could be used. For a Class 2 lever, the load is between the fulcrum and the effort, and for a Class 3 lever, the effort is between the fulcrum and the load.

The second end of the leg of preload engage/disengage arm 1785 is connected to a second end of a link 1723. A first end of link 1723 is connected to an electric actuator, which is this example is implemented as a solenoid 1720 having a plunger 1721. In this aspect, the first end of link 1723 is connected to plunger 1721. The electric actuator is connected to controller 290. In response to commands from controller 290, the electric actuator is enabled and disabled.

Emergency instrument release button 1082, preload engage/disengage arm 1785, preload engagement arm 1786, torsional spring 1789, the electric actuator and link 1723 form a preload engage/disengage mechanism of preload assembly 1080. Hence, both the preload engage/disengage mechanism and preload assembly 1080 are mechanical structures that a coupled to a controller.

Preload engage/disengage arm 1785 is rotatably coupled to second pivot pin 1788. Preload engage/disengage arm 1785 is couplable to and decouplable from rolling pin 1786P of preload engagement arm 1786. Torsional spring 1789 mounted on second pivot pin 1788 and is coupled to preload engage/disengage arm 1785. Torsional spring 1789 is configured to provide a torque on preload engage/disengage arm 1785 to hold preload engage/disengage arm 1785 in a disengaged position from rolling pin 1786P. See FIGS. 18A and 18B.

Initially, as shown in FIG. 17A, cam follower assembly 1783 in preload assembly 1080 is positioned in a valley in a preload track 1725 on mid-carriage 1620, e.g., is positioned at a first location—a home location—on preload track 1725. At the first location, a light preload spring in each drive output assembly of motor pack 1746 has been compressed, and the first preload force is applied to each disk in the disk stack (See FIG. 4E). As surgical device assembly 300 is moved distally a distance Zload by insertion assembly 331 from the first location to a second location the instrument manipulator assembly housing is moved distance Zload.

Pivot pin 1784, on which cam follower assembly 1783 is rotatably mounted, is coupled to instrument manipulator assembly housing of instrument manipulator assembly 1040. Thus, as insertion assembly 331 moves the instrument manipulator assembly housing distally a distance Zload, pivot pin 1784 moves cam follower assembly 1783 the same distance Zload. In one aspect, distance Zload is 3.85 inches.

As described above, wheel 1783W is rotatably attached to a first end of cam follower assembly 1783, and wheel 1783W rides on preload track 1725. Thus, as cam follower assembly 1783 moves distally, wheel 1783W follows the contour of preload track 1725. However the distance between preload track 1725 and pivot pin 1784 diminishes as cam follower assembly 1783 moves distally. Consequently, as cam follower assembly 1783 rides up ramp 1725R in preload track 1725, cam follower assembly 1783 rotates from a first position illustrated in FIG. 17A to a second position as illustrated in FIG. 17B and moves motor pack 1746 a distance that is greater than the distance traveled by the instrument manipulator assembly housing. Thus, the rotation of cam follower assembly 1783 displaces motor pack 1746 a predetermined distance Δ distally relative to the instrument manipulator assembly housing.

Two acts are performed by cam follower assembly 1783 as cam follower assembly 1783 travels along preload track 1725. As cam follower assembly 1783 moves up ramp 1725R and rotates, the rotation of cam follower assembly 1783 pushes motor pack distally a distance greater than distance Zload, e.g., motor pack 1746 moves a distance (Zload+Δ). In addition, as cam follower assembly 1783 moves up ramp 1725R, cam follower assembly 1783 transfers a force to motor pack 1746, which in turn compresses both the light preload spring and the high preload spring in each drive output assembly so that a second preload force— the high preload force—is asserted on each drive output disk of instrument manipulator assembly 1040. Of course, this is true only when an instrument has been installed, because otherwise the springs do not compress.

FIGS. 18A to 18E are illustrations of one implementation of acts performed in the automatic setting of the preload by preload assembly 1080. The operation of preload assemblies 480 and 980 is the same as illustrated in FIGS. 18A to 18E, in one aspect.

When sterile adapter assembly 250 is mounted on instrument manipulator assembly 1040 in INSTALL STERILE ADAPTER act 817, instrument manipulator assembly 1040 sends a signal to controller 290 indicating the presence of sterile adapter assembly 250.

When a user depresses clutch button 1044 and moves instrument manipulator assembly 1040 proximally, the instrument manipulator assembly housing moves proximally twice as fast as preload engagement ridge 1726 on preload track 1725. This is because distal carriage 1630 to which instrument manipulator assembly 1040 is attached moves twice as far as mid carriage 1620 to which preload track 1725 is attached. In this aspect, preload engagement ridge 1726 extends from a distal portion of preload track 1725.

Initially, when instrument manipulator assembly 1040 is at the home position, there is a gap 1801 between preload engagement ridge 1726 on preload track 1725 and preload engagement surface 1786S of preload engagement arm 1786. Controller 290 commands the insertion assembly to move the instrument manipulator assembly in the proximal direction from the home position. As the instrument manipulator assembly housing moves proximally, preload engagement ridge 1726 moves proximally at half the speed of preload engagement arm 1786 and the instrument manipulator assembly housing and insertion assembly 331 shortens. Thus, mid-carriage 1620 and distal carriage 1630 move relatively closer together closing gap 1801 between preload engagement ridge 1726 on preload track 1725 and preload engagement surface 1786S of preload engagement arm 1786.

As gap 1801 closes (FIG. 18B), surface 1786S of preload engagement arm 1786 engages preload engagement ridge 1726 on preload track 1725. While the proximal motion of preload engagement arm 1786 is constrained to move proximally with preload track 1725, instrument manipulator assembly 1040 continues to move proximally with distal carriage 1630 and linear rail 1787 slides relative to the rail in instrument manipulator housing. Arm 1782 holds motor pack 1746 in place as the instrument manipulator housing continues to move proximally which extends the motor pack return spring.

When instrument manipulator assembly 1040 is a predetermined distance proximal to the home position, e.g., 2 mm, the hook on a second end of the lever included in preload engage/disengage arm 1785 is proximal to rolling pin 1786P in the first end of preload engagement arm 1786 (FIG. 18C). However, torsional spring 1789 about pivot pin 1788 prevents preload engage/disengage arm 1785 from rotating clockwise to engage rolling pin 1786P.

When instrument manipulator assembly reaches the fully withdrawn position (a third position), controller 290 fires solenoid 1720, which moves plunger 1721 in the proximal direction. The motion of plunger 1721 in the proximal direction moves link 1723 in the proximal direction, which in turn causes the hook on preload engage/disengage arm 1785 to rotate clockwise until the hook on preload engage/disengage arm 1785 engages rolling pin 1786P (FIG. 18D).

Figures 18A, 18B:
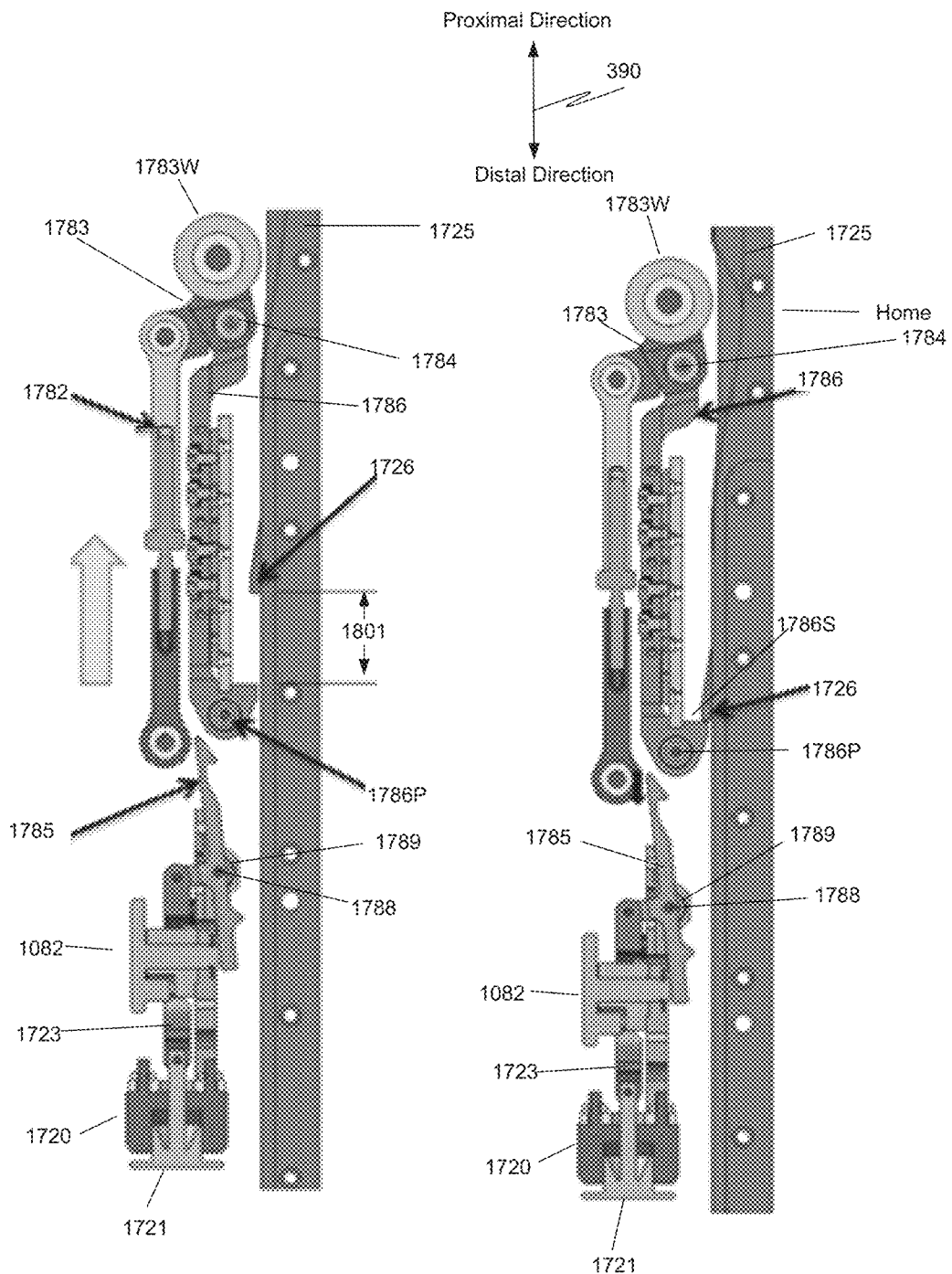

After the engagement of the hook on preload engage/disengage arm 1785 on rolling pin 1786P, controller 290 causes instrument manipulator assembly 1040 to move distally to the home position so that there is a gap between preload engagement ridge 1726 on preload track 1725 and preload engagement surface 1786S of preload engagement arm 1786 (FIG. 18E). In this position, a motor pack return spring in instrument manipulator assembly pulls motor pack 1746 in the distal direction. The force supplied by the motor pack return spring is sufficient to keep the hook of preload engage/disengage arm 1785 engaged with rolling pin 1786P. This puts the hook under tension so that torsional spring 1789 cannot rotate preload engage/disengage arm 1785 in the counter-clockwise direction. Consequently, controller 290 removes the fire command to solenoid 1720. As illustrated in FIGS. 18A to 18E, instrument manipulator assembly 1040 is automatically configured under the control of controller 290 to set the first preload on motor pack 1746.

FIGS. 19A to 19C are illustrations of one implementation of acts performed in the automatic releasing of the preload by preload assembly 1080, in one aspect. The operation of preload assemblies 480 and 980 is the same as illustrated in FIGS. 19A to 19C.

As instrument manipulator assembly 1040 and preload assembly 1080 are moved proximally, cam follower assembly 1783 (FIG. 17B) moves proximally, wheel 1783W follows the contour of preload track 1725. However the distance between preload track 1725 and pivot pin 1784 increases as cam follower assembly 1783 moves proximally. Consequently, as cam follower assembly 1783 rides down ramp 1725R in preload track 1725, cam follower assembly 1783 rotates from the second position illustrated in FIG. 17B to the position as illustrated in FIG. 17A. This releases the second preload so that when preload assembly 1080 is at the home position, as shown if FIG. 19A, only the first preload force is active. This also withdraws the hard stops from sterile adapter assembly 250 so that instrument 260 can be removed, because the movable manipulator-instrument interface plate can be moved proximally when the hard stops are withdrawn.

With respect to FIG. 19A, controller 290 activates the motor that moves instrument manipulator assembly 1040 proximally. The instrument manipulator assembly housing moves proximally twice as fast as preload engagement ridge 1726 on preload track 1725. This is because distal carriage 1630 to which instrument manipulator assembly 1040 is attached moves twice as far as mid carriage 1620 to which preload track 1725 is attached.

Initially, there is a gap between preload engagement ridge 1726 on preload track 1725 and preload engagement surface 1786S of preload engagement arm 1786 (FIG. 19A). As the instrument manipulator assembly housing moves proximally, preload engagement ridge 1726 moves proximally at half the speed of preload engagement arm 1786 and the instrument manipulator assembly housing and insertion assembly 331 shortens. Thus, mid-carriage 1620 and distal carriage 1630 move relatively closer together closing the gap between preload engagement ridge 1726 on preload track 1725 and preload engagement surface 1786S of preload engagement arm 1786.

As the gap closes (FIG. 19B), surface 1786S of preload engagement arm 1786 engages preload engagement ridge 1726 on preload track 1725. While the proximal motion of preload engagement arm 1786 is constrained to move proximally with preload track 1725, instrument manipulator assembly 1040 continues to move proximally with distal carriage 1630 and linear rail 1787 slides relative to the rail in instrument manipulator housing.

When instrument manipulator assembly 1040 is a predetermined distance proximal to the home position, e.g., 2 mm, the hook on a second end of the lever included in preload engage/disengage arm 1785 is proximal to rolling pin 1786P in the first end of preload engagement arm 1786 (FIG. 18C). Since solenoid 1720 is not active, torsional spring 1789 about pivot pin 1788 rotates preload engage/disengage arm 1785 counter-clockwise to disengage the hook from rolling pin 1786P.

After the dis-engagement of the hook on preload engage/disengage arm 1785 to rolling pin 1786P, controller 290 causes instrument manipulator assembly 1040 to move distally to the home position. Since the hook on preload engage/disengage arm 1785 is disengaged from preload engagement arm 1786, there no force on motor pack 1746 in the distal direction, The motor pack is not displaced distally relative to the instrument manipulator housing, and so no preload force is present as instrument manipulator assembly 1040 is moved distally. Thus, as illustrated in FIGS. 19A to 19C, instrument manipulator assembly 1040 is automatically configured under the control of controller 290 to reset the first preload on motor pack 1746 and to prevent application of any preload force as instrument manipulator assembly 1040 is moved distally from a fully withdrawn position to and beyond the home position.

If insertion assembly 331 jams in the extended position, the high preload force must be released so that instrument 260 can be removed. To remove instrument 260, a user pushes emergency instrument release button 1082 (FIG. 10A). In response to the force provided by the user, emergency instrument release button 1082 applies a force to the first end of preload engage/disengage arm 1785. The force on the first end preload engage/disengage arm 1785 causes preload engage/disengage arm 1785 to rotate about pivot pin 1788 and disengage the hook on the second end of preload engage/disengage arm 1785 from rolling pin 1786P that is mounted in the second end of preload engagement arm 1786.

Recall that the motor pack return spring is mounted between instrument manipulator assembly housing and motor pack 1746 and is stretched when the high preload force is applied. Consequently, when preload engage/disengage arm 1785 disengages from preload engagement arm 1786, the motor pack return spring retracts motor pack 1746 to a fully withdrawn position.

At the fully withdrawn position, there is no preload force, and so the drive output disk is disengaged from the intermediate disk. In addition, the plurality of hard stops is withdrawn so that both instrument sterile adapter assembly 250 and instrument 260 can be dismounted. If the distal end of instrument 260 is not straight, as a person withdraws the instrument, the cannula forces the distal end of instrument 260 to straighten because the disk stack without the preload force and without drive output disk engaged is back drivable.

Figure 20A:
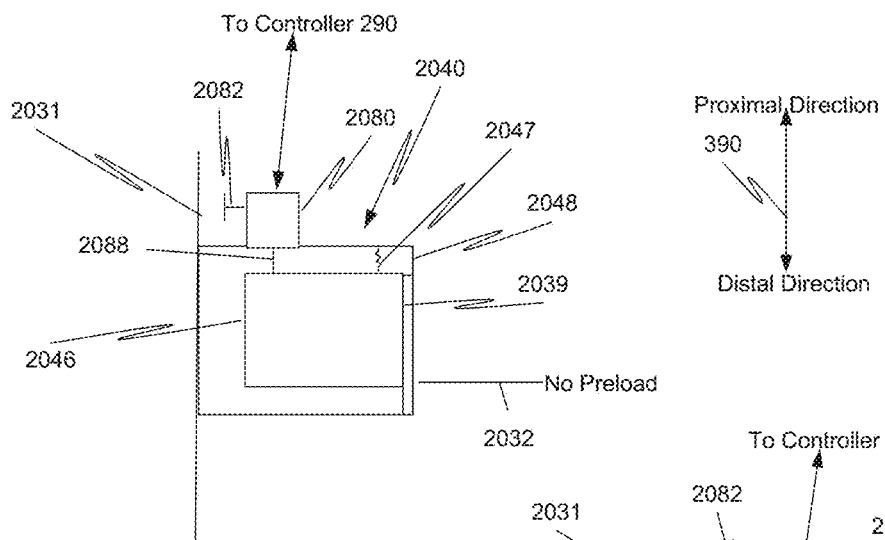
FIGS. 20A to 20C illustrate different preload states of an instrument manipulator assembly having a preload assembly that is directly controlled by a controller.

FIG. 20A shows an instrument manipulator assembly 2040 affixed to an insertion assembly 2031 (also called insertion mechanism 2031). Instrument manipulator assembly 2040 is another example of each of instrument manipulator assemblies 240, 440, and 1040. Insertion assembly 2031 is an example of insertion assembly 331. A position of instrument manipulator assembly 2040 is determined by insertion assembly 2031 and varies from a home position to a fully extended position. In the fully extended position, insertion assembly 2031 is fully extended.

Instrument manipulator assembly housing 2048, sometimes referred to as housing 2048, is fixedly attached to a distal end of insertion assembly 2031, and so instrument manipulator assembly housing 2048 moves with movement of insertion assembly 2031 from the home position to the fully extended position.

A motor pack 2046 within instrument manipulator assembly housing 2048 can move on rail 2039. Motor pack 2046 can move in the distal and proximal directions relative to instrument manipulator assembly housing 2048. Motor pack 2046 is coupled to instrument manipulator assembly housing 2048 by a motor pack return spring 2047, sometimes referred to as return spring 2047. The elements included with motor pack 2046 are the same as the elements described above with respect to motor pack 446, in one aspect. Motor pack return spring 2047 is equivalent to motor pack return spring 447.

Preload assembly 2080 is mounted to instrument manipulator assembly housing 2048, and so moves with housing 2048. Preload assembly 2080 is connected to motor pack 2046 by an arm 2088. Preload assembly 2080 includes an emergency instrument release button 2082.

Unlike motor pack 446 that is movably coupled to insertion assembly 431 by preload assembly 480, motor pack 2046 is not movably coupled to insertion assembly 2031 by preload assembly 2080. However, preload assembly 2080 has the capability to move motor pack 2046 relative to housing 2048 irrespective of the position of instrument manipulator assembly 2040 relative to the home position. Thus, in contrast to the aspect in FIGS. 18A to 18E and 19A to 19C, where as the instrument manipulator assembly moved from the home position, the preload assembly moved along the track and increased the preload from the first preload to the second preload. Here, preload assembly 2080 is under the direct control of controller 290, e.g., a motor controller in controller 290, and so the preload can be increased, or decreased irrespective of the position of instrument manipulator assembly 2040 relative to the home position, and irrespective of whether instrument manipulator assembly 2040 is being moved by insertion assembly 2031 or is stationary.

When no preload is desired and when motor pack 2046 is not displaced in the distal direction relative to instrument manipulator assembly housing 2048, controller 290 does not take any action. (Note that the preload desired is determined, in one aspect, by the state of instrument manipulator assembly 2040, as described above with respect to FIG. 8.) In this case, motor pack 2046 is at a no preload position 2032 relative to instrument manipulator housing 2048 irrespective of where between the home position and the fully extended position instrument manipulator assembly is positioned.

Movement of instrument manipulator assembly 2040 alone from the home position to the fully extended position, or from the fully withdrawn position to the home position does not change the preload. The preload changes only if controller 290 sends a command directly to preload assembly 2080 to make a change, or if emergency instrument release button 2082 is activated. With motor pack 2046 at no preload position 2032, if a sterile adapter assembly were mounted in the distal face of instrument manipulator assembly 2040 there would be no preload force on the intermediate disks of the sterile adapter assembly.

If a low preload is desired and if motor pack 2046 is not displaced in the distal direction relative to instrument manipulator assembly housing 2048, i.e., motor pack is at no preload position 2032, controller 290 commands preload assembly 2080 to move arm 2088 in the distal direction to move motor pack 2046 to low preload position 2033. As motor pack 2046 is moved distally relative to instrument manipulator housing 2048, motor pack return spring 2047 is extended.

Figure 20B:
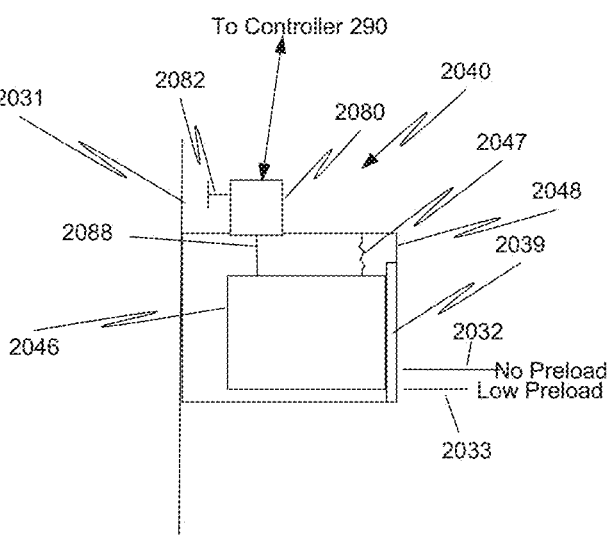

If a sterile adapter assembly were mounted in the distal face of instrument manipulator assembly 2040 with motor pack 2046 at low preload position 2033, there would be a low preload force, e.g., a first preload force, on the intermediate disks of the sterile adapter assembly. In the examples of FIGS. 20A and 20B, the preload force was increased by controller 290, but instrument manipulator assembly 2040 was not moved by insertion assembly 2031. Alternatively, the preload force can be increased by controller 290 as instrument manipulator assembly is moved by insertion assembly 290. If emergency instrument release button 2082 is activated when motor pack 2046 is at low preload position 2033, the preload mechanism in preload assembly 2080 is disengaged, and motor pack return spring 2047 retracts motor pack 2046 in the proximal direction to no preload position 2032.

If a low preload is desired and if motor pack 2046 is at high preload position 2034 relative to instrument manipulator assembly housing 2048, i.e., motor pack is at high preload position 2034, controller 290 commands preload assembly 2080 to move arm 2088 in the proximal direction to move motor pack 2046 to low preload position 2033. As motor pack 2046 is moved proximally relative to instrument manipulator housing 2048, motor pack return spring 2047 is contracted. Again, this could be done without or with insertion mechanism moving instrument manipulator assembly 2040, because the preload force supplied by preload assembly 2080 can be changed independent of the position of preload assembly relative to the home position, and independent of whether insertion assembly 2031 is moving instrument manipulator assembly 2040. Change of the preload is not dependent on a command from controller 290 to insertion mechanism 2031 to change the position of instrument manipulator assembly 2040, which is different from the embodiments described with respect to FIGS. 19A to 19C.

The control of the preload by controller 290 is irrespective of control of insertion assembly 2031 on which instrument manipulator assembly 2040 is mounted. This means that unlike the previously described aspects, a command by controller 290 to insertion mechanism 2031 to change the position of instrument manipulator assembly 2040 cannot change the preload. Rather, controller 290 commands preload assembly 2080 directly to change the preload. It is recognized that controller 290 may command preload assembly 2080 to change the preload based on a position of instrument manipulator assembly 2040. Thus, a command to preload assembly 2080 may be coupled to a command to insertion assembly 2031, but the command to insertion assembly 2031 cannot change the preload in this aspect, and so the control of the preload by controller 290 is said to be irrespective of control of insertion assembly 2031 on which instrument manipulator assembly 2040 is mounted.

If no preload is desired and if motor pack 2046 is at low preload position 2033 relative to instrument manipulator assembly housing 2048, i.e., motor pack 2046 is at low preload position 2033, controller 290 commands preload assembly 2080 to move arm 2088 in the proximal direction to move motor pack 2046 to no preload position 2032. As motor pack 2046 is moved proximally relative to instrument manipulator housing 2048, motor pack return spring 2047 is contracted. Yet again, this could be done without or with insertion mechanism 2031 moving instrument manipulator assembly 2040, because the preload force supplied by preload assembly 2080 can be changed by controller 290 independent of the position of preload assembly 2080 relative to insertion assembly 2031 and independent of the position of instrument manipulator assembly 2040 relative to the home position. Of course, this also can be done as insertion assembly 2031 moves instrument manipulator assembly 2040.

If a high preload is desired, controller 290 commands preload assembly 2080 to move arm 2088 in the distal direction to move motor pack 2046 to high preload position 2034. As motor pack 2046 is moved distally relative to instrument manipulator housing 2048, motor pack return spring 2047 is extended.

If a sterile adapter assembly were mounted in the distal face of instrument manipulator assembly 2040 with motor pack 2046 at high preload position 2034, there would be a high preload force, e.g., a second preload force, on the intermediate disks of the sterile adapter assembly. If emergency instrument release button 2082 is activated when motor pack 2046 is at high preload position 2034, the preload mechanism in preload assembly 2080 is disengaged, and motor pack return spring 2047 retracts motor pack 2046 in the proximal direction to no preload position 2032, which removes the high preload force.

Figure 20C:
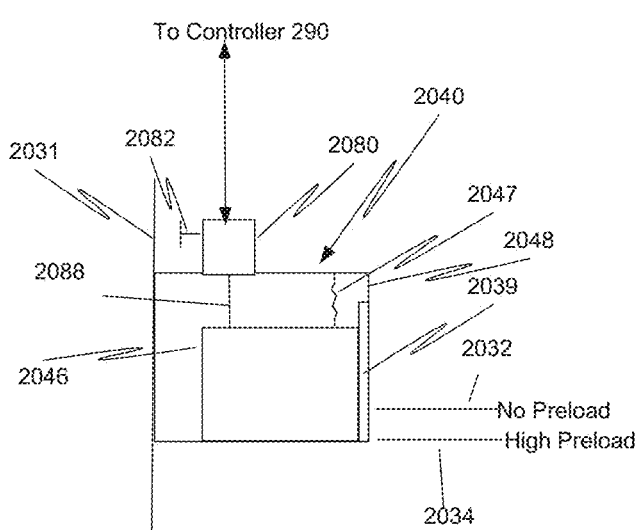

If motor pack 2046 is high preload position 2033 relative to instrument manipulator assembly housing 2048, controller 290 can command preload assembly 2080 to move motor pack 2046 proximally to either low preload position 2033 or to no preload position 2032. In the examples of FIGS. 20A, 20B, and 20C, the preload force was increased by controller 290, but insertion assembly 2031 did not move instrument manipulator assembly 2040. The preload force could also be changed by controller 290 in each of these examples as insertion assembly 2031 moves instrument manipulator assembly 2040.

In the examples discussed below with respect to FIGS. 21A to 21C and in the examples illustrated in FIGS. 4A to 4G, the mechanical instrument removal lockout—the prevention of the movable body in the sterile adapter assembly from moving proximally—is activated by moving the motor pack in the instrument manipulator assembly. In another aspect illustrated in FIGS. 21D and 21E, the mechanic instrument removal lockout is independent of movement of any part of instrument manipulator assembly 2040. In this aspect, a mechanical instrument removal lockout assembly 2090 is mounted to housing 2048 of instrument manipulator assembly 2040. Mechanical instrument removal lockout assembly 2090 is connected to a lockout arm 2091, sometimes referred to as arm 2091, which includes a plurality of stops on the proximal end. The plurality of stops is optional and is used an example for interfacing with the sterile adapter assemblies described previously. In more general terms, a distal face of arm 2091 could interface with a proximal face of a movable body of a sterile adapter assembly, for example. An emergency instrument release button 2082A is shared between preload assembly 2080 and mechanical instrument removal lockout assembly 2090, in this aspect. A lockout return spring 2047A is connected between a proximal end of lockout arm 2091 and housing 2048, in one aspect.

A sterile adapter assembly 2050 (FIG. 20D) is mounted in the distal face of instrument manipulator assembly 2040. Sterile adapter assembly 2050 includes a moveable manipulator-instrument interface plate 2051C, sometimes referred to as movable body 2051C, which can move in the proximal and distal directions relative to a frame of sterile adapter assembly 2050. Sterile adapter assembly 250 is an example of sterile adapter assembly 2050, and so sterile adapter assembly 2050 is not described in further detail.

As explained previously, when an instrument is mounted or removed from sterile adapter assembly 2050, movable body 2051C is moved in the proximal direction. To prevent removal of the instrument, movable body 2051C is prevented from moving in the proximal direction by mechanical instrument removal lockout assembly 2090 by locking movable body 2051C in place.

An optional mechanical instrument removal lockout assembly 2090 (FIG. 20D) is under the direct control of controller 290, e.g., a motor controller in controller 290. The mechanical instrument removal lockout can be activated or deactivated irrespective of the position of instrument manipulator assembly 2040 relative to the home position, irrespective of whether instrument manipulator assembly 2040 is being moved by insertion assembly 2031 or is stationary, and irrespective of the position of motor pack 2046 relative to housing 2048. The motion of arm 2091 is independent of motion of instrument manipulator assembly 2040 and is independent of motion of motor pack 2046. Arm 2091 moves only when controller 290 commands mechanical instrument removal lockout assembly 2090 to move arm 2091, or when arm 2091 is an extended position, and emergency instrument release button 2082A is activated by a user.

Figure 20D:
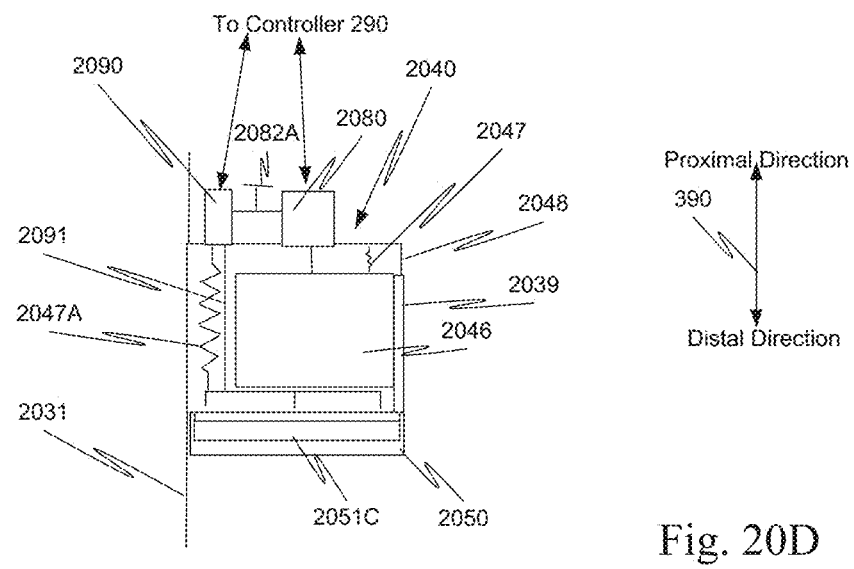
FIGS. 20D and 20E illustrate a mechanical instrument removal lockout assembly having different mechanical instrument removal lockout states that are directly controlled by a controller.
Figure 20E:
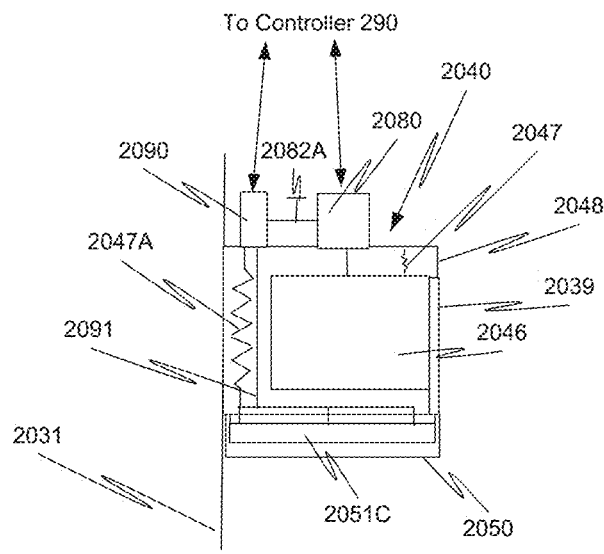

In this aspect, arm 2091 has a proximal position, illustrated in FIG. 20D, and a distal position illustrated in FIG. 20E. In the proximal position, a second position, no part of arm 2091 is in contact with moveable body 2051C of sterile adapter assembly 2050. If mechanical instrument removal lockout assembly 2090 receives an engage lockout command from controller 290, mechanical instrument removal lockout assembly 2090 moves arm 2091 to the distal position (FIG. 20E), which locks movable body 2051C in a distal position in sterile adapter assembly 2050. With moveable body 2051C locked in the distal position, an instrument mounted in sterile adapter assembly cannot be removed.

As arm 2091 moves to the distal position, return spring 2047A is extended. If emergency instrument release button 2082A is activated, arm 2091 is disengaged from mechanical instrument removal lockout assembly 2090, and return spring 2047A pulls arm 2091 to its proximal position (FIG. 20D). Thus, movable body 2051C can be moved in the proximal direction, and the instrument can be removed.

Alternatively, controller 290 can send a disengage lockout command to mechanical instrument removal lockout assembly 2090. When mechanical instrument removal lockout assembly 2090 receives the disengage lockout command from controller 290, mechanical instrument removal lockout assembly 2090 moves arm 2091 form the distal position in FIG. 20E to the proximal position in FIG. 20D, which unlocks movable body 2051C in sterile adapter assembly 2050 and permits movement of movable body 2051C.

Figure 21A:
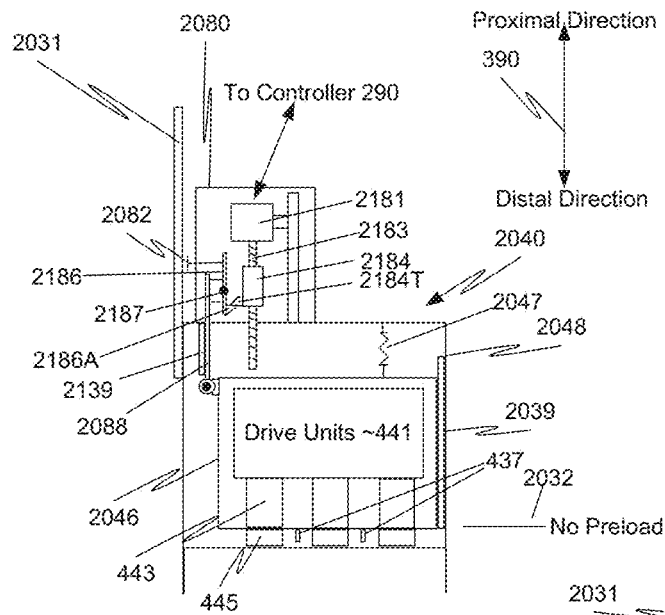
FIGS. 21A to 21C illustrate one aspect of the preload assembly of FIGS. 20A to 20C in further detail.
Figure 21B:
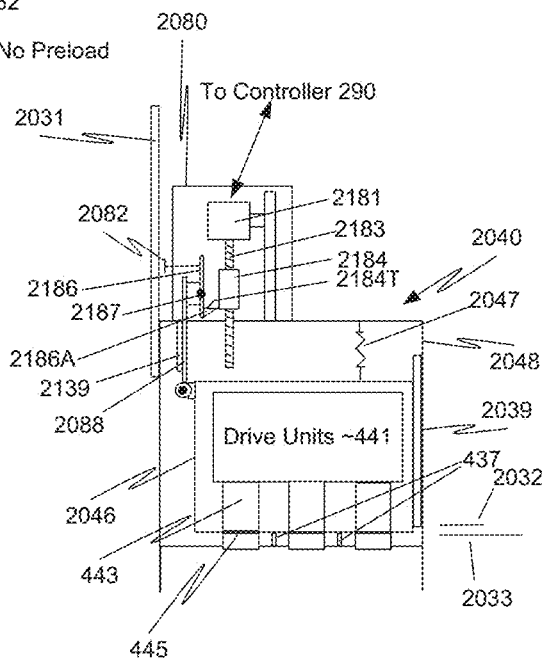
Figure 21C:
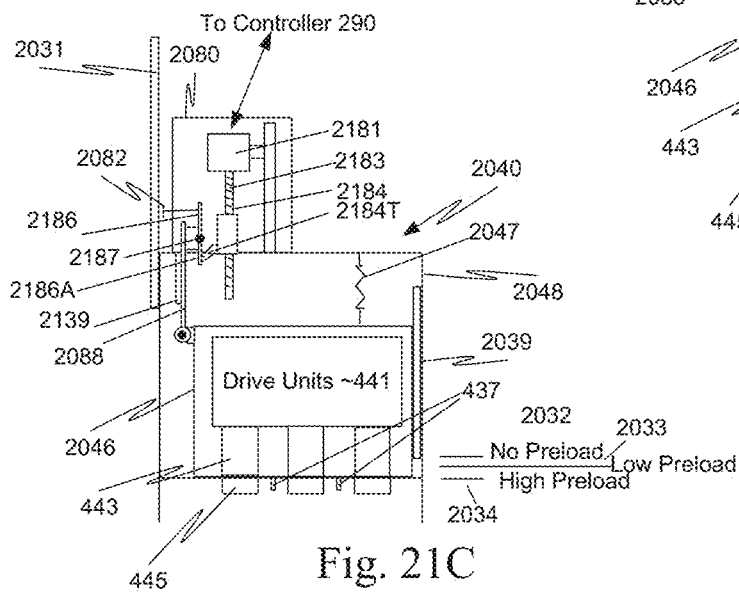

FIGS. 21A to 21C are examples for one aspect of instrument manipulator assembly 2040 and preload assembly 2080 in FIGS. 20A to 20C. Elements in instrument manipulator assembly 2040 in FIGS. 21A to 21C with the same reference numeral as in FIG. 4A are elements equivalent to those in FIG. 4A, and so the description of the elements with respect to FIG. 4A is not repeated here.

In this aspect, preload assembly 2080 includes a motor 2181, e.g., a servomotor, that is connected to controller 290. Motor 2181 is mounted to housing 2048. Motor 2181 drives a screw 2183. A nut 2184 is mounted on screw 2183 and moves proximally or distally as motor 2181 rotates screw 2183. In one aspect, screw 2183 is a threaded shaft of motor 2181. The rotation of the shaft of motor 2181, and hence the distal or proximal movement of nut 2184, is controlled by controller 290. The motor, screw, and nut combination is an example of a movable assembly whose position along an axis is directly controlled by controller 290.

A preload tab 2184T extends from an outer side surface of nut 2184 adjacent to a distal end of nut 2184. Preload tab 2184T has a first planar surface on a distal face and a second planar surface on a proximal face. The first planar surface extends further from the outer side surface of nut 2184 than does the second planar surface. Thus, a surface joining first planar surface to the second planar surface is a ramped surface.

A preload release lever 2186 is mounted on a pivot pin 2187. A torsional spring is mounted around the pivot pin and attached to preload release lever 2186 to maintain preload release lever 2186 in a preload engaged position if emergency instrument release button 2082 is not engaged. Pivot pin 2187 is mounted on arm 2088 that is connected to motor pack 2046. In this example, arm 2088 moves proximally and distally relative to housing 2048 on a rail 2139. Rail 2139 is optional.

A distal end, i.e., a first end, of preload release lever 2186 includes a hook 2186A that engages with and disengages from preload tab 2184T. In this example, hook 2186A has a flat planar surface that extends from a side surface of preload release lever 2186. The flat planar surface of hook 2186A is configured to contact the first planar surface of preload tab 2084T so that distal movement of preload tab 2184T causes preload release lever 2186 to move distally along with preload tab 2184T.

A ramped surface extends from the end of flat planar surface of preload release lever 2186 removed from the side surface of preload release lever 2186 to a distal end of preload release lever 2186. The slope of the ramped surface at the distal end of preload release lever 2186 is the opposite of the slope of the ramped surface on tab 2184T so that hook 2186A and tab 2184T can move by each other in the proximal direction when the preload is released.

Emergency instrument release button 2082 is mounted to apply a force to a proximal end, a second end, of preload release lever 2186. In the example of FIGS. 21B and 21C, if emergency instrument release button 2082 is activated, emergency instrument release button 2082 applies a preload disengage force to the proximal end of preload release lever 2186, which causes preload release lever 2186 to pivot about pivot pin 2187 in a preload disengage direction, clockwise in FIGS. 20B and 20C.

The pivoting of preload release lever 2186 about pivot pin 2187 in a preload disengage direction causes hook 2186A to disengage from tab 2184T of nut 2184. Consequently, motor pack return spring 2047 moves motor pack 2046 in the proximal direction to no preload position 2032 relative to instrument manipulator assembly housing 2048.

To engage the preload, controller 290 commands motor 2181 to move nut 2184 proximally from either the position in FIG. 20B or the position in FIG. 20C to the position in FIG. 20A. Since tab 2184T is distal to hook 2186A, as nut 2184 moves tab 2184T proximally, the ramped surface of tab 2184T contacts the ramped surface of hook 2186A of preload release lever 2186. As tab 2184T continues to move proximally, the ramped surface of tab 2184T pivots preload release lever 2186 until the first planer surface—the distal planar surface—clears the first planar surface of hook 2186A, and then the torsional spring about pivot pin 2187 rotates hook 2186A in the preload engage direction so that first planar surface of hook 2186A and first planar surface of tab 2184T are in contact. This engages the preload mechanism, because now when tab 2184T moves, hook 2186A moves, which in turn moves motor pack 2046.

Specifically, as shown in FIGS. 21A and 21B, when the preload mechanism is engaged and motor pack 2046 is in no preload position 2032 and controller 290 commands preload assembly 2080 to move motor pack 2046 to low preload position 2033, motor 2181 moves nut 2184 in the distal direction. Movement of nut 2184 in the distal direction causes tab 2184T to apply a force on hook 2186A in the distal direction. The force on hook 2186A moves arm 2088 in the distal direction, which moves motor pack 2046 in the distal direction relative to instrument manipulator housing 2048 to low preload position 2033.

As shown in FIGS. 21B and 21C, when the preload mechanism is engaged and motor pack 2046 is in low preload position 2033 and controller 290 commands preload assembly 2080 to move motor pack 2046 to high preload position 2034, motor 2181 moves nut 2184 in the distal direction. Movement of nut 2184 in the distal direction causes tab 2184T to apply a force on hook 2186A in the distal direction. The force on hook 2186A moves arm 2088 in the distal direction, which moves motor pack 2046 in the distal direction relative to instrument manipulator housing 2048 to high preload position 2034.

In the aspects illustrated in FIGS. 21A to 21C, with respect to emergency instrument release button 2082, preload release lever 2186 is a Class 1 lever because the fulcrum (pivot pin 2187) is between the effort (the force supplied by preload release button 3082) and the load (the coupling between hook 2186A and tab 2184T). While in this example, preload release lever 2186 is implemented as a Class 1 lever, this is illustrative only and is not intended to be limiting. In other aspects, a Class 2 lever or a Class 3 lever could be used. For a Class 2 lever, the load is between the fulcrum and the effort, and for a Class 3 lever, the effort is between the fulcrum and the load.

All of the states and all of the acts in FIG. 8 can be achieved using instrument manipulator assembly 2040 that includes preload assembly 2080. Thus, the description of FIG. 8 is not repeated for the aspects of instrument manipulator assembly 2040 that includes preload assembly 2080. Here, controller 290 directly controls the preload, and the preload is not dependent upon the movement of instrument manipulator assembly 2040 by insertion mechanism 2031. Thus, the acts in FIG. 8 where controller 290 moved the instrument manipulator assembly to set or reset the preload mechanism are not needed when instrument manipulator assembly 2040 that includes preload assembly 2080 is used.

Thus, in one aspect, controller 290 maintains no preload force on motor pack 2046 of instrument manipulator assembly 2040 if sterile adapter assembly 2050 is not mounted on instrument manipulator assembly 2040. Controller issues a command directly to preload assembly 2080 to increase the preload force on motor pack 2046 of instrument manipulator assembly 240 from the no preload force to a first preload force after sterile adapter assembly 2050 is mounted on instrument manipulator assembly 2040. Controller issues another command directly to preload assembly 2080 to increase the preload force on motor pack 2046 of instrument manipulator assembly 240 from the first preload force to a second preload force after an instrument is mounted on sterile adapter assembly 2050.

In one aspect, mechanical instrument removal lockout assembly 2090 is implemented with elements equivalent to those shown for preload assembly 2080 in FIG. 21A, and so that description is not repeated for mechanical instrument removal lockout assembly 2090. In another aspect, assemblies 2080 and 2090 are combined in a single assembly that performs both the preload functionality and the mechanical instrument removal lock functionality with the two functionalities being independent of each other.

In some of the above examples, the terms "proximal" or "proximally" are used in a general way to describe an object or element which is closer to a manipulator arm base along a kinematic chain of system movement or farther away from a remote center of motion (or a surgical site) along the kinematic chain of system movement. Similarly, the terms "distal" or "distally" are used in a general way to describe an object or element which is farther away from the manipulator arm base along the kinematic chain of system movement or closer to the remote center of motion (or a surgical site) along the kinematic chain of system movement.

As used herein, "first," "second," "third," "fourth," etc. are adjectives used to distinguish between different components or elements. Thus, "first," "second," "third," "fourth," etc. are not intended to imply any ordering of the components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. A computer-assisted surgical apparatus comprising:
   a preload assembly including a preload engage/disengage mechanism; and
   a controller coupled to the preload assembly, the controller being configured:
      to move the preload assembly until the preload assembly is fully withdrawn;
      to activate the preload engage/disengage mechanism if the preload assembly is fully withdrawn; and
      to move the preload assembly to a home position after activating the preload engage/disengage mechanism.

2. The apparatus of claim 1,
a surgical instrument manipulator assembly comprising the preload assembly, a housing, and a motor pack movably mounted in the housing; and
the preload assembly further comprising:
  a cam following assembly comprising a wheel and a body, the wheel being configured to ride on a preload track, the body is rotatably coupled to a first pivot pin, the body having a first and a second end, the second end of the body being coupled to the motor pack, and the first end of the body being coupled to the wheel.

3. The apparatus of claim 2, the preload engage/disengage mechanism further comprising:
  a preload engagement arm comprising a first end and a second end, the first end of the preload engagement arm being coupled to the first pivot pin; and
  a rolling pin mounted in the second end of the preload engagement arm.

4. The apparatus of claim 3, the preload engage/disengage mechanism further comprising:
  a second pivot pin;
  a preload engage/disengage arm rotatably coupled to the second pivot pin, the preload engage/disengage arm being couplable to and decouplable from the rolling pin; and
  a torsional spring mounted on the second pivot pin and coupled to the preload engage/disengage arm, the torsional spring being configured to provide a torque on the preload engage/disengage arm to hold the preload engage/disengage arm in a disengaged position from the rolling pin.

5. The apparatus of claim 4, the preload engage/disengage mechanism further comprising:
  an electronic actuator coupled to the preload engage/disengage arm and to the controller, wherein if an engage command from the controller is received by the electronic actuator, the electronic actuator provides a torque on the preload engage/disengage arm to hold the preload engage/disengage arm in an engaged position with respect to the rolling pin.

6. The apparatus of claim 4, the preload engage/disengage mechanism further comprising an emergency instrument release button coupled to the preload engage/disengage arm.

7. An apparatus comprising:
  a surgical instrument manipulator assembly comprising a housing, a motor pack and a preload assembly, the motor pack being movably mounted in the housing, and the preload assembly comprising a preload engage/disengage mechanism;
  an insertion assembly coupled to the surgical instrument manipulator assembly, the insertion assembly comprising a preload track;
  a controller coupled to the surgical instrument manipulator assembly, the insertion assembly, and the preload assembly, the controller being configured:
    to command the insertion assembly to move the preload assembly until the preload assembly is fully withdrawn;
    to command the preload engage/disengage mechanism to engage a preload, if the preload assembly is fully withdrawn; and
    to command the insertion assembly to move the preload assembly to a home position after engaging the preload.

8. The apparatus of claim 7, the preload engage/disengage mechanism further comprising:
  a preload engagement arm comprising a first end and a second, the first end of the preload engagement arm being coupled to a first pivot pin; and
  a rolling pin mounted in the second end of the preload engagement arm.

9. The apparatus of claim 8, the preload engage/disengage mechanism further comprising:
  a second pivot pin;
  a preload engage/disengage arm rotatably coupled to the second pivot pin, the preload engage/disengage arm being couplable to and decouplable from the rolling pin; and
  a torsional spring mounted on the second pivot pin and coupled to the preload engage/disengage arm, the torsional spring being configured to provide a torque on the preload engage/disengage arm to hold the preload engage/disengage arm in a disengaged position from the rolling pin.

10. The apparatus of claim 9, the preload engage/disengage mechanism further comprising:
  an electronic actuator coupled to the preload engage/disengage arm and to the controller, wherein if an engage command from the controller is received by the electronic actuator, the electronic actuator provides a torque on the preload engage/disengage arm to hold the preload engage/disengage arm in an engaged position with respect to the rolling pin.

11. The apparatus of claim 9, the preload engage/disengage mechanism further comprising an emergency instrument release button coupled to the preload engage/disengage arm.

12. A method comprising:
  moving, by a controller, a preload assembly of a surgical instrument manipulator assembly to a fully withdrawn position; and
  issuing, by the controller, a command to activate a preload engage/disengage mechanism of the preload assembly if the preload assembly is fully withdrawn.

13. The method of claim 12, further comprising:
  moving, by the controller, the preload assembly to a home position after activating the preload engage/disengage mechanism.

14. The method of claim 13, further comprising:
  moving, by the controller, the preload assembly to the fully withdrawn position to automatically release the preload engage/disengage mechanism.

15. The method of claim 14, wherein moving the preload assembly to the fully withdrawn position automatically releases a preload force on a motor pack of the surgical instrument manipulator assembly.

* * * * *

UNITED STATES PATENT AND TRADEMARK OFFICE
CERTIFICATE OF CORRECTION

PATENT NO. : 11,020,190 B2  
APPLICATION NO. : 16/317484  
DATED : June 1, 2021  
INVENTOR(S) : Robert E. Holop and Todd R. Solomon Page 1 of 1

It is certified that error appears in the above-identified patent and that said Letters Patent is hereby corrected as shown below:

On the Title Page

Item (87) PCT Pub. Date:  
Please delete "Jan. 8, 2018" and insert --Jan. 18, 2018--.

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*